United States Patent
Inoue et al.

(10) Patent No.: US 8,889,266 B2
(45) Date of Patent: *Nov. 18, 2014

(54) ORGANOMETALLIC COMPLEX, AND LIGHT-EMITTING ELEMENT, LIGHT-EMITTING DEVICE AND ELECTRONIC-DEVICE USING THE ORGANOMETALLIC COMPLEX

(75) Inventors: Hideko Inoue, Kanagawa (JP); Satoko Shitagaki, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 663 days.

This patent is subject to a terminal disclaimer.

(21) Appl. No.: 11/908,010

(22) PCT Filed: Mar. 14, 2006

(86) PCT No.: PCT/JP2006/305474
§ 371 (c)(1),
(2), (4) Date: Sep. 7, 2007

(87) PCT Pub. No.: WO2006/098460
PCT Pub. Date: Sep. 21, 2006

(65) Prior Publication Data
US 2009/0015143 A1    Jan. 15, 2009

(30) Foreign Application Priority Data

Mar. 17, 2005 (JP) ................................. 2005-076454
Nov. 30, 2005 (JP) ................................. 2005-346060

(51) Int. Cl.
*H01J 1/63* (2006.01)
*C07F 15/00* (2006.01)
(Continued)

(52) U.S. Cl.
CPC .... *H01L 51/0085* (2013.01); *C09K 2211/1044* (2013.01); *C09K 11/06* (2013.01);
(Continued)

(58) Field of Classification Search
USPC ........................................................ 428/690
See application file for complete search history.

(56) References Cited

U.S. PATENT DOCUMENTS 5,484,922 A    1/1996   Moore et al.
6,780,528 B2   8/2004   Tsuboyama et al.
(Continued)

FOREIGN PATENT DOCUMENTS

CN    1478372 A    2/2004
CN    1678617 A    10/2005
(Continued)

OTHER PUBLICATIONS

Duan, J-P et al, "New Iridium Complexes as Highly Efficient Orange-Red Emitters in Organic Light-Emitting Diodes," Advanced Materials, vol. 15, No. 3, 2003, pp. 224-228.
(Continued)

*Primary Examiner* — J. L. Yang
(74) *Attorney, Agent, or Firm* — Husch Blackwell LLP

(57) ABSTRACT

It is an object of the present invention to provide an organometallic complex which can increase recombination efficiency of electrons and holes. One aspect of the present invention is an organometallic complex having a structure represented by a general formula (1), wherein each of $R^1$ and $R^2$ is any of a halogen group, a —$CF_3$ group, a cyano group, and an alkoxycarbonyl group, each of $R^3$ and $R^4$ is any of hydrogen and an alkyl group having 1 to 4 carbon atoms, and M is an element that belongs to Group 9 or 10 of the periodic table.

(1)

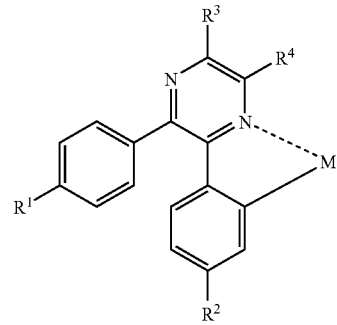

36 Claims, 44 Drawing Sheets

(51) Int. Cl.
*H01L 51/00* (2006.01)
*C09K 11/06* (2006.01)
*H05B 33/14* (2006.01)
*H01L 51/50* (2006.01)

(52) U.S. Cl.
CPC ......... *H01L 51/0079* (2013.01); *H01L 51/5016* (2013.01); *H05B 33/14* (2013.01); *C09K 2211/185* (2013.01); *C07F 15/0033* (2013.01)
USPC ............................ 428/690; 313/504; 548/101

(56) References Cited

U.S. PATENT DOCUMENTS

| | | | |
|---|---|---|---|
| 6,821,646 B2 | 11/2004 | Tsuboyama et al. | |
| 6,830,828 B2 | 12/2004 | Thompson et al. | |
| 6,953,628 B2 | 10/2005 | Kamatani et al. | |
| 7,094,477 B2 | 8/2006 | Kamatani et al. | |
| 7,147,935 B2 | 12/2006 | Kamatani et al. | |
| 7,220,495 B2 | 5/2007 | Tsuboyama et al. | |
| 7,521,130 B2 | 4/2009 | Lee et al. | |
| 7,527,879 B2 | 5/2009 | Kamatani et al. | |
| 7,544,426 B2 | 6/2009 | Kamatani et al. | |
| 7,569,692 B2 | 8/2009 | Nii et al. | |
| 7,589,203 B2 | 9/2009 | Stössel et al. | |
| 7,687,155 B2 | 3/2010 | Kamatani et al. | |
| 7,709,100 B2 | 5/2010 | Kwong et al. | |
| 7,811,677 B2 | 10/2010 | Ohsawa et al. | |
| 7,883,785 B2 | 2/2011 | Stössel et al. | |
| 7,960,038 B2 | 6/2011 | Ohsawa et al. | |
| 8,084,145 B2 | 12/2011 | Inoue et al. | |
| 2001/0019782 A1 | 9/2001 | Igarashi et al. | |
| 2002/0034656 A1 | 3/2002 | Thompson et al. | |
| 2002/0121638 A1 | 9/2002 | Grushin et al. | |
| 2003/0054198 A1 | 3/2003 | Tsuboyama et al. | |
| 2003/0059646 A1* | 3/2003 | Kamatani et al. ............. | 428/690 |
| 2005/0221123 A1 | 10/2005 | Inoue et al. | |
| 2006/0008673 A1* | 1/2006 | Kwong et al. ................ | 428/690 |
| 2006/0127696 A1 | 6/2006 | Stossel et al. | |
| 2006/0182992 A1 | 8/2006 | Nii et al. | |
| 2007/0129545 A1 | 6/2007 | Inoue et al. | |
| 2007/0154733 A1 | 7/2007 | Fukuoka et al. | |
| 2007/0170843 A1 | 7/2007 | Kawamura et al. | |
| 2009/0174324 A1 | 7/2009 | Nii et al. | |
| 2009/0184634 A1 | 7/2009 | Kamatani et al. | |
| 2009/0195153 A1 | 8/2009 | Lee et al. | |
| 2011/0024732 A1 | 2/2011 | Ohsawa et al. | |

FOREIGN PATENT DOCUMENTS

| | | |
|---|---|---|
| EP | 1 535 981 A2 | 6/2005 |
| EP | 1 722 602 A1 | 11/2006 |
| EP | 1 722 605 A1 | 11/2006 |
| JP | 2002-105055 | 4/2002 |
| JP | 2004-107441 | 4/2004 |
| JP | 2005-158668 | 6/2005 |
| JP | 2005-251639 | 9/2005 |
| JP | 2005-314414 | 11/2005 |
| JP | 2005-536565 | 12/2005 |
| JP | 2006-73992 | 3/2006 |
| JP | 2006-507279 | 3/2006 |
| JP | 2006-151887 | 6/2006 |
| JP | 2006-352102 | 12/2006 |
| JP | 2007-161859 | 6/2007 |
| JP | 2007-161860 | 6/2007 |
| JP | 4912704 B2 | 4/2012 |
| WO | WO 2004/037836 A1 | 5/2004 |
| WO | WO 2004/108857 A1 | 12/2004 |
| WO | WO 2005/086540 A1 | 9/2005 |
| WO | WO 2005/115061 A1 | 12/2005 |
| WO | 2006/098460 A1 | 9/2006 |

OTHER PUBLICATIONS

Steel, P.J. et al, "Cyclometallated Compounds V. Double Cyclopalladation of Diphenyl Pyrazines and Related Ligands," Journal of Organometallic Chemistry, vol. 395, 1990, pp. 359-373.
Zhang, G-L et al, "Synthesis and Phosphorescence of a New Iridium(III) Pyrazine Complex," Wuli Huaxue Xuebao, Acta Phys.-Chim. Sin, vol. 19, No. 10, Oct. 19, 2003, pp. 889-891 (with English abstract).
International Search Report re application No. PCT/JP2006/305474, dated Apr. 11, 2006.
Written Opinion re application No. PCT/JP2006/305474, dated Apr. 11, 2006.
O'Brien, D.F. et al, "Improved Energy Transfer in Electrophosphorescent Devices," Applied Physics Letters, vol. 74, No. 3, Jan. 18, 1999, pp. 442-444.
Inoue, H. et al, "A Reaction of Singlet Oxygen with an Unsaturated Organic Molecule, 6.1.4, Quencher and Photosensitizer," *Basic Chemistry Course Photochemistry I*, Maruzen Co., Ltd., Sep. 30, 1999, pp. 106-110 (with English abstract).
Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, Dec. 15, 1999, pp. L1502-L1504.
Baldo, M.A. et al, "High-Efficiency Fluorescent Organic Light-Emitting Devices Using a Phosphorescent Sensitizer," Nature, vol. 403, Feb. 17, 2000, pp. 750-753.
Thompson, M.E. et al, "Phosphorescent Materials and Devices," Proceedings of the $10^{th}$ International Workshop on Inorganic and Organic Electroluminescence, EL '00, Dec. 4, 2000, pp. 35-38.
Shavaleev, N.M. et al, "Sensitized Near-Infrared Emission from Complexes of $Yb^{III}$, $N^{III}$, and $Er^{III}$, by Energy-Transfer from Covalently Attached $Pt^{II}$-Based Antenna Units," Chemistry—A European Journal, vol. 9, No. 21, 2003, pp. 5283-5291.
Slater, J.W. et al, "Cyclometallated Nitrogen Heterocycles," Journal of Organo Metallic Chemistry, vol. 688, Aug. 29, 2003, pp. 112-120.
Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with English abstract).
Tsutsui, T., "Mechanism of Organic EL Element and Luminous Efficiency," *Textbook of the $3^{rd}$ Seminar at Division of Organic Molecular Electronics and Bioelectronics*, 1993, pp. 31-37, Division of Molecular Electronics and Bioelectronics, The Japan Society of Applied Physics (with English translation).
International Search Report re application No. PCT/JP2006/323882, dated Jan. 16, 2007.
Written Opinion re application No. PCT/JP2006/323882, dated Jan. 16, 2007.
European Search Report re application No. EP 07005200.6, dated Jul. 23, 2007.
Steel, P.J. et al., "Cyclometallated Compounds V. Double Cyclopalladation of Diphenyl Pyrazines and Related Ligands," Journal of Organometallic Chemistry, vol. 395, No. 3, 1990, pp. 359-373.
Zhang, G-L et al, "Synthesis and Luminescence Property of a New Yellow Phosphorescent Iridium(III) Pyrazine Complex," Chemical Journal of Chinese Universities, vol. 25, No. 3, Mar. 1, 2004, pp. 397-400 (with full English translation, pp. 1-8).
European Search Report re application No. EP 06715702.4, dated Jul. 23, 2010.
Office Action re U.S. Appl. No. 11/607,649, dated Feb. 3, 2010.
Office Action re U.S. Appl. No. 11/092,816, dated May 20, 2010.
Declaration of Satoshi Seo, filed in U.S. Appl. No. 11/607,649, dated Jun. 1, 2010.
Final Rejection re U.S. Appl. No. 11/607,649, dated Aug. 18, 2010.
Declaration of Satoshi Seo, filed in U.S. Appl. No. 11/092,816, dated Sep. 21, 2010.
Yersin, H. et al, "Triplet Emitters for Organic Light-Emitting Diodes: Basic Properties," *Highly Efficient OLEDs with Phosphorescent Materials*, Wiley-VCH Verlag GmbH & Co., 2008, pp. 1-18.
European Office Action re application No. EP 06715702.4, dated Jun. 24, 2011.
Zhang, G.-L. et al., "Synthesis and Phosphorescence Property of a New Pyrazine Iridium(III) Complex," Wuli Huaxue Xuebao, (Acta Phys.-Chim. Sin.), vol. 19, No. 10, Oct. 2003, pp. 889-891 (with English translation).
Second Declaration of Satoshi Seo, filed in U.S. Appl. No. 11/092,816, dated May 9, 2011.

(56) References Cited

OTHER PUBLICATIONS

Izumi, T. et al, "Synthesis and Carbonylation Reaction of 2,5-Diphenylpyrazine Palladium Complex," Yamagata Daigaku Kiyo Kogaku, vol. 15, No. 2, Feb. 20, 1979, pp. 213-218.

Xu, M.-L. et al, "Synthesis and Characterization of Phosphorescent Cyclometalated Iridium Complexes Containing 2,5-Diphenylpyridine Based Ligands," Applied Organometallic Chemistry, vol. 19, No. 12, Dec. 1, 2005, pp. 1225-1231.

Xu, M.-L. et al, "Optical and Electroluminescent Properties of a New Ir(III) Complex—fac-tris[2,5-di(4-methoxyphenyl) pyridinato-C,N]Iridium(III)," Thin Solid Films, vol. 497, Feb. 21, 2006, pp. 239-242.

* cited by examiner

ORGANOMETALLIC COMPLEX, AND LIGHT-EMITTING ELEMENT, LIGHT-EMITTING DEVICE AND ELECTRONIC-DEVICE USING THE ORGANOMETALLIC COMPLEX

TECHNICAL FIELD

The present invention relates to a substance capable of emitting light by current excitation, particularly an organometallic complex that emits light by current excitation. In addition, the present invention relates to a light-emitting element and a light-emitting device using the substance.

BACKGROUND ART

A light-emitting element having a layer containing a luminescent substance between a pair of electrodes is used as a pixel, a light source, or the like, and is provided in a light-emitting device such as a display device or a lighting system. When a current flows between a pair of electrodes in a light-emitting element, fluorescence or phosphorescence is emitted from an excited luminescent substance.

In comparison with fluorescence, theoretically, internal quantum efficiency of phosphorescence is three times as high as that of fluorescence in the case of current excitation. Therefore, it is considered that higher emission efficiency is obtained by using a luminescent substance emitting phosphorescence than using a luminescent substance emitting fluorescence; thus, a substance emitting phosphorescence has been developed so far.

For example, a metal complex where a central metal is iridium is mentioned in Non-Patent Document 1. According to the Document, this metal complex can be used as a material for a light-emitting element.

In the case of a light-emitting element that emits light by current excitation, it is insufficient that only a current flows, and it is necessary to recombine electrons and holes effectively. By increasing recombination efficiency of electrons and holes, excitation energy is efficiently generated, and thus, emission efficiency is improved.

So far, it has been widely known and developed that the substance having high internal quantum efficiency is used to increase emission efficiency; however, a substance capable of increasing recombination efficiency has not yet been sufficiently developed.

[Non-Patent Document 1]

"New Iridium Complexes as Highly Efficient Orange-Red Emitters in Organic Light-Emitting Diodes", Jiun-Pey Duan et al., Advanced Materials 2003 15 No. 3, February 5, pp 224-228

DISCLOSURE OF INVENTION

It is an object of the present invention to provide an organometallic complex which can increase recombination efficiency of electrons and holes. It is also an object of the present invention to provide an organometallic complex which can emit phosphorescence and a light-emitting element which has excellent emission efficiency.

One aspect of the present invention is an organometallic complex having a structure represented by a general formula (1).

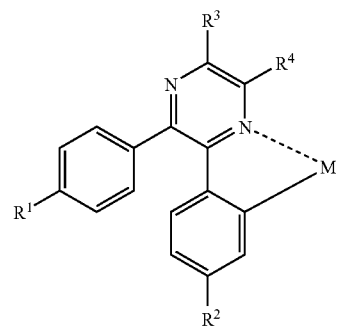

In the general formula (1), each of $R^1$ and $R^2$ is an electron-withdrawing group. In addition, each of $R^3$ and $R^4$ is any of hydrogen and an alkyl group having 1 to 4 carbon atoms. Further, M is an element that belongs to Group 9 or 10 of the periodic table. The electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group. Further, iridium is particularly preferable in the element that belongs to Group 9, and platinum is particularly preferable in the element that belongs to Group 10.

Another aspect of the present invention is an organometallic complex having a structure represented by a general formula (2).

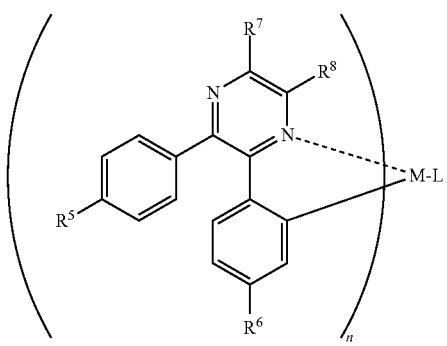

In the general formula (2), each of $R^5$ and $R^6$ is an electron-withdrawing group. In addition, each of $R^7$ and $R^8$ is any of hydrogen and an alkyl group having 1 to 4 carbon atoms. Further, M is an element that belongs to Group 9 or 10 of the periodic table, where n is 2 when M is an element that belongs to Group 9, and n is 1 when M is an element that belongs to Group 10. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group. Further, iridium is particularly preferable in the element that belongs to Group 9, and platinum is particularly preferable in the element that belongs to Group 10.

Another aspect of the present invention is an organometallic complex having a structure represented by a general formula (3).

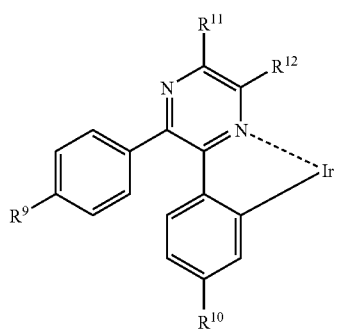

(3)

In the general formula (3), each of $R^9$ and $R^{10}$ is an electron-withdrawing group. In addition, each of $R^{11}$ and $R^{12}$ is any of hydrogen and an alkyl group having 1 to 4 carbon atoms. Here, the electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

Another aspect of the present invention is an organometallic complex having a structure represented by a general formula (4).

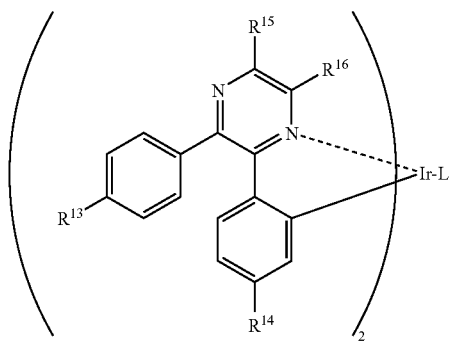

(4)

In the general formula (4), each of $R^{13}$ and $R^{14}$ is an electron-withdrawing group. In addition, each of $R^{15}$ and $R^{16}$ is any of hydrogen and an alkyl group having 1 to 4 carbon atoms. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group, a —$CF_3$ group, a cyano group, and an alkoxycarbonyl group. The alkyl group having 1 to 4 carbon atoms is preferably any of a methyl group, an ethyl group, an isopropyl group, and a sec-butyl group.

Another aspect of the present invention is an organometallic complex having a structure represented by a general formula (5).

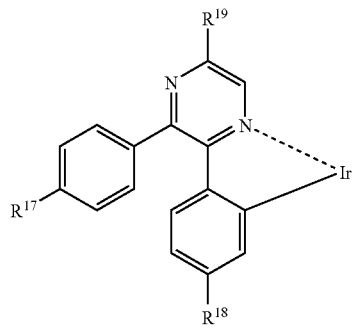

(5)

In the general formula (5), each of $R^{17}$ and $R^{18}$ is an electron-withdrawing group. In addition, $R^{19}$ is any of hydrogen and an alkyl group having 1 to 4 carbon atoms. Here, the electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

Another aspect of the present invention is an organometallic complex having a structure represented by a general formula (6).

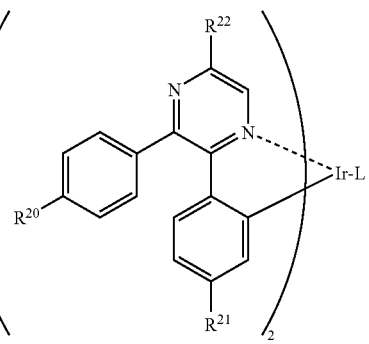

(6)

In the general formula (6), each of $R^{20}$ and $R^{21}$ is an electron-withdrawing group. In addition, $R^{22}$ is any of hydrogen and an alkyl group having 1 to 4 carbon atoms. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

In the organometallic complexes represented by the general formulas (2), (4) and (6), specifically, L is preferably a ligand selected from ligands represented by the following structural formulas (1) to (7). The ligands represented by the structural formulas (1) to (7) are all monoanionic ligands.

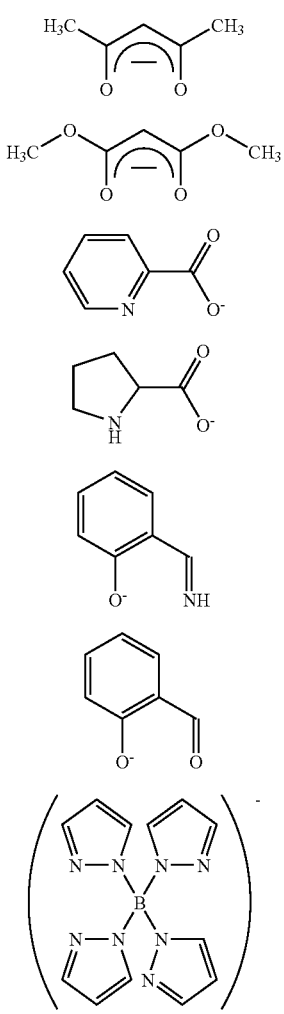

Another aspect of the present invention is an organometallic complex having a structure represented by a general formula (7).

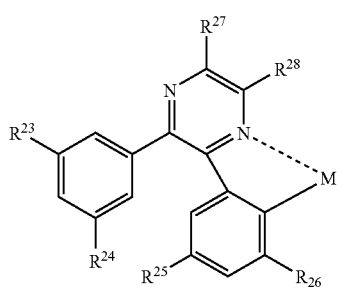

In the general formula (7), each of $R^{23}$ to $R^{26}$ is an electron-withdrawing group. In addition, each of $R^{27}$ and $R^{28}$ is any of hydrogen and an alkyl group having 1 to 4 carbon atoms. Further, M is an element that belongs to Group 9 or 10 of the periodic table. Here, the electron-withdrawing group is preferably any of a halogen group, a —$CF_3$ group, a cyano group, and an alkoxycarbonyl group. A fluoro group is particularly preferable in the halogen group since chemical stability is favorable. Further, iridium is particularly preferable in the element that belongs to Group 9, and platinum is particularly preferable in the element that belongs to Group 10.

Another aspect of the present invention is an organometallic complex having a structure represented by a general formula (8).

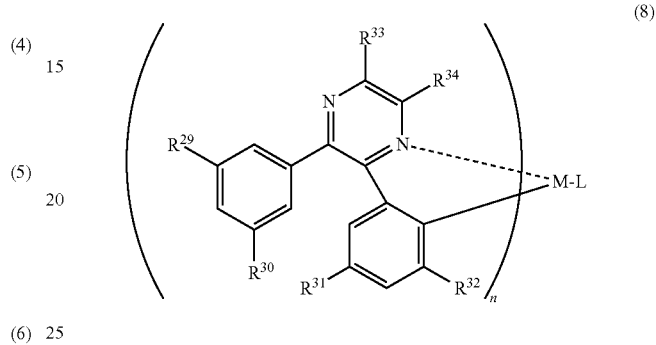

In the general formula (8), each of $R^{29}$ to $R^{32}$ is an electron-withdrawing group. In addition, each of $R^{33}$ and $R^{34}$ is any of hydrogen and an alkyl group having 1 to 4 carbon atoms. Further, M is an element that belongs to Group 9 or 10 of the periodic table, where n is 2 when M is an element that belongs to Group 9, and n is 1 when M is an element that belongs to Group 10. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group, a —$CF_3$ group, a cyano group, and an alkoxycarbonyl group. A fluoro group is particularly preferable in the halogen group since chemical stability is favorable. Further, iridium is particularly preferable in the element that belongs to Group 9, and platinum is particularly preferable in the element that belongs to Group 10.

Another aspect of the present invention is an organometallic complex having a structure represented by a general formula (9).

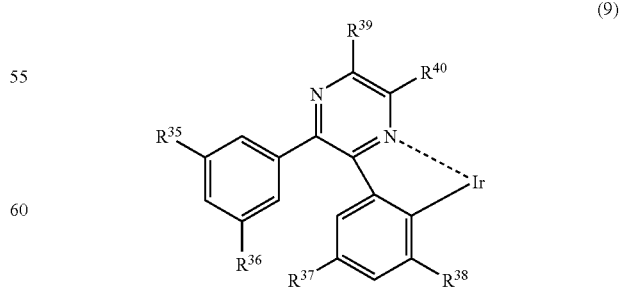

In the general formula (9), each of $R^{35}$ to $R^{38}$ is an electron-withdrawing group. In addition, each of $R^{39}$ and $R^{40}$ is any of hydrogen and an alkyl group having 1 to 4 carbon atoms.

Here, the electron-withdrawing group is preferably any of a halogen group, a —$CF_3$ group, a cyano group, and an alkoxycarbonyl group. A fluoro group is particularly preferable in the halogen group since chemical stability is favorable.

Another aspect of the present invention is an organometallic complex having a structure represented by a general formula (10).

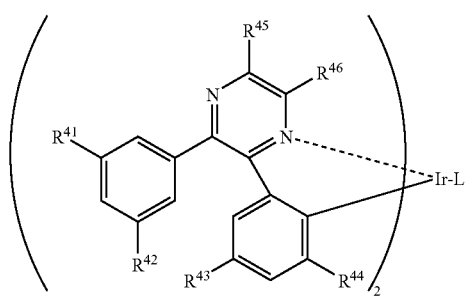
(10)

In the general formula (10), each of $R^{41}$ to $R^{44}$ is an electron-withdrawing group. In addition, each of $R^{45}$ and $R^{46}$ is any of hydrogen and an alkyl group having 1 to 4 carbon atoms. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group, a —$CF_3$ group, a cyano group, and an alkoxycarbonyl group. A fluoro group is particularly preferable in the halogen group since chemical stability is favorable.

Another aspect of the present invention is an organometallic complex having a structure represented by a general formula (11).

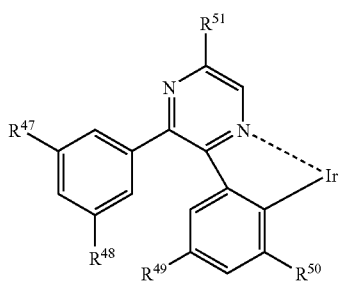
(11)

In the general formula (11), each of $R^{47}$ to $R^{50}$ is an electron-withdrawing group. In addition, $R^{51}$ is any of hydrogen and an alkyl group having 1 to 4 carbon atoms. Here, the electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

Another aspect of the present invention is an organometallic complex having a structure represented by a general formula (12).

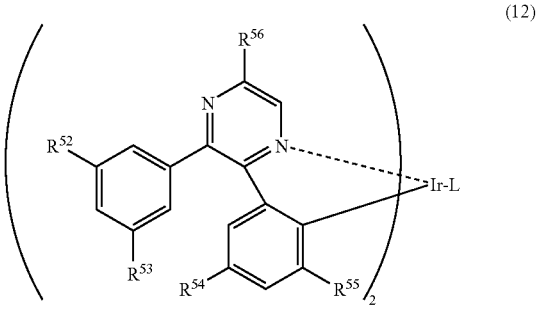
(12)

In the general formula (12), each of $R^{52}$ to $R^{55}$ is an electron-withdrawing group. In addition, $R^{56}$ is any of hydrogen and an alkyl group having 1 to 4 carbon atoms. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group, a —$CF_3$ group, a cyano group, and an alkoxycarbonyl group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

In the organometallic complexes represented by the general formulas (8), (10) and (12), specifically, L is preferably a ligand selected from ligands represented by the following structural formulas (1) to (7). The ligands represented by the structural formulas (1) to (7) are all monoanionic ligands.

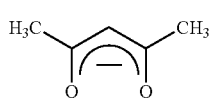
(1)

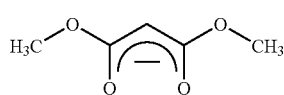
(2)

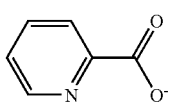
(3)

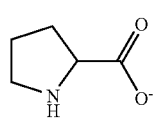
(4)

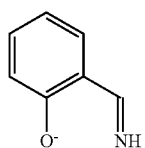
(5)

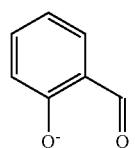
(6)

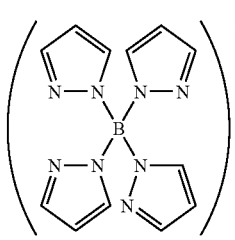
(7)

Another aspect of the present invention is an organometallic complex having a structure represented by a general formula (13).

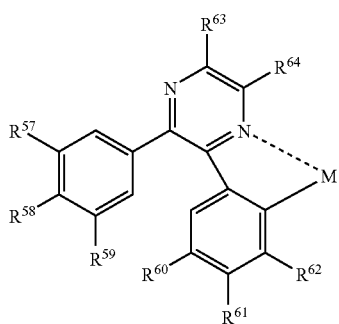
(13)

In the general formula (13), each of $R^{57}$ to $R^{62}$ is an electron-withdrawing group. In addition, each of $R^{63}$ and $R^{64}$ is any of hydrogen and an alkyl group having 1 to 4 carbon atoms. Further, M is an element that belongs to Group 9 or 10 of the periodic table. Here, the electron-withdrawing group is preferably any of a halogen group and a —$CF_3$ group. A fluoro group is particularly preferable in the halogen group since chemical stability is favorable. Further, iridium is particularly preferable in the element that belongs to Group 9, and platinum is particularly preferable in the element that belongs to Group 10. The alkyl group having 1 to 4 carbon atoms is preferably any of a methyl group, an ethyl group, an isopropyl group, and a sec-butyl group.

Another aspect of the present invention is an organometallic complex having a structure represented by a general formula (14).

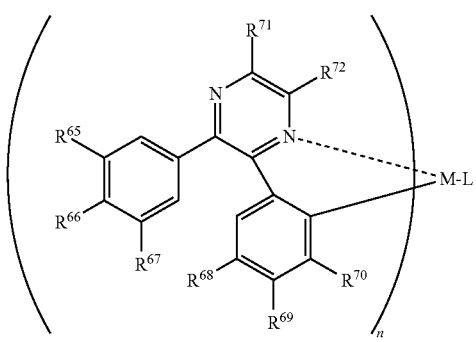
(14)

In the general formula (14), each of $R^{65}$ to $R^{70}$ is an electron-withdrawing group. In addition, each of $R^{71}$ and $R^{72}$ is any of hydrogen and an alkyl group having 1 to 4 carbon atoms. Further, M is an element that belongs to Group 9 or 10 of the periodic table, where n is 2 when M is an element that belongs to Group 9, and n is 1 when M is an element that belongs to Group 10. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group and a —$CF_3$ group. A fluoro group is particularly preferable in the halogen group since chemical stability is favorable. Further, iridium is particularly preferable in the element that belongs to Group 9, and platinum is particularly preferable in the element that belongs to Group 10. The alkyl group having 1 to 4 carbon atoms is preferably any of a methyl group, an ethyl group, an isopropyl group, and a sec-butyl group.

Another aspect of the present invention is an organometallic complex having a structure represented by a general formula (15).

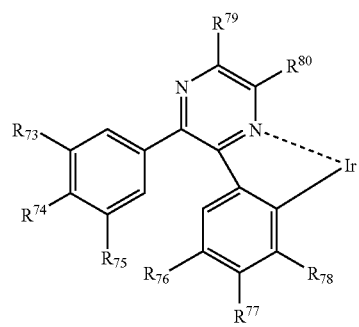
(15)

In the general formula (15), each of $R^{73}$ to $R^{78}$ is an electron-withdrawing group. In addition, each of $R^{79}$ and $R^{80}$ is any of hydrogen and an alkyl group having 1 to 4 carbon atoms. Here, the electron-withdrawing group is preferably any of a halogen group and a —$CF_3$ group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

Another aspect of the present invention is an organometallic complex having a structure represented by a general formula (16).

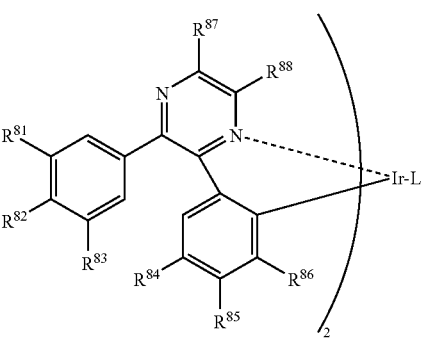
(16)

In the general formula (16), each of $R^{81}$ to $R^{86}$ is an electron-withdrawing group. In addition, each of $R^{87}$ and $R^{88}$ is any of hydrogen and an alkyl group having 1 to 4 carbon atoms. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group and a —CF$_3$ group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

Another aspect of the present invention is an organometallic complex having a structure represented by a general formula (17).

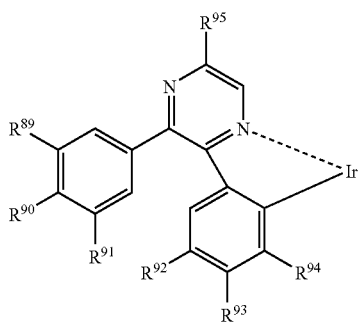

(17)

In the general formula (17), each of $R^{89}$ to $R^{94}$ is an electron-withdrawing group. In addition, $R^{95}$ is any of hydrogen and an alkyl group having 1 to 4 carbon atoms. Here, the electron-withdrawing group is preferably any of a halogen group and a —CF$_3$ group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

Another aspect of the present invention is an organometallic complex having a structure represented by a general formula (18).

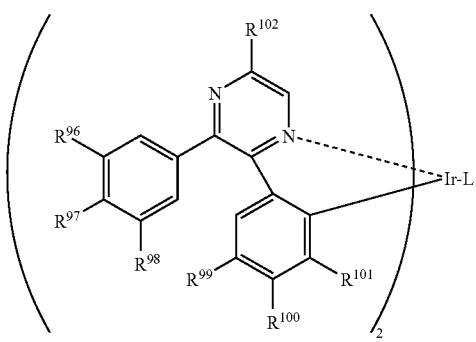

(18)

In the general formula (18), each of $R^{96}$ to $R^{101}$ is an electron-withdrawing group. In addition, $R^{102}$ is any of hydrogen and an alkyl group having 1 to 4 carbon atoms. L is any of a monoanionic ligand having a β-diketone structure, a monoanionic bidentate-chelate ligand having a carboxyl group, and a monoanionic bidentate-chelate ligand having a phenolic hydroxyl group. Here, the electron-withdrawing group is preferably any of a halogen group and a —CF$_3$ group. A fluoro group is particularly preferable in the halogen group since chemical stability is favorable. The alkyl group having 1 to 4 carbon atoms is preferably any of a methyl group, an ethyl group, an isopropyl group, and a sec-butyl group.

In the organometallic complexes represented by the general formulas (14), (16) and (18), specifically, L is preferably a ligand selected from ligands represented by the following structural formulas (1) to (7). The ligands represented by the structural formulas (1) to (7) are all monoanionic ligands.

(1)

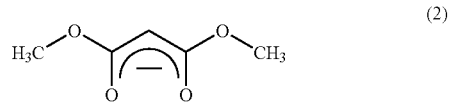

(2)

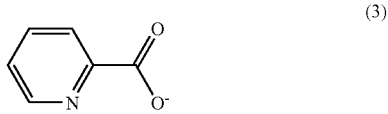

(3)

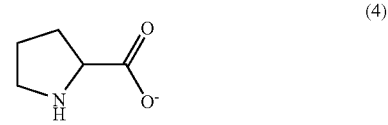

(4)

(5)

(6)

(7)

Another aspect of the present invention is a light-emitting element including the organometallic complex represented by any of the general formulas (1) to (18). The light-emitting element preferably has a structure in which a layer containing the organometallic complex represented by any of the general formulas (1) to (18) is provided between electrodes and the organometallic complex represented by any of the general formulas (1) to (18) emits light when a current flows between the electrodes. The light-emitting element using the organometallic complex according to the present invention as a luminescent substance as described above has high recombination efficiency and emits light efficiently.

Another aspect of the present invention is a light-emitting device utilizing the light-emitting element, which includes the organometallic complex represented by any of the general formulas (1) to (18), as a pixel or a light source. Since the light-emitting element according to the present invention emits light efficiently, a light-emitting device which can drive with low power consumption can be obtained by using the light-emitting element according to the present invention.

By implementing the present invention, an organometallic complex can be obtained, which can be used for manufacturing a light-emitting element having high recombination efficiency. In addition, by the present invention, an organometallic complex can be obtained, which can be used for manufacturing a light-emitting element capable of emitting phosphorescence efficiently.

One aspect of the present invention is an organometallic complex, in particular, in which each of $R^5$ and $R^6$ is a fluoro group, $R^3$ is hydrogen or a methyl group, $R^8$ is hydrogen, and M is iridium (Ir) where n is 2, among the organometallic complexes represented by the general formula (1). A ligand is preferably any of an acetylacetonate ligand, a tetrakis(1-pyrazolyl)borate ligand, and a picolinate ligand.

By the present invention, a light-emitting element having high recombination efficiency and emitting light efficiently can be obtained. Further, a light-emitting element capable of emitting phosphorescence and having high internal quantum efficiency can be obtained. In addition, a light-emitting element can be obtained, in which luminescence and recombination are repeated efficiently even in a high-luminance region.

By implementing the present invention, a light-emitting device which can emit light efficiently and drive with low power consumption can be obtained.

BEST MODE FOR CARRYING OUT THE INVENTION

Figure 1:
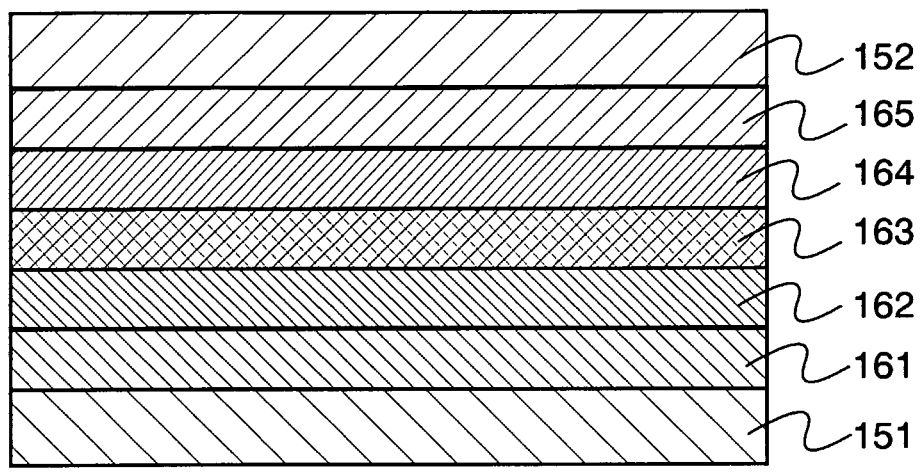
FIG. 1 is a view explaining an example of a light-emitting device according to the present invention.

Embodiment Modes of the present invention will hereinafter be described. It is to be noted that the present invention can be implemented in various modes, and it is to be easily understood by those skilled in the art that various changes and modifications in modes and details thereof are possible without departing from the spirit and the scope of the invention. Therefore, the present invention should not be interpreted as being limited to the description of the embodiment modes to be given below.

[Embodiment Mode 1]

Organometallic complexes represented by structural formulas (8) to (55) can be given as examples of the present invention; however, the invention is not limited to the descriptions here.

(8)

(9)

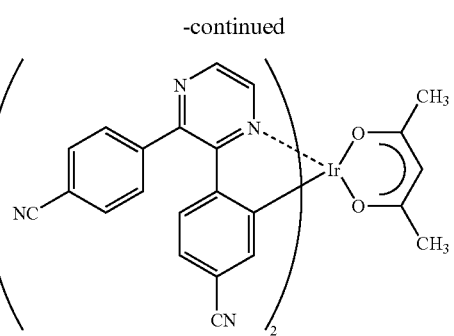

(10)

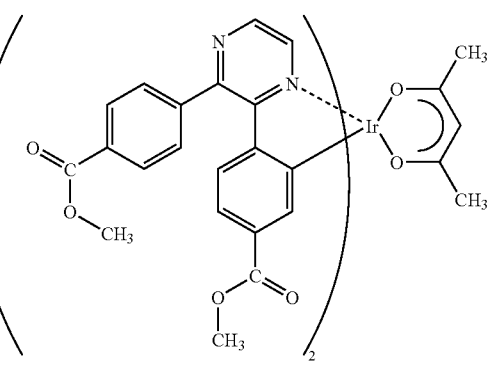

(11)

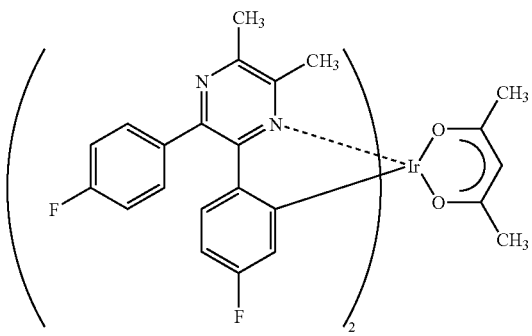

(12)

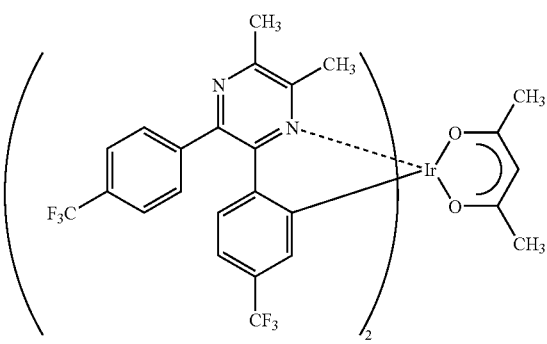

(13)

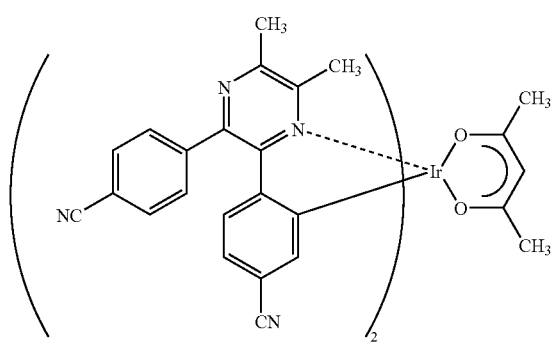
(14)
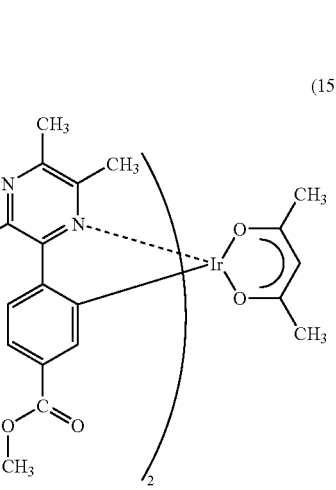
(15)
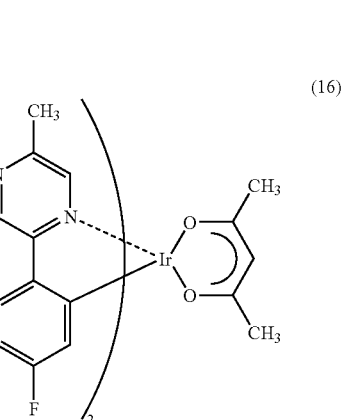
(16)
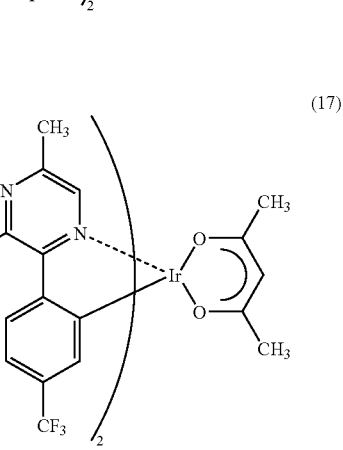
(17)
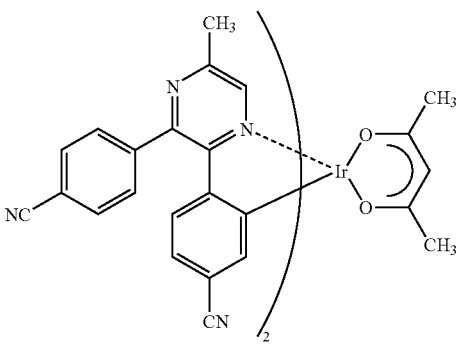
(18)
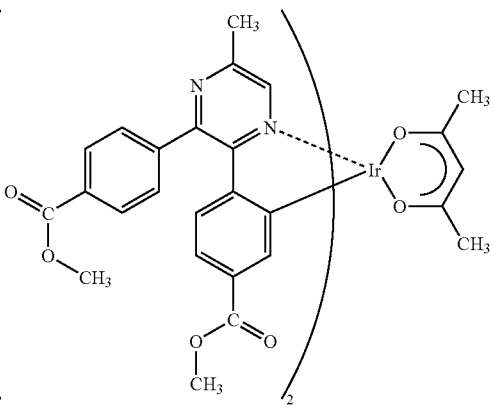
(19)
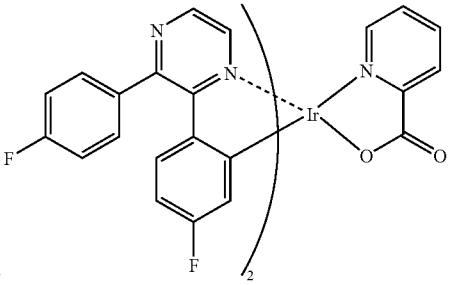
(20)
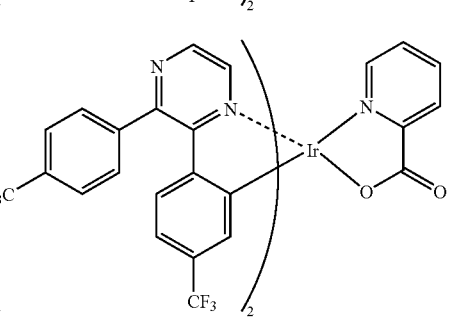
(21)
(22)

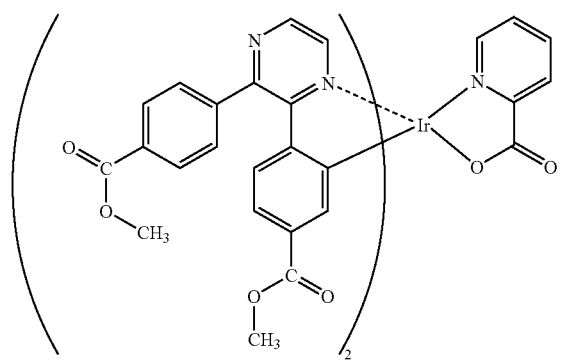
(23)
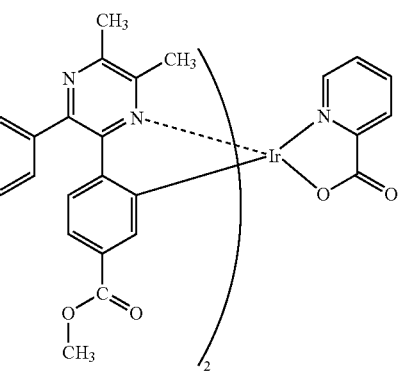
(27)
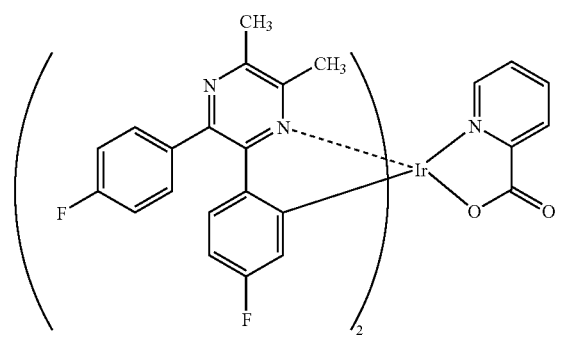
(24)
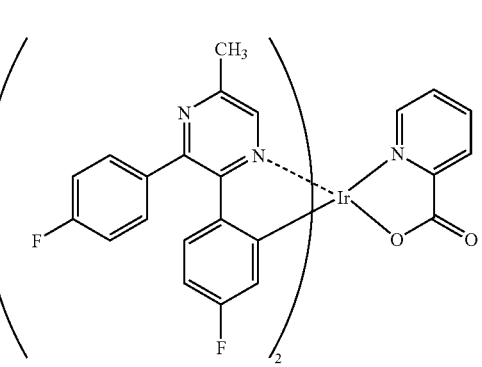
(28)
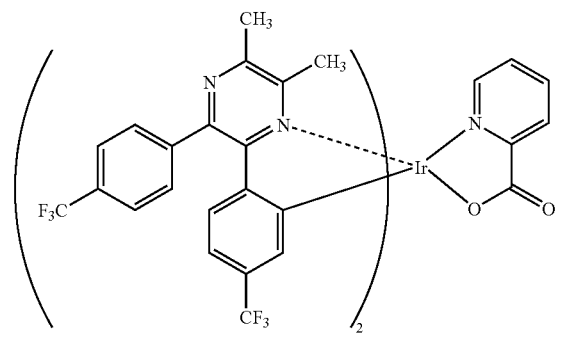
(25)
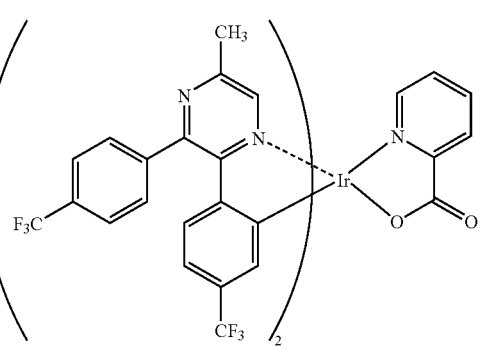
(29)
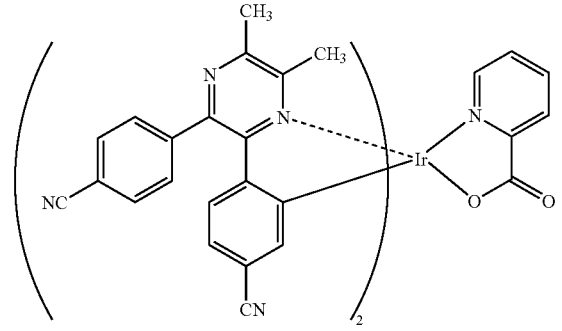
(26)
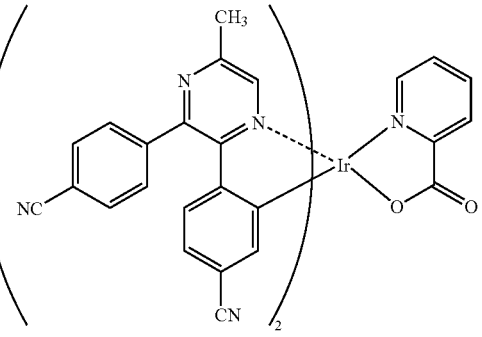
(30)

(31)
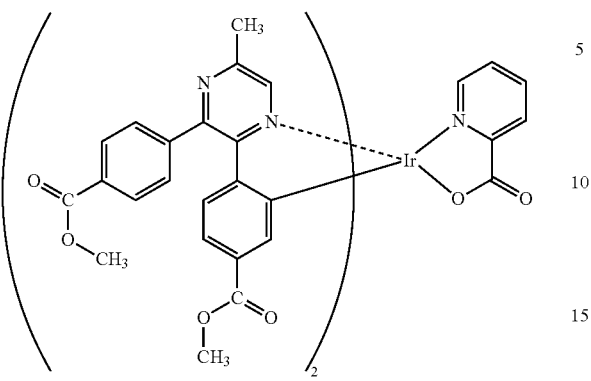
(32)
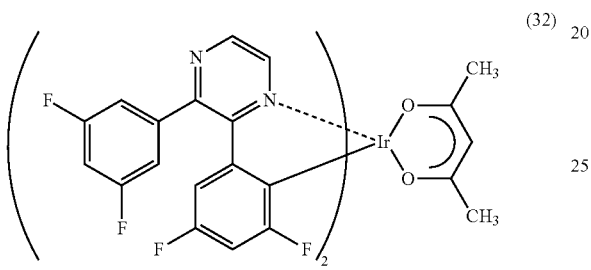
(33)
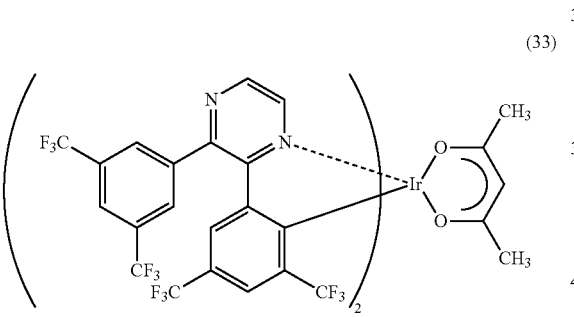
(34)
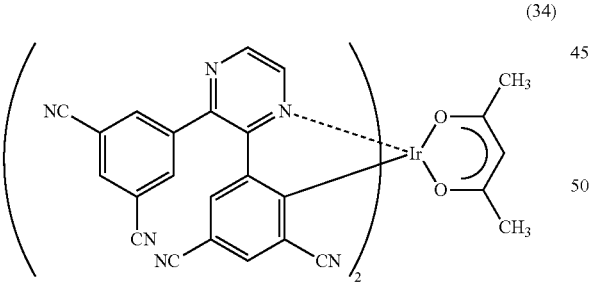
(35)
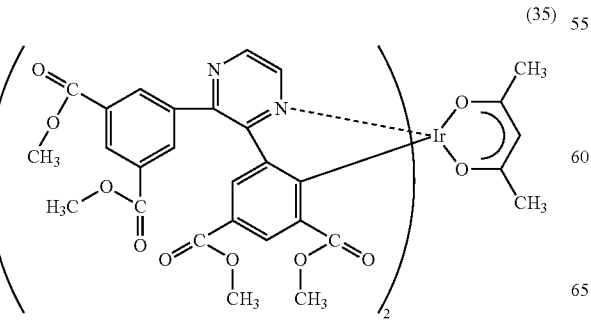
(36)
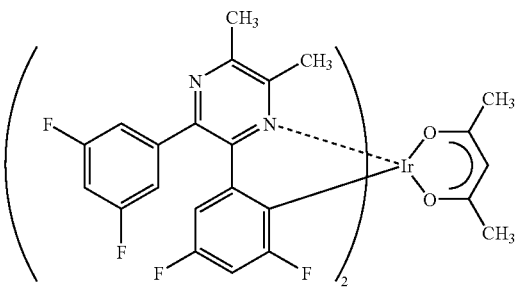
(37)
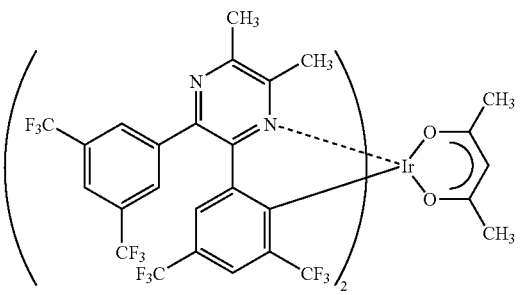
(38)
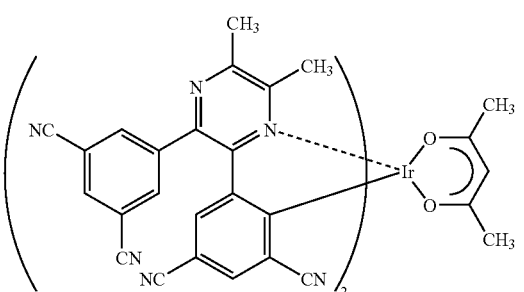
(39)
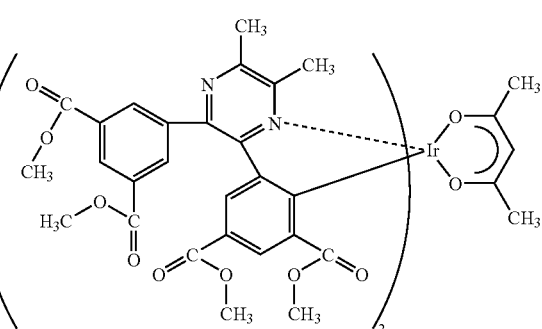
(40)
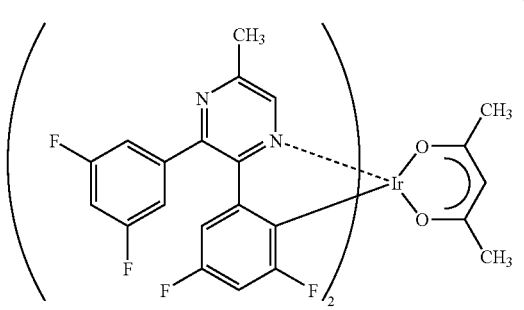

(41) 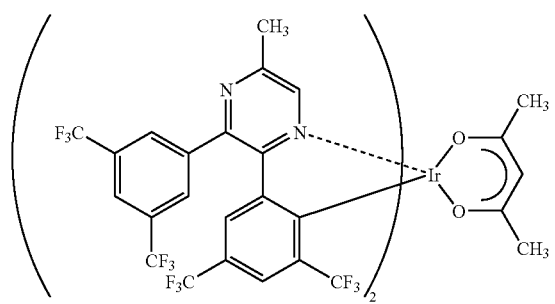
(42) 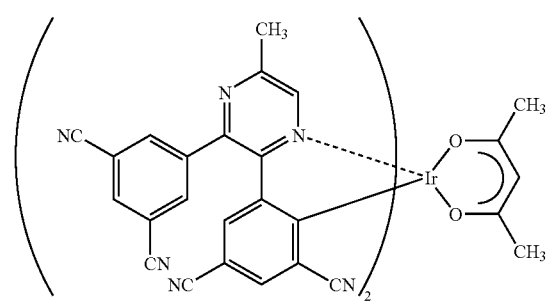
(43) 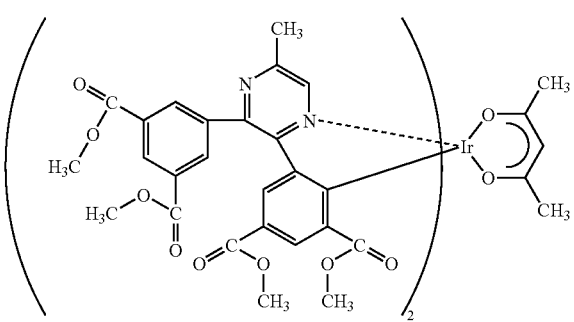
(44) 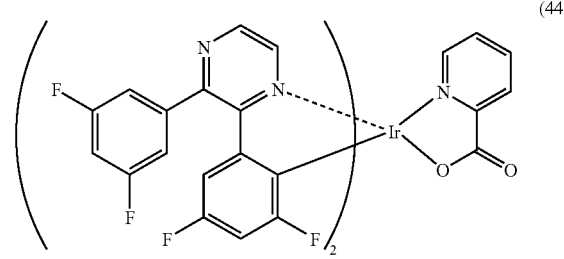
(45) 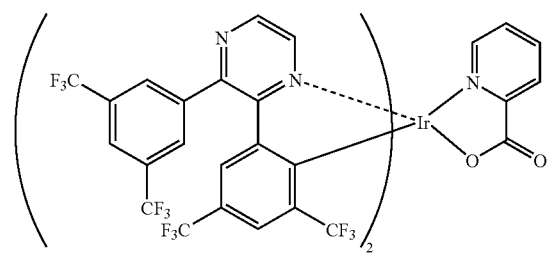
(46) 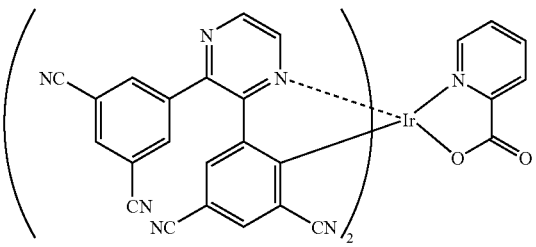
(47) 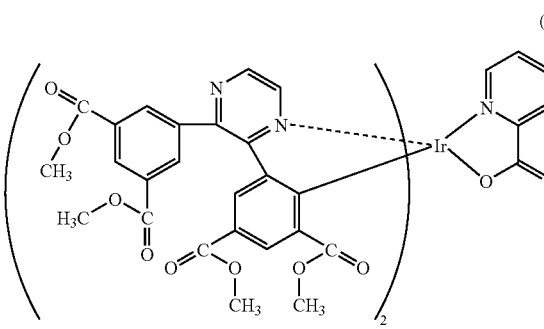
(48) 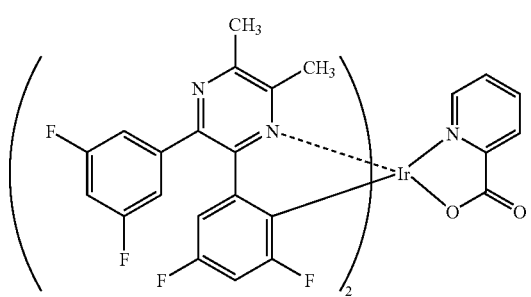
(49) 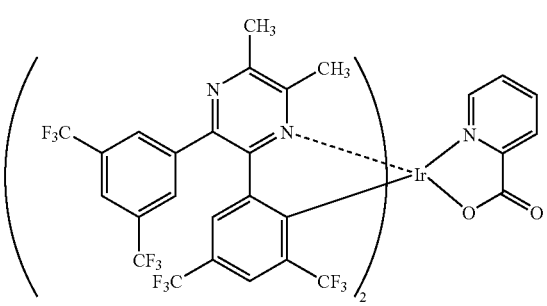

(50)
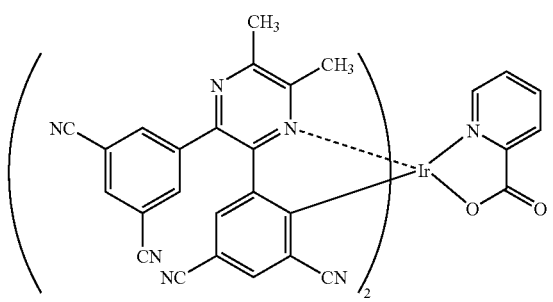

(54)
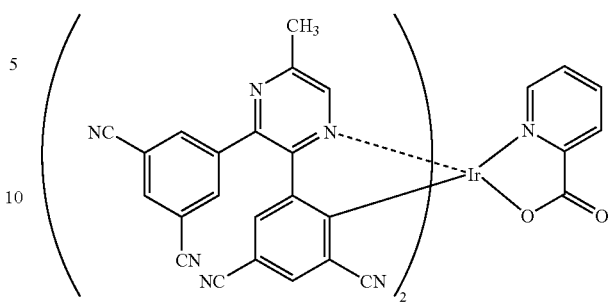

(51)
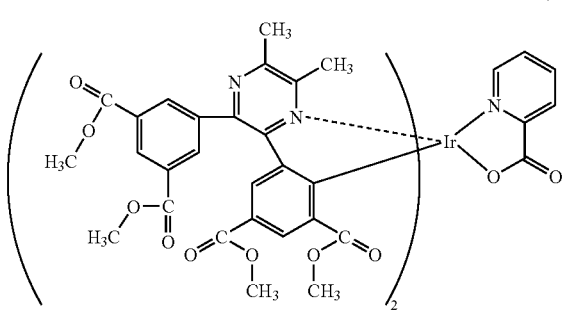

(55)
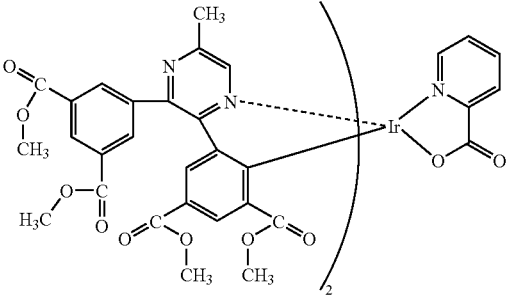

(52)
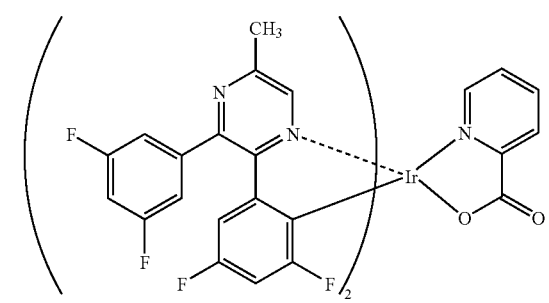

The organometallic complex according to the present invention as described above can easily capture electrons. It is thought that this is because an electron-withdrawing group is introduced into a ligand by the present invention. In addition, since the organometallic complex can easily capture electrons, a light-emitting element, which has enhanced carrier-recombination efficiency and emits light efficiently, can be manufactured by using the organometallic complex according to the present invention. Further, by using the organometallic complex, a light-emitting element can be manufactured, in which excitation and luminescence can be repeated efficiently even in luminescence at high luminance. This is because, by using the organometallic complex according to the present invention, non-emitting transition due to an excitation lifetime of a triplet excitation state or the like is not easily increased.

The organometallic complex according to the present invention represented by any of the structural formulas (8) to (31) can be obtained by a synthesis method as shown in synthetic schemes (a-1) to (a-3) that will be described below. As shown in the synthetic scheme (a-1), a ligand containing an electron-withdrawing group is synthesized. Then, the synthesized ligand containing an electron-withdrawing group is mixed with iridium (III) chloride hydrochloride hydrate and coordinated with iridium as shown in the synthesis scheme (a-2). Further, as shown in the synthesis scheme (a-3), a monoanionic ligand is coordinated with iridium.

(53)
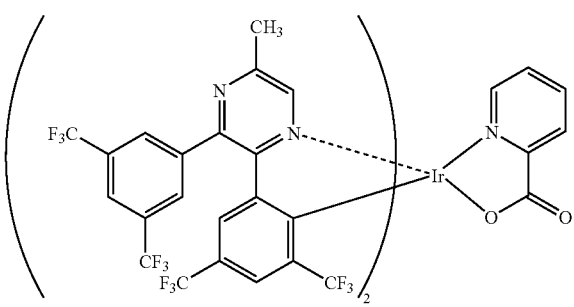

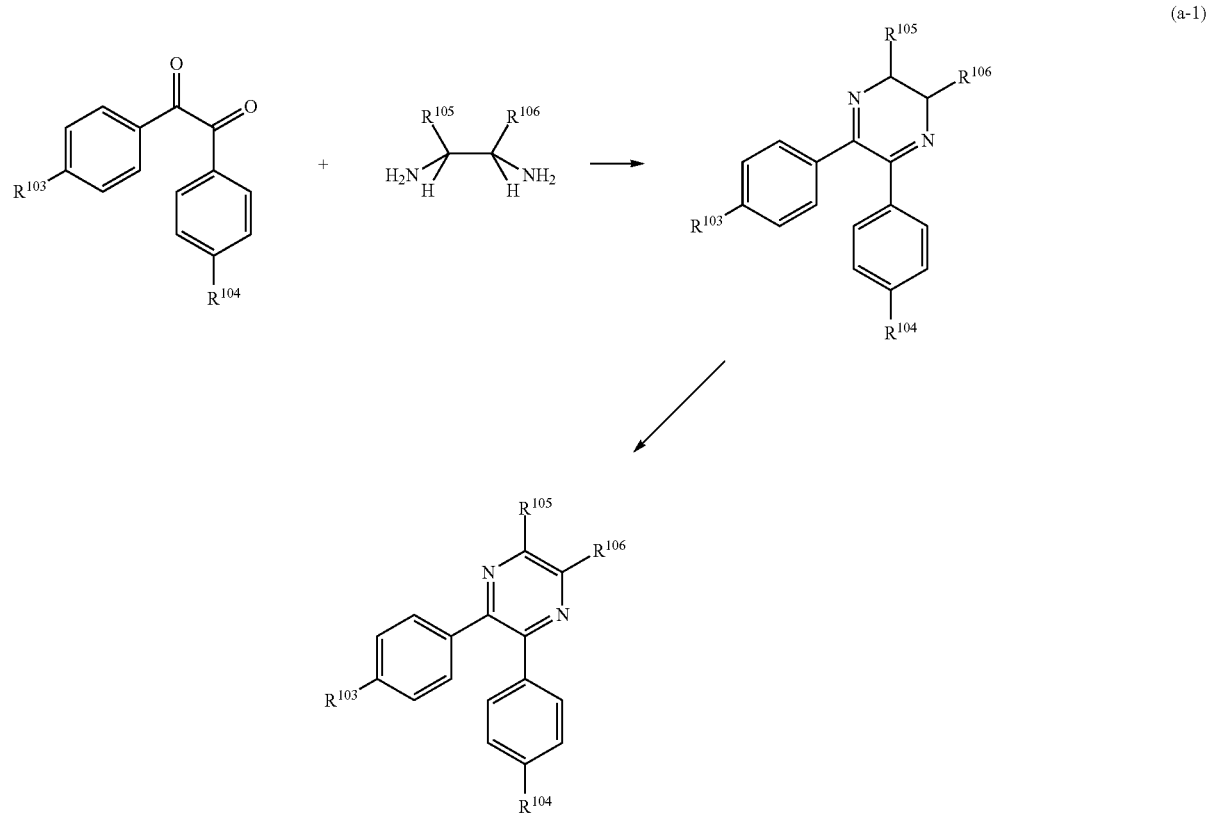
(a-1)
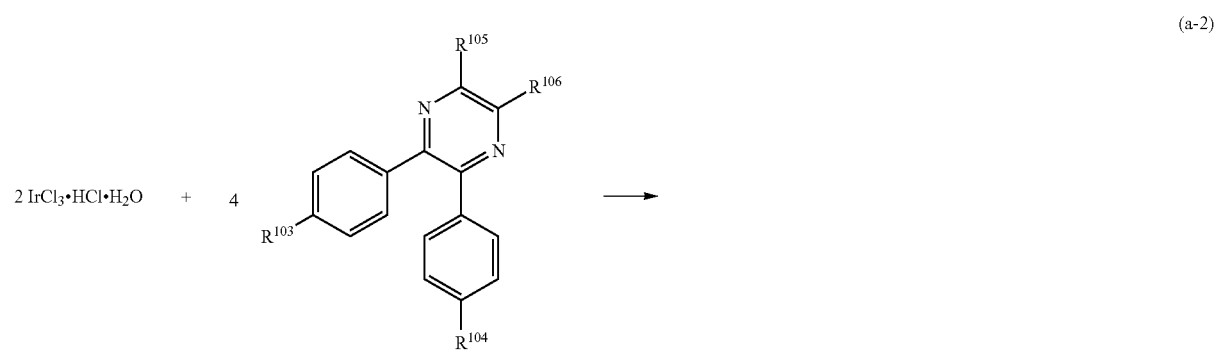
(a-2)
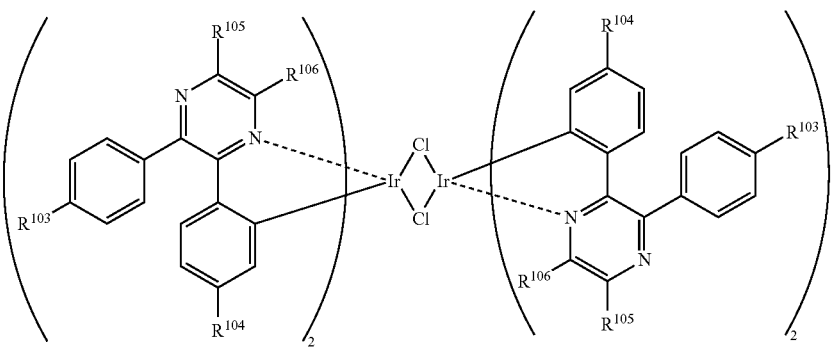

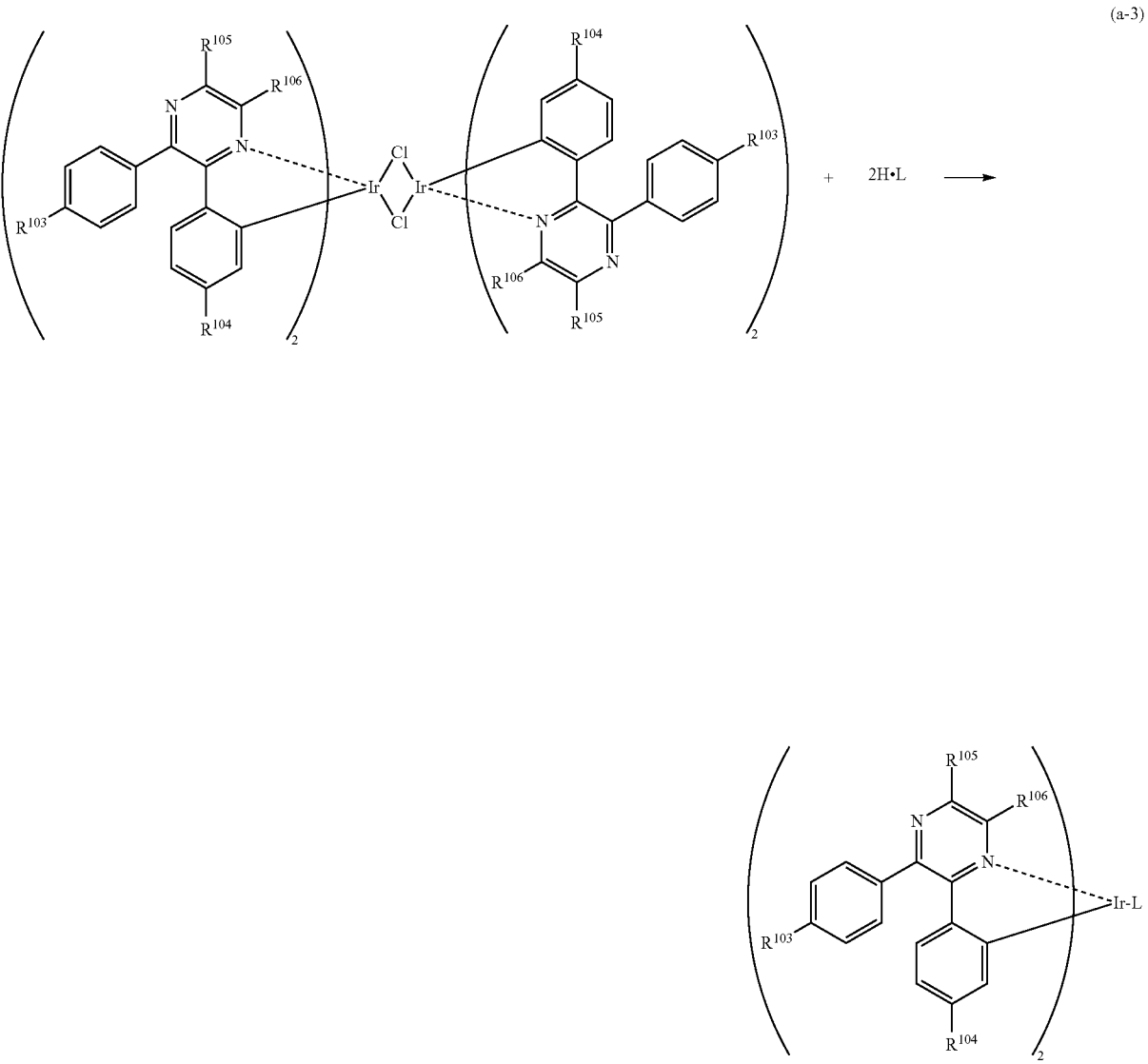

(a-3)

Here, in the synthesis schemes (a-1) to (a-3), each of $R^{103}$ and $R^{104}$ is any of a fluoro group, a —$CF^3$ group, a cyano group, and an alkoxycarbonyl group. In addition, each of $R^{105}$ and $R^{106}$ is hydrogen or a methyl group. Further, L is acetylacetone or picolinic acid.

It is to be noted that a synthesis method of an organometallic complex according to the present invention is not limited to the one shown by the synthesis schemes (a-1) to (a-3). For example, as for a ligand obtained in the synthesis scheme (a-1), a ligand in which both of $R^{105}$ and $R^{106}$ are substituted by an alkyl group can be obtained as follows: 2,3-diphenyl-1,4-dihydropyrazine-5,6-dione in which a para position of a phenyl group is substituted by an electron-withdrawing group is used as a material, a dichlorinated compound in which 5 and 6 positions are chlorinated is formed by using $POCl_3$ and the like, and the obtained dichlorinated compound and an alkyl metal are coupled. In addition, by using salt containing platinum such as tetrachloroplatinate potassium instead of iridium (III) chloride hydrochloride hydrate, an organometallic complex according to the present invention containing platinum as a central metal can be obtained. Further, by using a ligand such as dimethyl malonate, salicylaldehyde, salicylideneamine, or tetrapyrazolato boronate instead of acetylacetone or picolinic acid, the organometallic complex according to the present invention containing a ligand represented by the structural formulas (2), (4) to (7) can be obtained.

The organometallic complex according to the present invention represented by any of the structural formulas (32) to (55) can be obtained by a synthesis method as shown in synthesis schemes (b-1) to (b-3). As shown in the synthesis scheme (b-1), a ligand containing an electron-withdrawing group is synthesized. Then, the synthesized ligand containing an electron-withdrawing group is mixed with iridium (III) chloride hydrochloride hydrate and coordinated with iridium as shown in the synthesis scheme (b-2). Further, as shown in the synthesis scheme (b-3), a monoanionic ligand is coordinated with iridium.

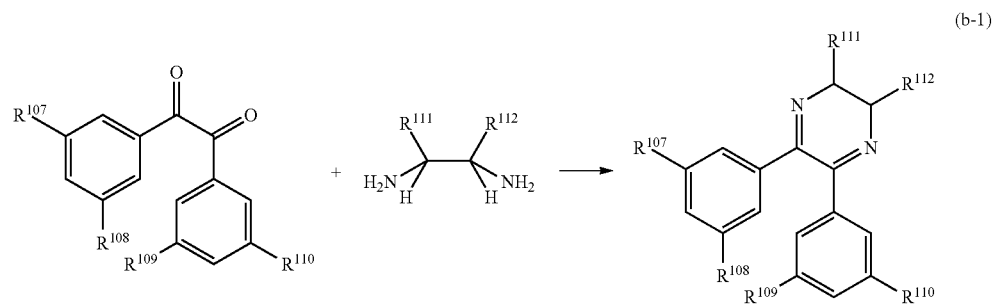
(b-1)
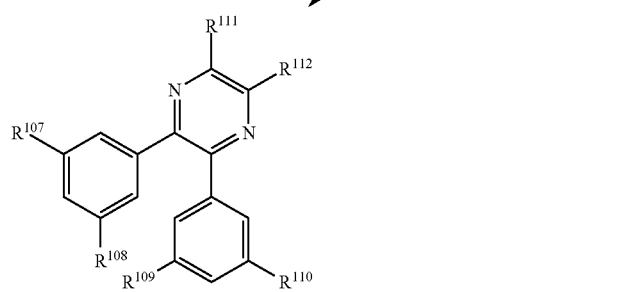
(b-2)
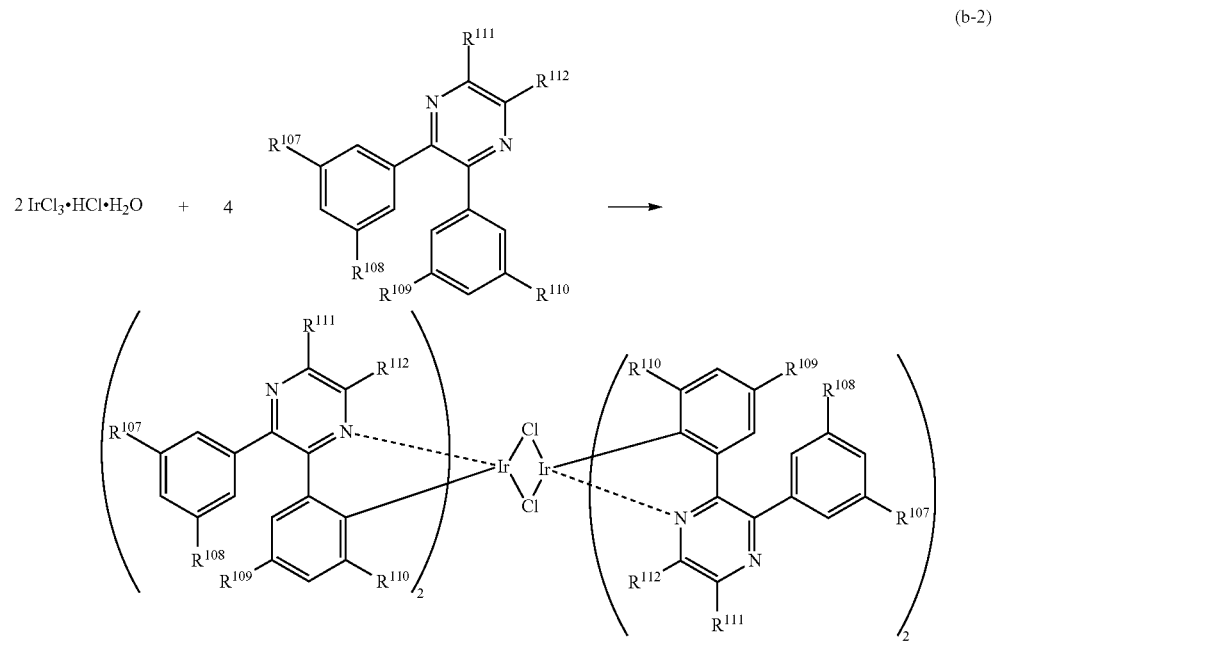
(b-3)
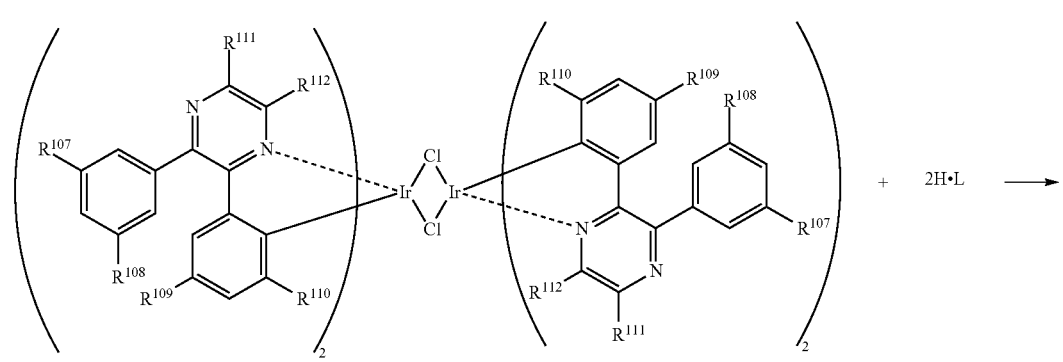

-continued

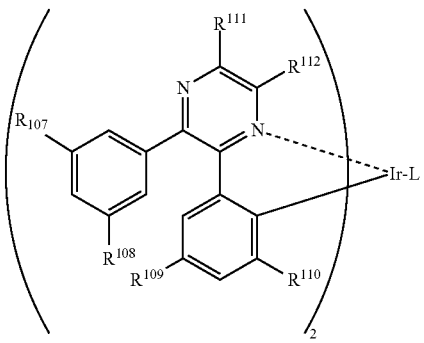

Here, in the synthesis schemes (b-1) to (b-3), each of $R^{107}$ to $R^{110}$ is any of a fluoro group, a —$CF_3$ group, a cyano group, and an alkoxycarbonyl group. In addition, each of $R^{111}$ and $R^{112}$ is hydrogen or a methyl group. Further, L is acetylacetone or picolinic acid. Diketone that is used in reaction of the synthesis scheme (b-1) can be obtained by reacting Grignard reagent of benzene, in which 3 and 5 positions are substituted by an electron-withdrawing group such as a fluoro group or a —$CF_3$ group, with 1,4-dimethylpiperazine-2,3-dione.

It is to be noted that a synthesis method of an organometallic complex according to the present invention is not limited to the one shown by the synthesis schemes (b-1) to (b-3). By using salt containing platinum such as tetrachloroplatinate potassium instead of iridium (III) chloride hydrochloride hydrate, an organometallic complex according to the present invention containing platinum as a central metal can be obtained. Further, by using a ligand such as dimethyl malonate, salicylaldehyde, salicylideneamine, or tetrapyrazolato boronate instead of acetylacetone or picolinic acid, the organometallic complex according to the present invention containing a ligand represented by the structural formulas (2), (4) to (7) can be obtained.

[Embodiment Mode 2]

An example of a light-emitting element using the organometallic complex according to the present invention as a luminescent substance will be described with reference to FIG. 1.

FIG. 1 shows a light-emitting element including a light-emitting layer 163 between a first electrode 151 and a second electrode 152. The light-emitting layer 163 contains an organometallic complex according to the present invention having a structure represented by any of general formulas (1), (3), (5), (7), (9), (11), (13), (15), and (17), or an organometallic complex according to the present invention having a structure represented by any of the general formulas (2), (4), (6), (8), (10), (12), (14), (16), and (18).

Between the first electrode 151 and the second electrode 152, a hole-injecting layer 161, a hole-transporting layer 162, an electron-transporting layer 164, an electron-injecting layer 165, and the like are provided in addition to the light-emitting layer 163. These layers are stacked so that holes are injected from the first electrode 151 side and electrons are injected from the second electrode 152 side when a voltage is applied to make electric potential of the first electrode 151 higher than that of the second electrode 152.

In such a light-emitting element, holes injected from the first electrode 151 side and electrons injected from the second electrode 152 side are recombined in the light-emitting layer 163, and the organometallic complex is to be in an excited state. The excited organometallic complex emits light when it returns to a ground state. In this manner, the organometallic complex according to the present invention serves as a luminescent substance. Since the organometallic complex according to the present invention has a property to capture electrons easily, carriers are recombined efficiently. Accordingly, the light-emitting element according to the present invention containing the organometallic complex as described above emits light efficiently.

Here, the light-emitting layer 163 is a layer containing the organometallic complex according to the present invention. The light-emitting layer 163 may be a layer formed only of the organometallic complex according to the present invention. However, in the case where concentration quenching occurs, the light-emitting layer 163 is preferably a layer in which a luminescent substance is mixed to be dispersed in a layer formed of a substance having an energy gap larger than that of a luminescent substance. By the organometallic complex according to the present invention contained to be dispersed in the light-emitting layer 163, light emission can be prevented from being quenched due to concentration. Here, the energy gap indicates an energy gap between the LUMO level and the HOMO level.

A substance used for dispersing the organometallic complex according to the present invention is not particularly limited, and a carbazole derivative such as 4,4'-di(N-carbazolyl)biphenyl (abbreviation: CBP) or 4,4',4''-tri(N-carbazolyl)triphenylamine (abbreviation: TCTA); a metal complex such as bis[2-(2-hydroxyphenyl)pyridinato]zinc (abbreviation: $Znpp_2$), bis[2-(2-hydroxyphenyl)benzoxazolate]zinc (abbreviation: $Zn(BOX)_2$); or the like is preferable in addition to a compound having an arylamine skeleton such as 2,3-bis (4-diphenylaminophenyl)quinoxaline (abbreviation: TPAQn) or 4,4'-bis[N-(1-naphthyl)-N-phenylamino]biphenyl (abbreviation: NPB). One or two or more of these substances are selected to be mixed so that the organometallic complex according to the present invention is in a dispersed state. A layer containing a plurality of compounds can be formed with the use of co-evaporation. Here, co-evaporation refers to an evaporation method in which raw materials are respectively vaporized from a plurality of evaporation sources provided in one treatment chamber, and the vaporized materials are mixed in a gas-phase state to be deposited over a subject.

In addition, the first electrode 151 and the second electrode 152 are not particularly limited and can be formed by using gold (Au), platinum (Pt), nickel (Ni), tungsten (W), chromium (Cr), molybdenum (Mo), iron (Fe), cobalt (Co), copper (Cu), palladium (Pd), or the like in addition to indium tin oxide (ITO), indium tin oxide containing silicon oxide, or indium oxide containing 2 to 20% of zinc oxide. Moreover, in addition to aluminum, an alloy of magnesium and silver, an alloy of aluminum and lithium, or the like can also be used to form the first electrode 151. It is to be noted that a method for forming the first electrode 151 and the second electrode 152 is not particularly limited and, for example, sputtering, evaporation, or the like can be used. It is preferable to form one or both of the first electrode 151 and the second electrode 152 by using indium tin oxide or the like or by depositing silver, aluminum, or the like to have a thickness of several nm to several 10 nm so that emitted light can be extracted outside.

Moreover, the hole-transporting layer 162 may be provided between the first electrode 151 and the light-emitting layer 163 as shown in FIG. 1. Here, the hole-transporting layer 162 is a layer having a function of transporting holes injected from the first electrode 151 side to the light-emitting layer 163. By providing the hole-transporting layer 162, the distance between the first electrode 151 and the light-emitting layer 163 can be longer. Consequently, light emission can be prevented from being quenched due to a metal contained in the first electrode 151. The hole-transporting layer 162 is preferably formed by using a substance having a high hole-transporting property, and in particular, it is preferably formed by using a substance having hole mobility of $1\times10^{-6}$ cm$^2$/Vs or more. It is to be noted that the substance having a high hole-transporting property indicates a substance having higher mobility of holes than that of electrons, where the value of a ratio of hole mobility to electron mobility (=hole mobility/electron mobility) is more than 100. The following can be given as a specific example of a substance that can be used to form the hole-transporting layer 162: 4,4'-bis[N-(1-naphtyl)-N-phenylamino]biphenyl (abbreviation: NPB); 4,4'-bis[N-(3-methylphenyl)-N-phenylamino]biphenyl (abbreviation: TPD); 4,4',4''-tris(N,N-diphenylamino)triphenylamine (abbreviation: TDATA); 4,4',4''-tris[N-(3-methylphenyl)-N-phenylamino]triphenylamine (abbreviation: MTDATA); 4,4'-bis{N-[4-(N,N-di-m-tolylamino)phenyl]-N-phenylamino}biphenyl (abbreviation: DNTPD); 1,3,5-tris[N,N-di(m-tolyl)amino]benzene (abbreviation: m-MTDAB); 4,4',4''-tri(N-carbazolyl)triphenylamine (abbreviation: TCTA); phthalocyanine (abbreviation: H$_2$Pc); copper phthalocyanine (abbreviation: CuPc); vanadylphthalocyanine (abbreviation: VOPc); and the like. In addition, the hole-transporting layer 162 may be a multilayer where two or more layers formed of the above substances are combined.

Further, the electron-transporting layer 164 may be provided between the second electrode 152 and the light-emitting layer 163 as shown in FIG. 1. Here, the electron-transporting layer 164 is a layer having a function of transporting electrons injected from the second electrode 152 side to the light-emitting layer 163. By providing the electron-transporting layer 164, the distance between the second electrode 152 and the light-emitting layer 163 can be longer. Consequently, light emission can be prevented from being quenched due to a metal contained in the second electrode 152. The electron-transporting layer 164 is preferably formed by using a substance having a high electron-transporting property, and in particular, it is preferably formed by using a substance having electron mobility of $1\times10^{-6}$ cm$^2$/Vs or more. It is to be noted that the substance having a high hole-transporting property indicates a substance having higher mobility of electrons than that of holes, where the value of a ratio of electron mobility to hole mobility (=electron mobility/hole mobility) is more than 100. The following can be given as a specific example of a substance that can be used to form the electron-transporting layer 164: 2-(4-biphenylyl)-5-(4-tert-buthylphenyl)-1,3,4-oxadiazole (abbreviation: PBD); 1,3-bis[5-(p-tert-buthylphenyl)-1,3,4-oxadiazol-2-yl]benzene (abbreviation: OXD-7); 3-(4-tert-buthylphenyl)-4-phenyl-5-(4-biphenylyl)-1,2,4-triazole (abbreviation: TAZ); 3-(4-tert-buthylphenyl)-4-(4-ethylphenyl)-5-(4-biphenylyl)-1,2,4-triazole (abbreviation: p-EtTAZ); bathophenanthroline (abbreviation: BPhen); bathocuproin (abbreviation: BCP); 4,4-bis(5-methylbenzoxazol-2-yl)stilbene (abbreviation: BzOs); and the like, in addition to a metal complex such as tris(8-quinolinolato)aluminum (abbreviation: Alq$_3$); tris(4-methyl-8-quinolinolato) aluminum (abbreviation: Almq$_3$); bis(10-hydroxybenzo[h]-quinolinato)berylium (abbreviation: BeBq$_2$); bis(2-methyl-8-quinolinolato)-4-phenylphenolate-aluminum (abbreviation: BAlq); bis[2-(2-hydroxyphenyl)benzoxazolate]zinc (abbreviation: Zn(BOX)$_2$); or bis[2-(2-hydroxyphenyl)benzothiazorato]zinc (abbreviation: Zn(BTZ)$_2$). In addition, the electron-transporting layer 164 may also be a multilayer where two or more layers formed of the above substances are combined.

The hole-transporting layer 162 and the electron-transporting layer 164 may be each formed by using a bipolar substance in addition to the above substances. The bipolar substance indicates the following substance: when mobility of either carrier of an electron or a hole is compared with mobility of the other carrier, the value of a ratio of one carrier mobility to the other carrier mobility is 100 or less, preferably 10 or less. As for the bipolar substance, for example, TPAQn; 2,3-bis{4-[N-(1-naphthyl)-N-phenylamino]phenyl}-dibenzo[f,h]quinoxaline (abbreviation: NPADiBzQn); and the like can be given. It is particularly preferable to use a substance having hole and electron mobility of $1\times10^{-6}$ cm$^2$/Vs or more in the bipolar substances. In addition, the hole-transporting layer 162 and the electron-transporting layer 164 may be formed by using the same bipolar substance.

Furthermore, the hole-injecting layer 161 may be provided between the first electrode 151 and the hole-transporting layer 162 as shown in FIG. 1. The hole-injecting layer 161 is a layer having a function of assisting holes to be injected to the hole-transporting layer 162 from the first electrode 151. By providing the hole-injecting layer 161, an ionization potential difference between the first electrode 151 and the hole-transporting layer 162 is relieved; thus, holes are easily injected. The hole-injecting layer 161 is preferably formed by using a substance of which ionization potential is lower than that of a substance forming the hole-transporting layer 162 and higher than that of a substance forming the first electrode 151 or by using a substance of which energy band curves when being provided as a thin film of 1 to 2 nm between the hole-transporting layer 162 and the first electrode 151. As for a specific example of a substance that can be used to form the hole-injecting layer 161, a phthalocyanine-based compound such as phthalocyanine (abbreviation: H$_2$Pc) or copper phthalocyanine (CuPc), a polymer such as poly(ethylenedioxythiophene)/poly(styrenesulfonic acid) solution (PEDOT/PSS), and the like can be given. In other words, the hole-injecting layer 161 can be formed by selecting such a substance that ionization potential of the hole-injecting layer 161 is relatively lower than that of the hole-transporting layer 162. When the hole-injecting layer 161 is provided, the first electrode 151 is preferably formed by using a substance having high work function such as indium tin oxide.

In addition, the electron-injecting layer 165 may be provided between the second electrode 152 and the electron-transporting layer 164 as shown in FIG. 1. Here, the electron-injecting layer 165 is a layer having a function of assisting electrons to be injected to the electron-transporting layer 164 from the second electrode 152. By providing the electron-injecting layer 165, an electron affinity difference between the second electrode 152 and the electron-transporting layer 164 is relieved; thus, electrons are easily injected. The electron-injecting layer 165 is preferably formed by using a substance of which electron affinity is higher than that of a substance forming the electron-transporting layer 164 and lower than that of a substance forming the second electrode 152 or by using a substance of which energy band curves by being provided as a thin film of 1 to 2 nm between the electron-transporting layer 164 and the second electrode 152. The following can be given as a specific example of a substance that can be used to form the electron-injecting layer 165: an inorganic substance such as an alkali metal, an alkaline earth metal, fluoride of an alkali metal, fluoride of an alkaline earth metal, oxide of an alkali metal, or oxide of an alkaline earth metal. In addition to the inorganic substance, a substance that can be used to form the electron-transporting layer 164 such as BPhen, BCP, p-EtTAZ, TAZ, or BzOs can also be used as a substance for forming the electron-injecting layer 165 by selecting a substance of which electron affinity is higher than that of a substance for forming the electron-transporting layer 164 from these substances. In other words, the electron-injecting layer 165 can be formed by selecting such a substance that electron affinity of the electron-injecting layer 165 is relatively higher than that of the electron-transporting layer 164. When the electron-injecting layer 165 is provided, the first electrode 151 is preferably formed by using a substance having low work function such as aluminum.

In the light-emitting element of the present invention as described above, each of the hole-injecting layer 161, the hole-transporting layer 162, the light-emitting layer 163, the electron-transporting layer 164, and the electron-injecting layer 165 may be formed by any of evaporation, ink-jet, coating, and the like. In addition, each of the first electrode 151 and the second electrode 152 may be formed by any of sputtering, evaporation, and the like.

Moreover, a hole-generating layer may be provided instead of the hole-injecting layer 161, or an electron-generating layer may be provided instead of the electron-injecting layer 165.

Here, the hole-generating layer is a layer for generating holes. The hole-generating layer can be formed by mixing at least one substance selected from substances having higher mobility of holes than that of electrons with a substance that shows electron acceptability to the substance having higher mobility of holes than that of electrons. In addition, the hole-generating layer can also be formed by mixing at least one substance selected from bipolar substances with a substance that shows electron acceptability to the bipolar substance. Here, as for the substance having higher mobility of holes than that of electrons, the same substance as the substance that can be used to form the hole-transporting layer 162 can be used. Moreover, as for the bipolar substance, the bipolar substance as described above such as TPAQn can be used. It is particularly preferable to use a substance including a triphenylamine structure in a skeleton among the substances having higher mobility of holes than that of electrons and the bipolar substances. Holes can be generated more easily by using the substance having a triphenylamine structure in a skeleton. Further, as for the substance that shows electron acceptability, it is preferable to use metal oxide such as molybdenum oxide, vanadium oxide, ruthenium oxide, or rhenium oxide.

Further, the electron-generating layer is a layer for generating electrons. The electron-generating layer can be formed by mixing a substance having higher mobility of electrons than that of holes with a substance that shows an electron-donating property to the substance having higher mobility of electrons than that of holes. In addition, the hole-generating layer can also be formed by mixing at least one substance selected from bipolar substances with a substance that shows an electron-donating property to the bipolar substance. Here, as for the substance having higher mobility of electrons than that of holes, the same substance as the substance that can be used to form the electron-transporting layer 164 can be used. Moreover, as for the bipolar substance, the above bipolar substance such as TPAQn can be used. Further, as for the substance that shows an electron-donating property, a substance selected from an alkali metal group and an alkaline earth metal group, specifically, at least one substance selected from lithium oxide ($Li_2O$), calcium oxide (CaO), sodium oxide ($Na_2O$), potassium oxide ($K_2O$), magnesium oxide (MgO), and the like can also be used as the substance that shows an electron-donating property. Moreover, alkali metal fluoride or alkaline earth metal fluoride, specifically, at least one substance selected from lithium fluoride (LiF), cesium fluoride (CsF), calcium fluoride ($CaF_2$), and the like can also be used as the substance that shows an electron-donating property. Further, alkali metal nitride, alkaline earth metal nitride, or the like, specifically, at least one substance selected from calcium nitride, magnesium nitride, and the like can also be used as the substance that shows an electron-donating property.

In the light-emitting element according to the present invention as described above, it may be arbitrarily determined by those carrying out the invention whether or not the hole-injecting layer, the hole-transporting layer, the electron-transporting layer, the electron-injecting layer, and the like are provided. It is to be noted that, when the hole-transporting layer and the electron-transporting layer are provided, quenching due to a metal contained in the electrodes, the hole-injecting layer, or the electron-injecting layer can be reduced. In addition, by providing the electron-injecting layer, the hole-injecting layer, or the like, electrons or holes from the electrode can be efficiently injected.

[Embodiment Mode 3]

Since a light-emitting element containing the organometallic complex according to the present invention as a luminescent substance can emit light efficiently, a light-emitting device which can operate with low power consumption can be obtained by using the light-emitting element according to the present invention for a pixel.

In the present embodiment mode, a circuit configuration and a driving method of a light-emitting device having a display function will be described with reference to FIGS. 2 to 5.

Figure 2:
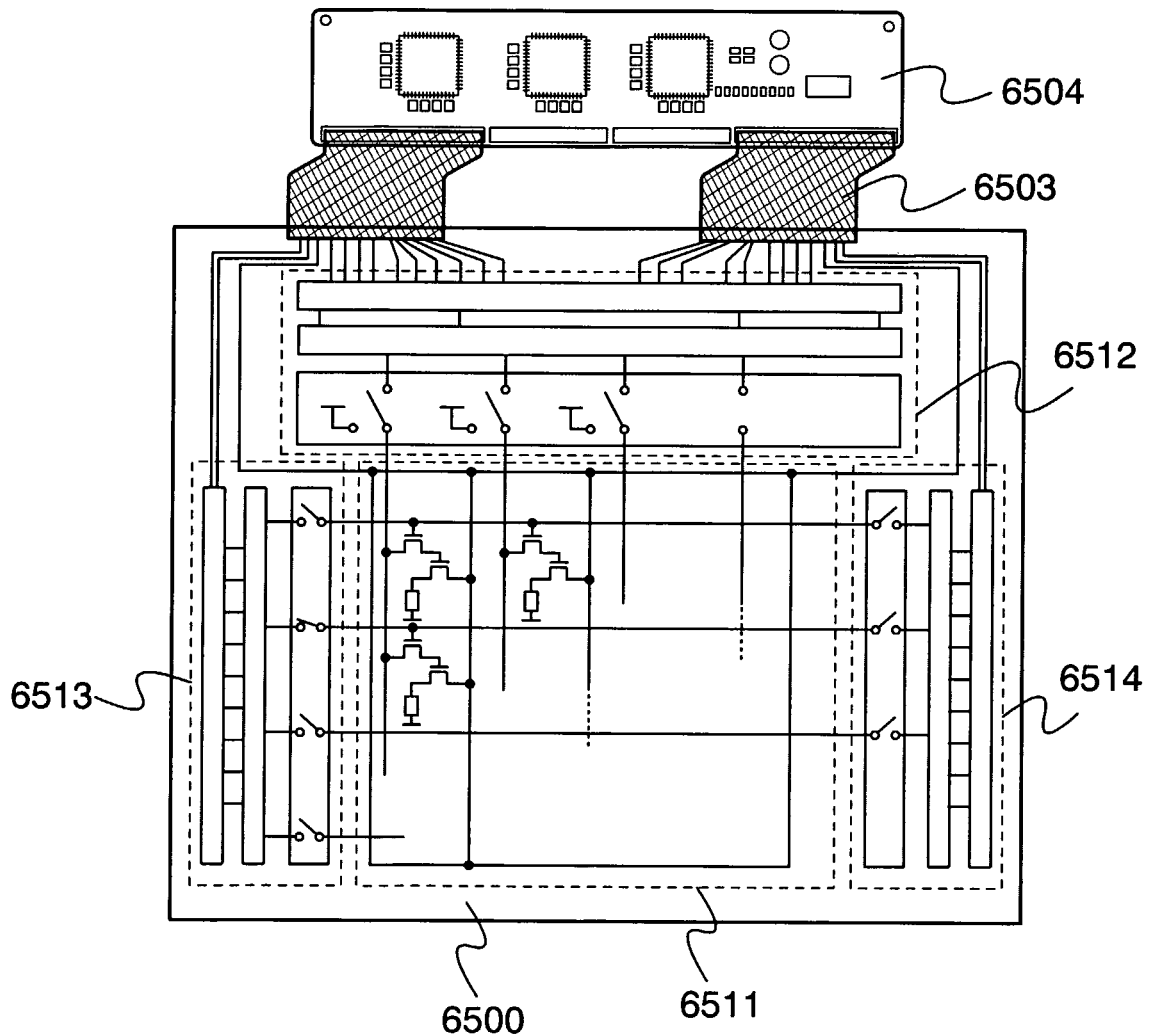
FIG. 2 is a view explaining a light-emitting device to which the present invention is applied.

FIG. 2 is a schematic top view of a light-emitting device to which the present invention is applied. In FIG. 2, a pixel portion 6511, a source-signal line driver circuit 6512, a writing gate-signal line driver circuit 6513, and an erasing gate-signal line driver circuit 6514 are provided over a substrate 6500. Each of the source-signal line driver circuit 6512, the writing gate-signal line driver circuit 6513, and the erasing gate-signal line driver circuit 6514 is connected to FPCs (flexible printed circuits) 6503 that are external input terminals through a group of wirings. Further, each of the source-signal line driver circuit 6512, the writing gate-signal line driver circuit 6513, and the erasing gate-signal line driver circuit 6514 receives signals such as a video signal, a clock signal, a start signal, and a reset signal from the FPCs 6503. In addition, a printed wiring board (PWB) 6504 is attached to the FPCs 6503. It is not always necessary to provide the driver circuit portion over the same substrate as the pixel portion 6511 as described above. For example, the driver circuit portion may be provided outside the substrate by using a TCP in which an IC chip is mounted over an FPC where a wiring pattern is formed.

In the pixel portion 6511, a plurality of source-signal lines extending in columns are arranged in rows. In addition, current-supply lines are arranged in rows, and a plurality of gate-signal lines extending in rows are arranged in columns. Further, a plurality of pairs of circuits each including a light-emitting element are arranged.

Figure 3:
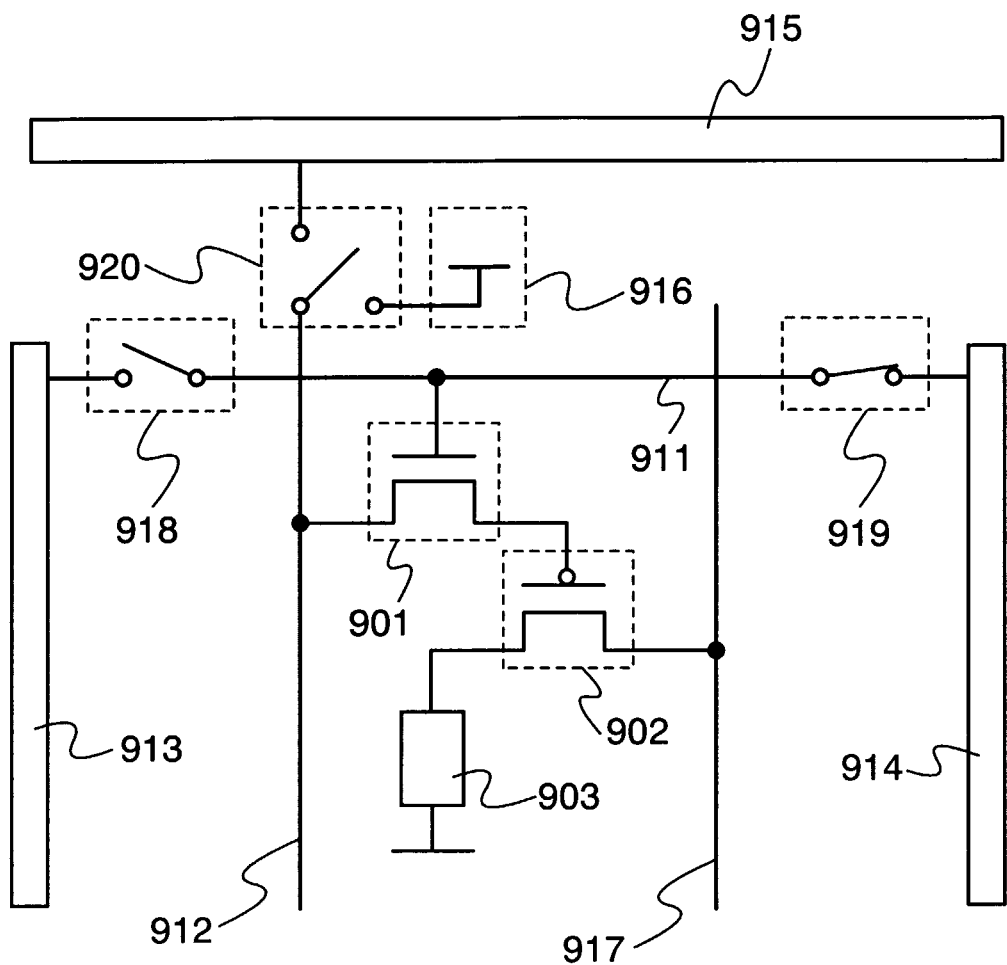
FIG. 3 is a diagram explaining a circuit included in a light-emitting device to which the present invention is applied.

FIG. 3 is a diagram showing a circuit for operating one pixel. The circuit shown in FIG. 3 includes a first transistor 901, a second transistor 902, and a light-emitting element 903.

Each of the first transistor 901 and the second transistor 902 is a three-terminal element including a gate electrode, a drain region, and a source region, and including a channel region between the drain region and the source region. Here, since a source region and a drain region are switched with each other in accordance with a structure or operating conditions of a transistor, it is difficult to identify which one is the drain region or the source region. Therefore, in the present embodiment mode, regions that serve as a source or a drain are respectively referred to as a first electrode and a second electrode of the transistor.

A gate-signal line 911 and a writing gate-signal line driver circuit 913 are provided so as to be electrically connected or unconnected by a switch 918. The gate signal line 911 and an erasing gate-signal line driver circuit 914 are provided so as to be electrically connected or unconnected by a switch 919. Further, a source-signal line 912 is provided so as to be electrically connected to any of a source-signal line driver circuit 915 and a power source 916 by a switch 920. A gate of the first transistor 901 is electrically connected to the gate-signal line 911, a first electrode of the first transistor is electrically connected to the source-signal line 912, and a second electrode is electrically connected to a gate electrode of the second transistor 902. A first electrode of the second transistor 902 is electrically connected to a current-supply line 917 and a second electrode is electrically connected to one electrode included in the light-emitting element 903. It is to be noted that the switch 918 may be included in the writing gate-signal line driver circuit 913, the switch 919 may be included in the erasing gate-signal line driver circuit 914, and the switch 920 may be included in the source-signal line driver circuit 915.

Figure 4:
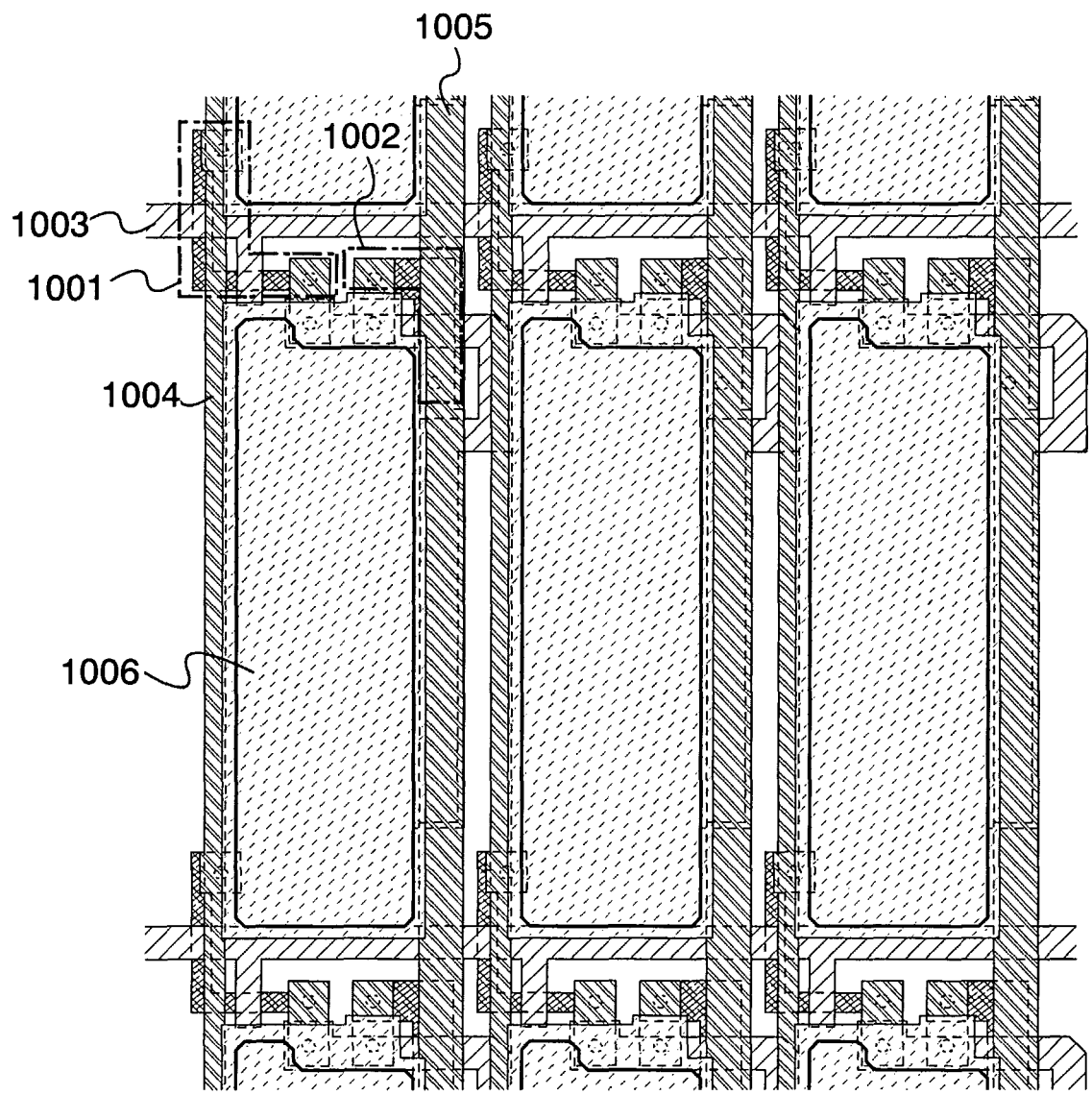
FIG. 4 is a top view of a light-emitting device to which the present invention is applied.

In addition, arrangement of a transistor, a light-emitting element, and the like in a pixel portion is not particularly limited. For example, arrangement shown in a top view of FIG. 4 can be employed. In FIG. 4, a first electrode of a first transistor 1001 is connected to a source-signal line 1004 and a second electrode is connected to a gate electrode of a second transistor 1002. Moreover, a first electrode of the second transistor 1002 is connected to a current-supply line 1005 and a second electrode is connected an electrode 1006 of a light-emitting element. A part of a gate-signal line 1003 serves as a gate electrode of the first transistor 1001.

Figure 5:
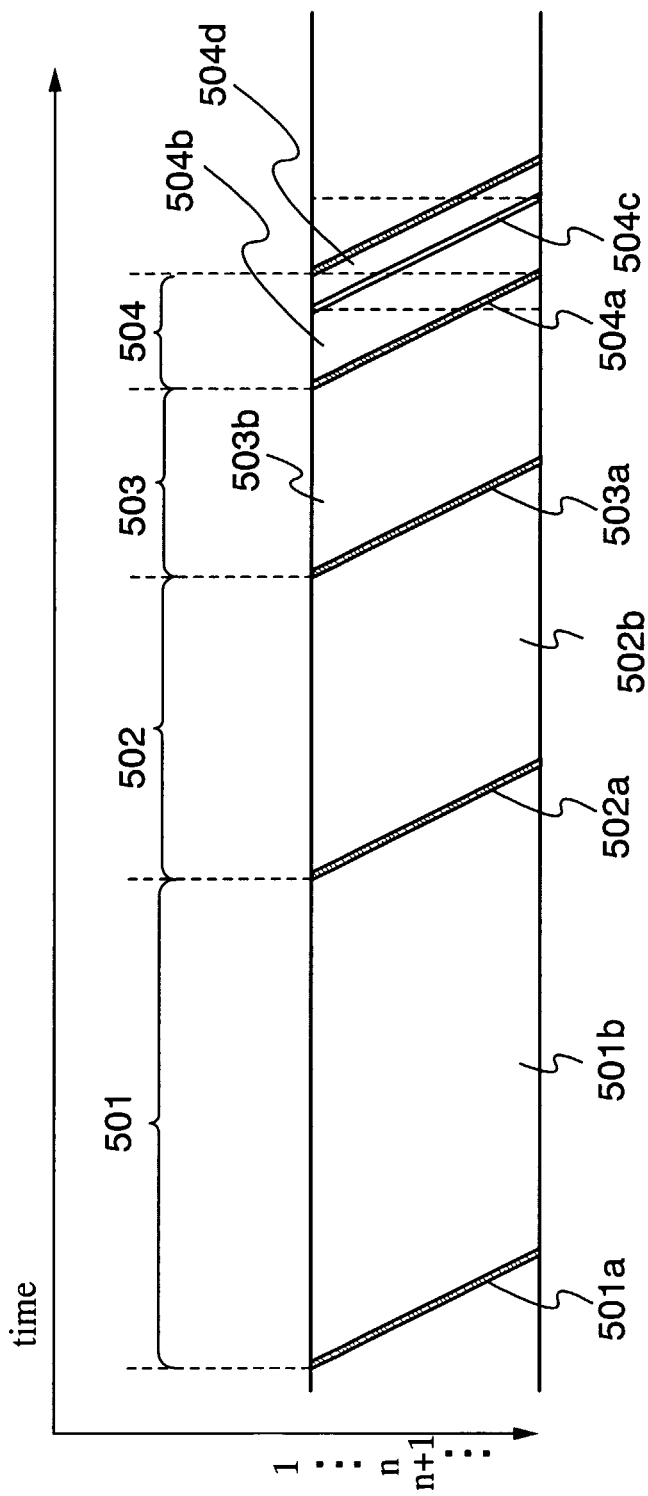
FIG. 5 is a diagram explaining a frame operation of a light-emitting device to which the present invention is applied.

Next, a driving method will be explained. FIG. 5 is a diagram illustrating an operation per frame with time. In FIG. 5, the horizontal direction indicates passage of time, and the vertical direction indicates ordinal numbers of gate signal lines.

When a light-emitting device according to the present invention is used to display images, rewrite operations for a screen are repeated in a display period. Although the number of rewrites is not particularly limited, it is preferable that the number of rewrites be at least about 60 times per second so as not to make an image viewer recognize flickers. Here, a period for which a rewrite operation is performed for a screen (one frame) is referred to as one frame period.

As shown in FIG. 5, one frame is divided into four sub-frames 501, 502, 503, and 504 respectively including writing periods 501a, 502a, 503a, and 504a and retention periods 501b, 502b, 503b, and 504b. In the retention period, a light-emitting element to which a signal for emitting light is given is made to be in an emitting state. The ratio of the length of the retention period in each sub-frame is: the first sub-frame 501: the second sub-frame 502: the third sub-frame 503: the fourth sub-frame 504=$2^3:2^2:2^1:2^0$=8:4:2:1. This makes 4-bit gradation possible. However, the number of bits or the number of gradations is not limited to the ones described here. For example, eight sub-frames may be provided so as to perform 8-bit gradation.

An operation in one frame will be explained. First, in the sub-frame 501, writing operations are sequentially performed for a first row to a last row. Accordingly, the start time of the writing period 501a is different depending on the rows. When the writing period 501a is completed, the rows are sequentially moved into the retention period 501b. In the retention period 501b, a light-emitting element to which a signal for emitting light is given is made to be in an emitting state. In addition, when the retention period 501b is completed, the rows are sequentially moved into the next sub-frame 502, and writing operations are sequentially performed for the first row to the last row as in the case of the sub-frame 501. The operations as described above are repeated up to the retention period 504b of the sub-frame 504 to complete an operation in the sub-frame 504. When the operation in the sub-frame 504 is completed, the rows are moved into the next frame. Thus, the total of time for which light is emitted in each sub-frame is emission time for each light-emitting element in one frame. By varying this emission time with respect to each light-emitting element to have various combinations in one pixel, various display colors with different luminosity and chromaticity can be made.

As in the sub-frame 504, when forcible termination of a retention period of a row for which writing has been already completed and which is moved into the retention period is required before writing for the last row is completed, it is preferable that an erasing period 504c be provided after the retention period 504b and a row be controlled so as to be in a non-emitting state forcibly. Then, the row forcibly made to be in the non-emitting state is kept in the non-emitting state for a certain period (this period is referred to as a non-emission period 504d). Then, immediately after the writing period 504a of the last row is completed, the rows are sequentially moved into the writing period of the next sub-frame (or the next frame), starting from the first row. This makes it possible to prevent the writing period 504a of the sub-frame 504 from overlapping with the writing period of the next sub-frame.

Although the sub-frames 501 to 504 are arranged in the order from the longest retention period to the shortest in the present embodiment mode, the arrangement as in the present embodiment mode is not always necessary. For example, the sub-frames 501 to 504 may be arranged in the order from the shortest retention period to the longest, or may be arranged in random order. In addition, the sub-frames may be further divided into a plurality of frames. In other words, scanning of the gate signal lines may be performed plural times while giving the same image signal.

Now, an operation of the circuit shown in FIG. 3 in a writing period and an erasing period will be explained.

First, an operation in a writing period will be explained. In the writing period, the gate-signal line 911 in the n-th row (n is a natural number) is electrically connected to the writing gate-signal line driver circuit 913 through the switch 918, and unconnected to the erasing gate-signal line driver circuit 914. In addition, the source-signal line 912 is electrically connected to the source-signal line driver circuit 915 through the switch 920. Here, a signal is inputted into the gate of the first transistor 901 connected to the gate-signal line 911 in the n-th row (n is a natural number) to turn on the first transistor 901. Then, at this moment, image signals are inputted concurrently into the source-signal lines 912 in the first to the last columns. It is to be noted that the image signals inputted from the source-signal lines 912 in the respective columns are independent of each other. The image signal inputted from the source-signal line 912 is inputted into the gate electrode of the second transistor 902 through the first transistor 901 connected to each of the source-signal lines 912. At this moment, whether the light-emitting element 903 emits light or not is determined depending on the signal imputed to the second transistor 902. For example, when the second transistor 902 is a P-channel transistor, the light-emitting element 903 emits light by inputting a Low Level signal to the gate electrode of the second transistor 902. On the other hand, when the second transistor 902 is an N-channel transistor, the light-emitting element 903 emits light by inputting a High Level signal to the gate electrode of the second transistor 902.

Next, an operation in an erasing period will be explained. In the erasing period, the gate-signal line 911 in the n-th row (n is a natural number) is electrically connected to the erasing gate-signal line driver circuit 914 through the switch 919 and unconnected to the wiring gate-signal line driver circuit 913. In addition, the source-signal line 912 is electrically connected to the power source 916 through the switch 920. Here, a signal is inputted into the gate of the first transistor 901 connected to the gate-signal line 911 in the n-th row (n is a natural number) to turn on the first transistor 901. Then, at this moment, erasing signals are inputted concurrently into the source signal lines 912 in the first to last columns. The erasing signal inputted from each of the source signal lines 912 is inputted into the gate electrode of the second transistor 902 through the first transistor 901 connected to each of the source-signal lines 912. At this moment, current supply from the current-supply line 917 to the light-emitting element 903 is stopped by the signal inputted into the second transistor 902. Then, the light-emitting element 903 is forcibly made to emit no light. For example, when the second transistor 902 is a P-channel transistor, the light-emitting element 903 emits no light by inputting a High Level signal to the gate electrode of the second transistor 902. On the other hand, when the second transistor 902 is an N-channel transistor, the light-emitting element 903 emits no light by inputting a Low Level signal to the gate electrode of the second transistor 902.

It is to be noted that, as for the n-th row (n is a natural number), signals for erasing are inputted by the operation as described above in an erasing period. However, as described above, the other row (referred to as the m-th row (m is a natural number)) may be in a writing period while the n-th row is in an erasing period. In such a case, it is necessary to input a signal for erasing to the n-th row and input a signal for writing to the m-th row by using a source signal line in the same column. Therefore, an operation that will be explained below is preferable.

Immediately after the light-emitting element 903 in the n-th row is made to emit no light by the operation in the erasing period as explained above, the gate-signal line 911 and the erasing gate-signal line driver circuit 914 are made to be unconnected to each other, and the switch 920 is switched to connect the source-signal line 912 and the source-signal line driver circuit 915. Then, in addition to connecting the source-signal line 912 to the source-signal line driver circuit 915, the gate-signal line 911 is connected to the writing gate-signal line driver circuit 913. Then, a signal is inputted selectively into the gate-signal line 911 in the m-th row from the writing gate-signal line driver circuit 913 to turn on the first transistor 901, and signals for writing are inputted into the source signal-lines 912 in the first to last columns from the source-signal line driver circuit 915. This signal makes the light-emitting element 903 in the m-th row be in an emitting or non-emitting state.

Immediately after the writing period for the m-th row is completed as described above, an erasing period for the (n+1)-th row is started. For that purpose, the gate-signal line 911 and the writing gate-signal line driver circuit 913 are made to be unconnected to each other, and the switch 920 is switched to connect the source-signal line 912 and the power source 916. Further, the gate-signal line 911, which is unconnected to the writing gate-signal line driver circuit 913, is made to be connected to the erasing gate-signal line driver circuit 914. Then, a signal is inputted selectively into the gate-signal line 911 in the (n+1)-th row from the erasing gate-signal line driver circuit 914 to turn on the first transistor 901, and an erasing signal is inputted from the power source 916. Immediately after the erasing period for the (n+1)-th row is thus completed, a writing period for the (m+1)-th row is started. Then, an erasing period and a writing period may be repeated in the same way until an erasing period for the last row is completed.

Although the example in which the writing period for the m-th row is provided between the erasing period for the n-th row and the erasing period for the (n+1)-th row is explained in the present embodiment mode, the present invention is not limited thereto. The writing period for the m-th row may be provided between an erasing period for (n−1)-th row and an erasing period for n-th row as well.

In addition, in the present embodiment mode, the operation is repeated, in which the erasing gate-signal line driver circuit 914 and one gate-signal line 911 are made to be unconnected to each other as well as the writing gate-signal line driver circuit 913 and the other gate-signal line 911 are made to be connected to each other when the non-emission period 504*d* is provided as in the sub-frame 504. This type of operation may also be performed in a frame in which a non-emission period is not particularly provided.

[Embodiment Mode 4]

Examples of a cross section of a light-emitting device including a light-emitting element according to the present invention will be described with reference to FIGS. 6A to 6C.

Figure 6A:
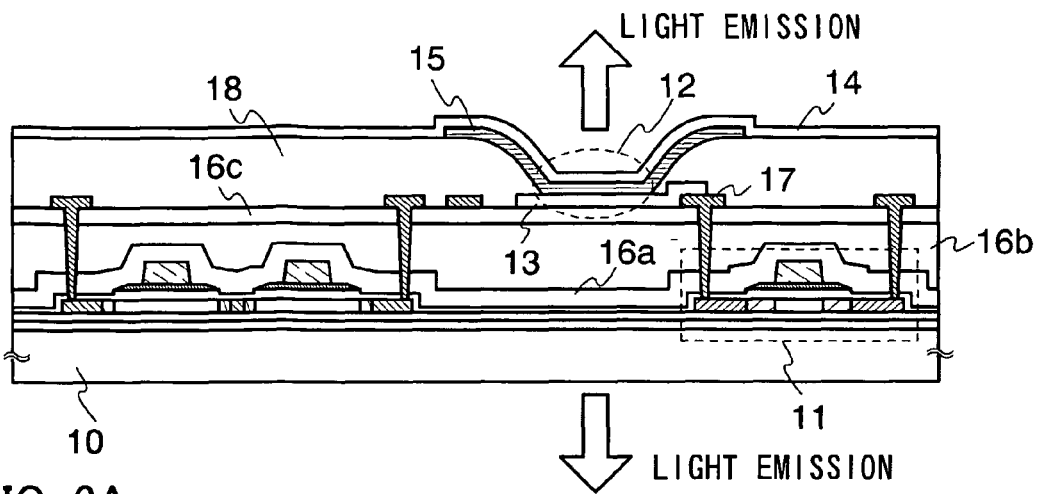
FIGS. 6A to 6C are cross-sectional views of a light-emitting device to which the present invention is applied.
Figure 6B:
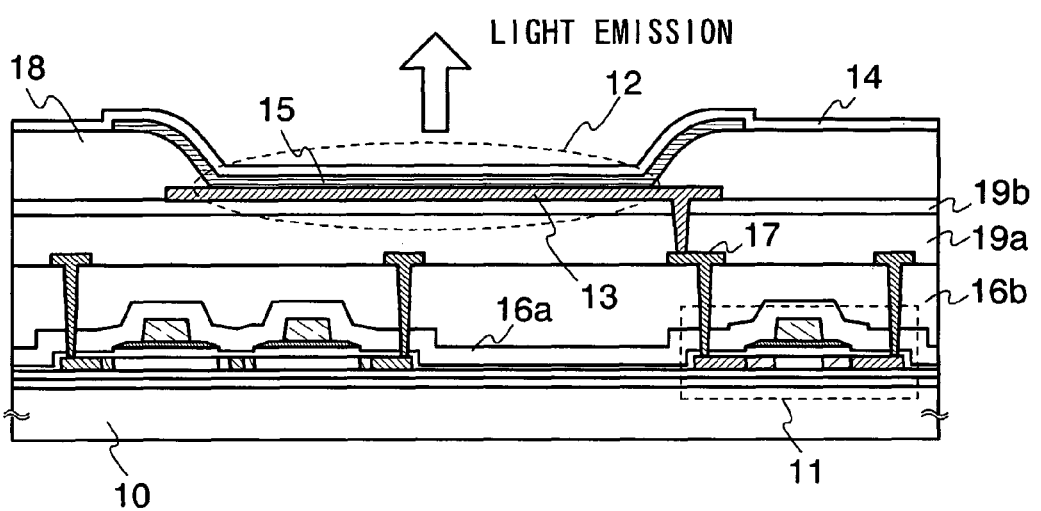
Figure 6C:
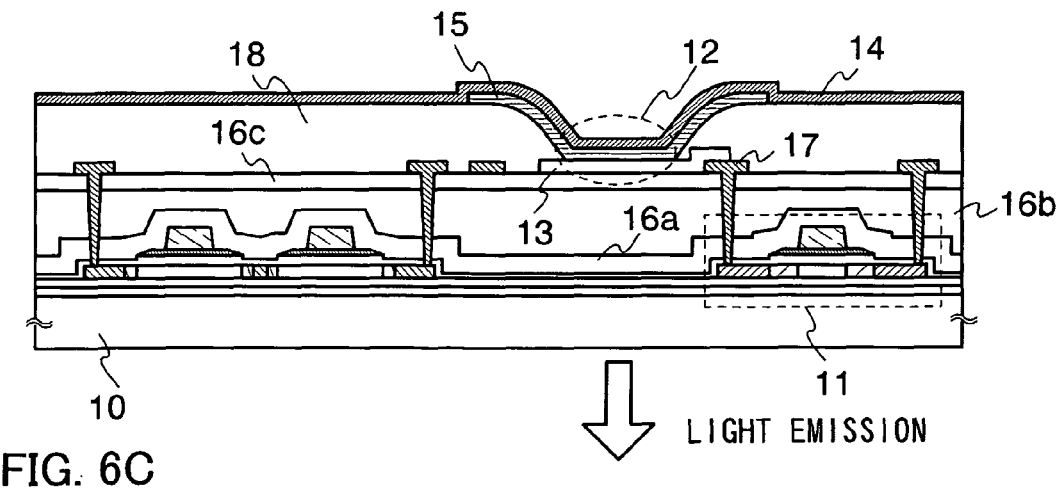

In each of FIGS. 6A to 6C, a portion surrounded by a dotted line is a transistor 11 provided for driving a light-emitting element 12 according to the present invention. The light-emitting element 12 is a light-emitting element according to the present invention, which has a layer 15 in which a layer for generating holes, a layer for generating electrons, and a layer containing a luminescent substance are stacked between a first electrode 13 and a second electrode 14. A drain of the transistor 11 and the first electrode 13 are electrically connected to each other by a wiring 17 running through a first interlayer insulating film 16 (16*a*, 16*b*, and 16*c*). In addition, the light-emitting element 12 is separated by a partition layer 18 from another light-emitting element that is provided adjacently. A light-emitting device having such a structure according to the present invention is provided over a substrate 10 in the present embodiment mode.

It is to be noted that the transistor 11 shown in each of FIGS. 6A to 6C is a top-gate TFT in which a gate electrode is provided on the opposite side of a substrate with a semiconductor layer as a center. However, the structure of the transistor 11 is not particularly limited. For example, a bottom-gate TFT may be used. In the case of a bottom-gate TFT, a TFT where a protective film is formed over a semiconductor layer that forms a channel (a channel-protected TFT) may be employed, or a TFT where part of a semiconductor layer that forms a channel is concave (a channel-etched TFT) may be employed.

In addition, a semiconductor layer which forms the transistor 11 may be either crystalline or amorphous, or alternatively, semi-amorphous or the like.

The following will describe a semi-amorphous semiconductor. The semi-amorphous semiconductor is a semiconductor that has an intermediate structure between amorphous and crystalline (including single-crystal or polycrystalline) structures and has a third state that is stable in terms of free energy, which includes a crystalline region that has short range order and lattice distortion. Further, a crystal grain of 0.5 to 20 nm is included in at least a region in a film of the semi-amorphous semiconductor. Raman spectrum is shifted to a wave number side lower than 520 cm$^{-1}$. The diffraction peaks of (111) and (220), which are believed to be derived from silicon crystal lattice, are observed by the X-ray diffraction. The semi-amorphous semiconductor contains hydrogen or halogen of at least 1 atomic % or more for terminating dangling bonds. The semi-amorphous semiconductor is also referred to as a so-called microcrystalline semiconductor and formed by glow discharge decomposition (using plasma CVD) with a gas selected from $SiH_4$, $Si_2H_6$, $SiH_2Cl_2$, $SiHCl_3$, $SiCl_4$, $SiF_4$, and the like. Each of these gases may also be diluted with $H_2$, or a mixture of $H_2$ and one or more of rare gas elements of He, Ar, Kr, and Ne. The dilution ratio is set to be in the range of 1:2 to 1:1000. The pressure is set to be approximately in the range of 0.1 to 133 Pa. The power frequency is set to be 1 to 120 MHz, preferably, 13 to 60 MHz. The substrate heating temperature may be set to be 300° C. or lower, more preferably, 100 to 250° C. As for impurity elements contained in the film, each concentration of impurities for atmospheric constituents such as oxygen, nitrogen and carbon is preferably set to be $1\times10^{20}/cm^3$ or lower. In particular, the oxygen concentration is set to be $5\times10^{19}/cm^3$ or less, preferably, $1\times10^{19}/cm^3$ or less. It is to be noted that the mobility of a TFT (a thin film transistor) using the semi-amorphous semiconductor is approximately 1 to 10 $cm^2/Vsec$.

Further, specific examples of crystalline semiconductors for the semiconductor layer include single-crystal or polycrystalline silicon and silicon-germanium, which may be formed by laser crystallization or may be formed by crystallization with solid-phase growth using an element such as nickel.

In the case of using an amorphous substance, for example, amorphous silicon to form the semiconductor layer, it is preferable that the light-emitting device have a circuit in which the transistor 11 and the other transistor (a transistor forming the circuit for driving the light-emitting element) are all N-channel transistors. Other than that case, the light-emitting device may have a circuit including one of an N-channel transistor and a P-channel transistor or may have a circuit including both of an N-channel transistor and a P-channel transistor.

Further, the first interlayer insulating film 16 may be a multilayer as shown in FIGS. 6A to 6C, or may be a single layer. It is to be noted that the first interlayer insulating film 16a contains an inorganic substance such as silicon oxide or silicon nitride, and the first interlayer insulating film 16b contains a substance with a self-planarizing property such as acrylic, siloxane, or silicon oxide that can be formed by being coated. It is to be noted that a siloxane resin has a framework structure formed by a Si—O—Si bond, and includes hydrogen or an alkyl group such as a methyl group as a substituent. In addition, the first interlayer insulating film 16c includes a silicon nitride film containing argon (Ar). The substances contained in the respective layers are not particularly limited; therefore, substances other than the substances mentioned here may also be used. Moreover, a layer containing a substance other than these substances may also be combined. In this way, both of an inorganic substance and an organic substance, or one of an inorganic substance and an organic substance may be used to form the first interlayer insulating film 16.

As for the partition layer 18, it is preferable that an edge portion have a shape varying continuously in curvature radius. In addition, a substance such as acrylic, siloxane, resist, or silicon oxide is used to form the partition layer 18. One or both of an inorganic substance and an organic substance may be used to form the partition layer 18.

In each of FIGS. 6A and 6C, only the first interlayer insulating film 16 is provided between the transistor 11 and the light-emitting element 12. However, as shown in FIG. 6B, a second interlayer insulating film 19 (19a and 19b) may be provided in addition to the first interlayer insulating film 16 (16a and 16b). In the light-emitting device shown in FIG. 6B, the first electrode 13 is connected to the wiring 17 running through the second interlayer insulating film 19.

The second interlayer insulating film 19 may be a multilayer or a single layer as in the case of the first interlayer insulating film 16. The second interlayer insulating film 19a contains a substance with a self-planarizing property such as acrylic, siloxane, or silicon oxide that can be formed by being coated. In addition, the second interlayer insulating film 19b includes a silicon nitride film containing argon (Ar). The substances contained in the respective layers are not particularly limited; therefore, substances other than the substances mentioned here may also be used. Moreover, a layer containing a substance other than these substances may also be combined. In this way, both of an inorganic substance and an organic substance, or one of an inorganic substance and an organic substance may be used to form the second interlayer insulating film 19.

In the light-emitting element 12, in the case where both of the first electrode 13 and the second electrode 14 are formed by using a light-transmitting substance, emitted light can be extracted from both of the first electrode 13 side and the second electrode 14 side as indicated by outline arrows of FIG. 6A. In the case where only the second electrode 14 is formed by using a light-transmitting substance, emitted light can be extracted from only the second electrode 14 side as indicated by an outline arrow of FIG. 6B. In this case, it is preferable that the first electrode 13 be formed by using a highly reflective material, or a film composed of a highly reflective material (a reflective film) be provided below the first electrode 13. Further, in the case where only the first electrode 13 is formed by using a light-transmitting substance, emitted light can be extracted from only the first electrode 13 side as indicated by an outline arrow of FIG. 6C. In this case, it is preferable that the second electrode 14 be formed by using a highly reflective material, or a reflective film be provided above the second electrode 14.

In addition, the layer 15 may be stacked so that the light-emitting element 12 is operated when a voltage is applied so as to make the potential of the second electrode 14 higher than that of the first electrode 13. Alternatively, the layer 15 may be stacked so that the light-emitting element 12 is operated when a voltage is applied so as to make the potential of the second electrode 14 lower than that of the first electrode 13. The transistor 11 is an N-channel transistor in the former case, and the transistor 11 is a P-channel transistor in the latter case.

As described above, an active light-emitting device in which driving of a light-emitting element is controlled by a transistor is explained in the present embodiment mode.

The present invention may be applied to a passive light-emitting device without limiting to an active light-emitting device. In particular, a light-emitting element manufactured by using the organometallic complex according to the present invention, in which excitation and luminescence can be repeated efficiently even in a high-luminance-region, is suitable for a pixel of a passive light-emitting device which is required to emit light at high luminance momentarily.

Figure 7:
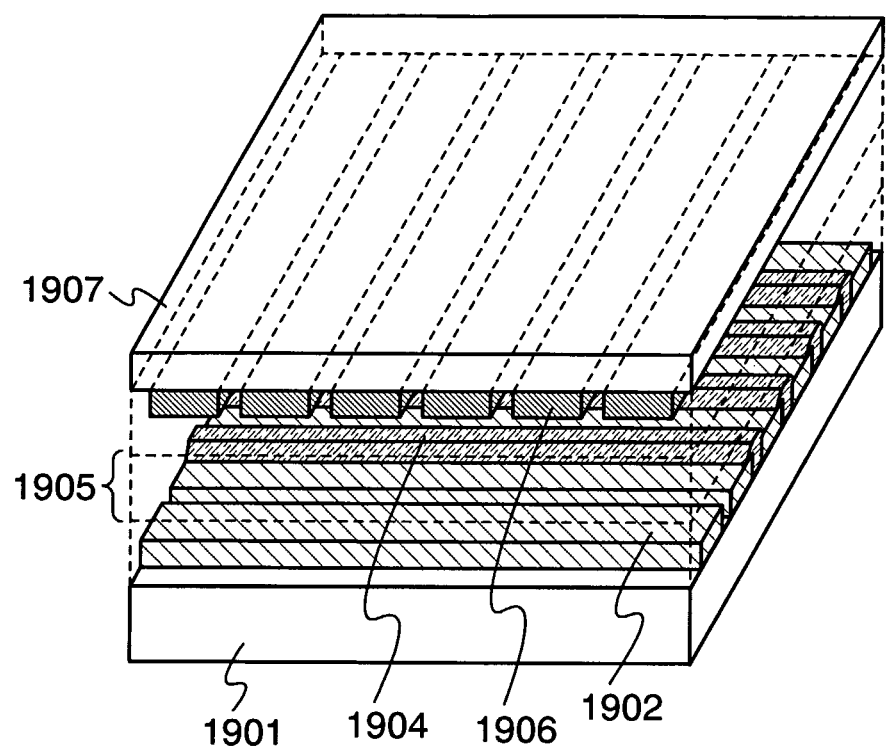
FIG. 7 is a view explaining a light-emitting device to which the present invention is applied.

FIG. 7 shows a perspective view of a passive light-emitting device to which the present invention is applied. In FIG. 7, electrodes 1902 and 1906 are provided between substrates 1901 and 1907. The electrodes 1902 and 1906 are provided so as to intersect with each other. Further, a light-emitting layer 1905 (indicated by a dashed line to show locations of 1902, 1904 and the like) is provided between the electrodes 1902 and 1906. A hole-transporting layer, an electron-transporting layer, and the like may be provided between the light-emitting layer 1905 and the electrode 1902, or between the light-emitting layer 1905 and the electrode 1906. Further, a partition layer 1904 is provided to cover an end portion of the electrode 1902. It is to be noted that a part of the partition layer 1904 is omitted in FIG. 7. In addition, the passive light-emitting device can be driven with low power consumption by including a light-emitting element according to the present invention, which can be operated by a low drive voltage.

[Embodiment Mode 5]

Since a light-emitting device including a light-emitting element according to the present invention can be operated by a low drive voltage, an inexpensive electronic device consuming less power can be obtained in accordance with the present invention.

Figure 8A:
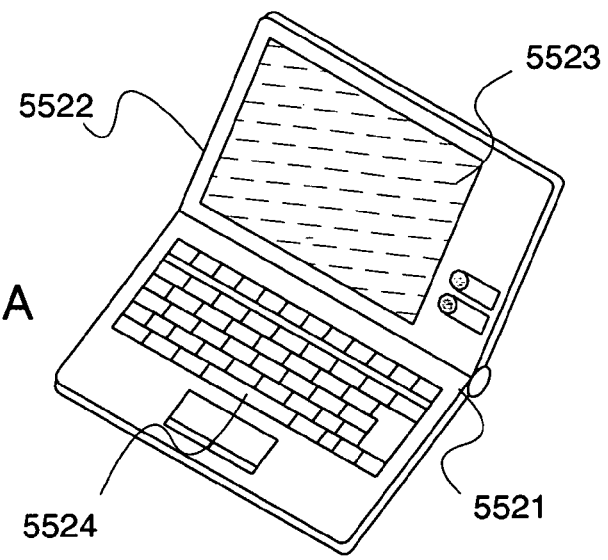
FIGS. 8A to 8C are views explaining electronic devices to which the present invention is applied.
Figure 8B:
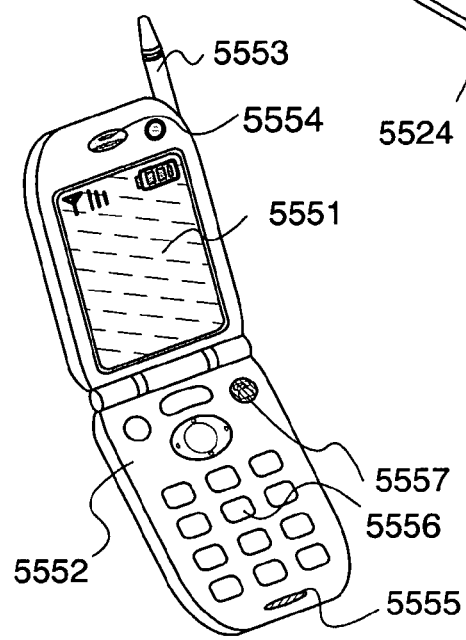
Figure 8C:
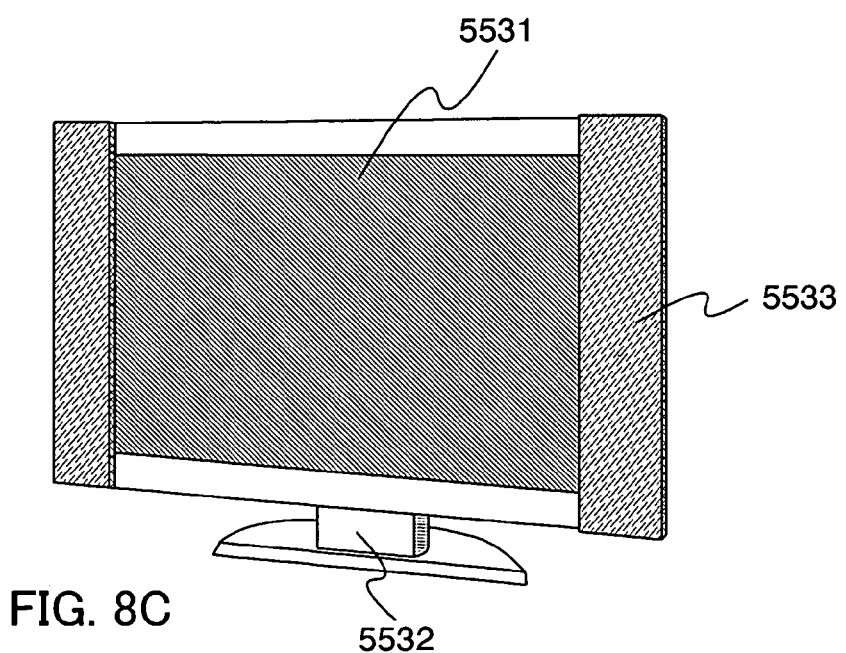

FIGS. 8A to 8C show examples of electronic devices in which the light-emitting device according to the present invention is incorporated.

FIG. 8A is a notebook personal computer manufactured by applying the present invention thereto, which includes a main body 5521, a housing 5522, a display portion 5523, a keyboard 5524, and the like. The personal computer can be achieved by incorporating a light-emitting device having a light-emitting element according to the present invention as the display portion.

FIG. 8B is a telephone set manufactured by applying the present invention thereto, in which a main body 5552 includes a display portion 5551, an audio output portion 5554, an audio input portion 5555, operation switches 5556 and 5557, an antenna 5553, and the like. The telephone set can be achieved by incorporating a light-emitting device having a light-emitting element according to the present invention as the display portion.

FIG. 8C is a television set manufactured by applying the present invention, which includes a display portion 5531, a housing 5532, a speaker 5533, and the like. The television set can be achieved by incorporating a light-emitting device having a light-emitting element according to the present invention as the display portion.

As described above, the light-emitting device according to the present invention is highly suitable for a display portion of various electronic devices.

It is to be noted that the present embodiment mode describes the personal computer, the telephone set, the television set, and the like; however, a light-emitting device having a light-emitting element according to the present invention may also be mounted on a navigation system, a camera, or the like as well.

[Embodiment 1]

Synthesis Example 1

A synthesis method of an organometallic complex according to the present invention represented by the structural formula (8) (referred to as: (acetylacetonato)bis[2,3-bis(4-fluorophenyl)pyrazinato]iridium(III)) will be described.

[Step 1: Synthesis of a Ligand (Abbreviation: HFDPPR)]

First, with dehydrated ethanol as a solvent, 16.8 g of 4,4'-difluorobenzil (by Tokyo Chemical Industry Co., Ltd.) and 4.5 g of ethylenediamine (by Kanto Chemical Co., Inc.) were mixed, and the mixture was refluxed at 105° C. for six hours. After reaction, a reaction solution was condensed by using an evaporator, and an obtained residue was recrystallized by using ethanol; thus, 2,3-bis(4-fluorophenyl)-5,6-dihydropyrazine was obtained (reddish brown powder, yield: 93%).

Then, 16.1 g of 2,3-bis(4-fluorophenyl)-5,6-dihydropyrazine obtained as described above and 5.6 g of potassium hydroxide were mixed in a three-neck flask equipped with a mechanical stirrer, and 100 mL of glycerol was added as a solvent. Thereafter, the mixture was stirred while heating at 190° C. for six hours. After reaction, a reddish brown film precipitated in an upper layer of glycerol was washed with water. The washed film was purified by column chromatography using a mixed solution of hexane and ethyl acetate (the volume ratio of hexane to ethyl acetate is 2:1) as a developing solvent ($R_f$=0.57). Further, by recrystallization using ethanol, 2.8 g of a ligand referred to as 2,3-bis(4-fluorophenyl)pyrazine (abbreviation: HFDPPR) was obtained (light yellow crystal, yield: 17.5%). A synthesis scheme (c-1) relating to the synthesis of Step 1 is shown below.

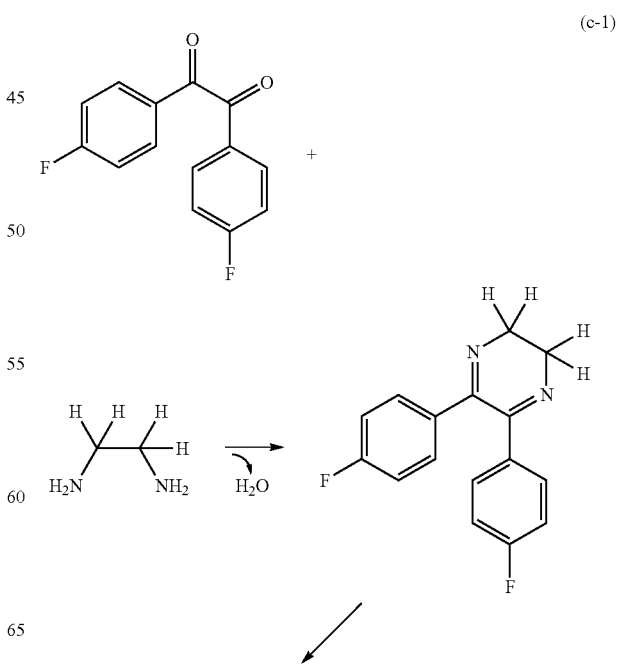

(c-1)

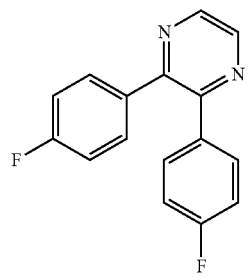

[Step 2: Synthesis of a Binuclear Complex (Abbreviation: [Ir(FDPPR)₂Cl]₂)]

Subsequently, with a mixture of 30 mL of 2-ethoxyethanol and 10 mL of water as a solvent, 5.01 g of HFDPPR that is the ligand obtained as described above and 1.01 g of iridium (III) chloride hydrochloride hydrate (IrCl₃.HCl.H₂O) (by Sigma-Aldrich) were mixed. The mixture was refluxed in a nitrogen atmosphere for 16 hours to obtain a binuclear complex [Ir(FDPPR)₂Cl]₂ (reddish brown powder, yield: 31%). A synthesis scheme (c-2) relating to the synthesis of Step 2 is shown below.

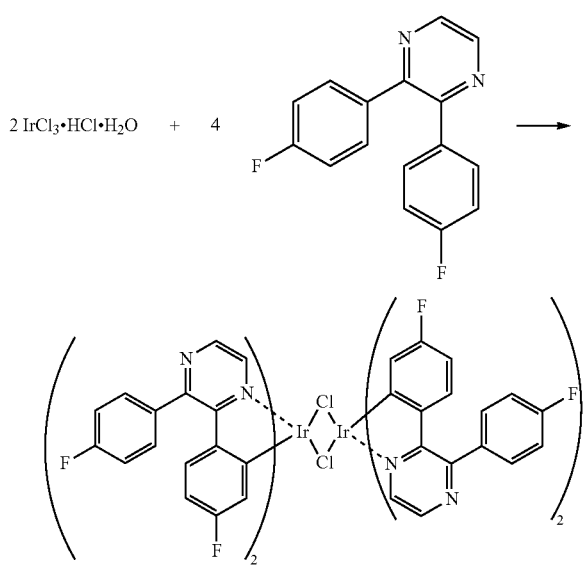

[Step 3: Synthesis of an Organometallic Complex According to the Present Invention (Abbreviation: [Ir(Fdppr)₂(acac)])]

Further, with 20 mL of 2-ethoxyethanol as a solvent, 0.76 g of [Ir(FDPPR)₂Cl]₂, 0.15 mL of acetylacetone (abbreviation: Hacac), and 0.53 g of sodium carbonate were mixed. The mixture was refluxed in a nitrogen atmosphere for 17 hours to obtain yellow orange powder (yield: 16%). A synthesis scheme (c-3) relating to the synthesis of Step 3 is shown below.

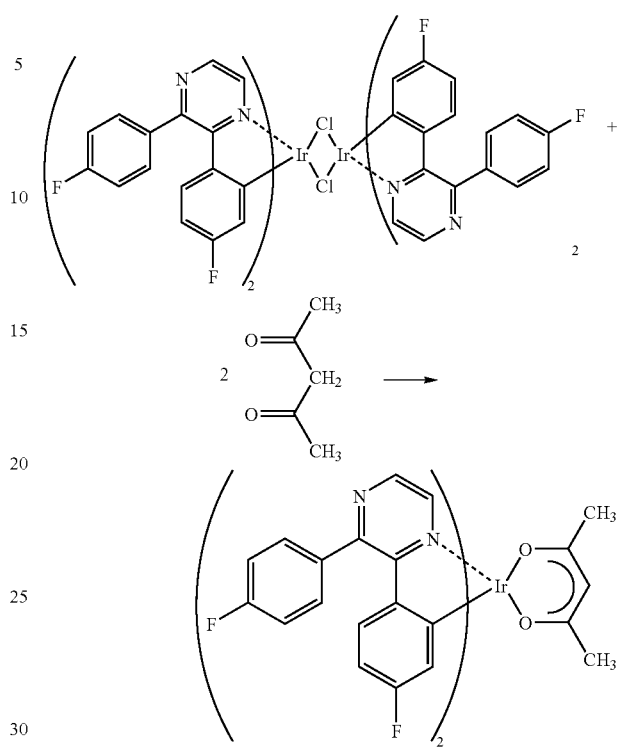

Figure 9:
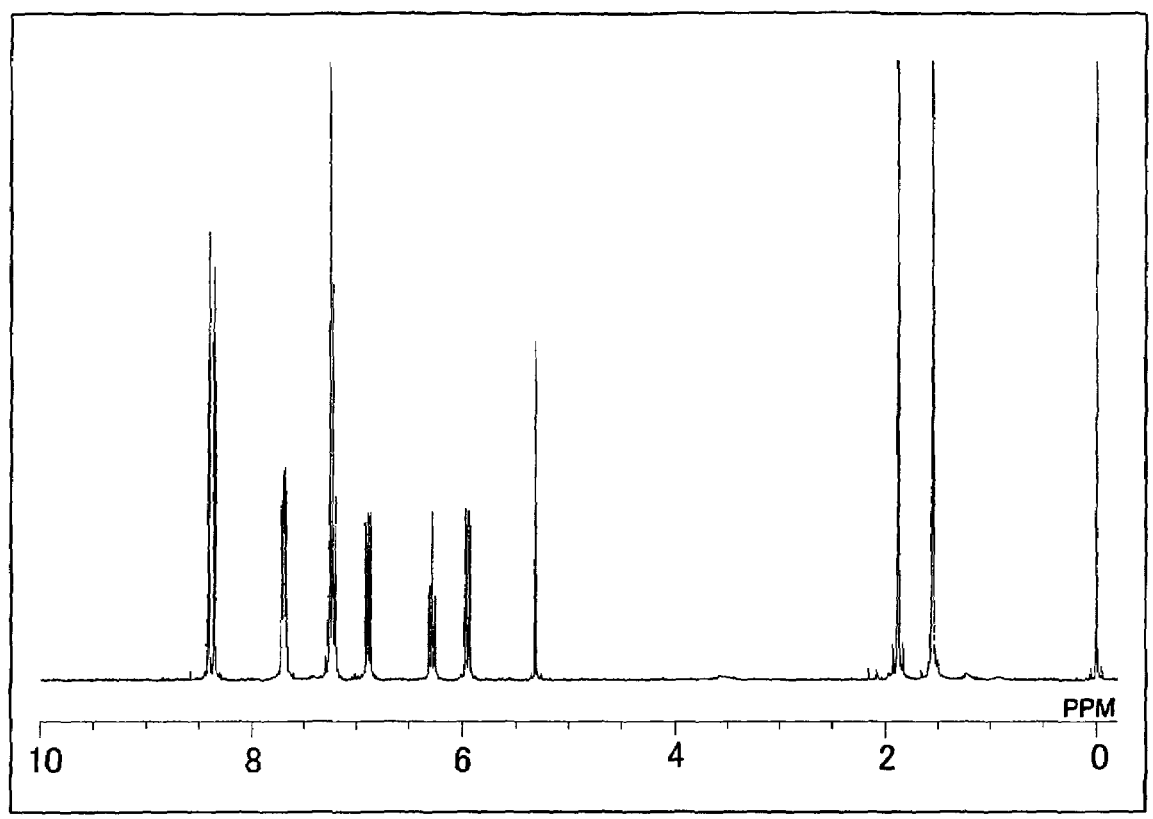
FIG. 9 is a graph showing $^1$H-NMR of an organometallic complex according to the present invention, which is synthesized in Synthesis Example 1.

The obtained yellow orange powder was analyzed by nuclear magnetic resonance spectroscopy (¹H-NMR) and a result as shown below was obtained. The product was identified to be Ir(Fdppr)₂(acac) represented by the structural formula (8), which is one of organometallic complexes according to the present invention. The ¹H-NMR chart is shown in FIG. 9.

¹H-NMR.δ(CDCl₃): 8.38(dd,4H), 7.69(dd,4H), 7.23(m, 4H), 6.89(dd,2H), 6.29(td,2H), 5.95(dd,2H), 5.31(s,1H), 1.89(s,6H)

In addition, measurement of the decomposition temperature $T_d$ of the obtained organometallic complex Ir(Fdppr)₂(acac) according to the present invention was conducted by a thermo-gravimetric/differential thermal analyzer (by Seiko Instruments Inc., TG/DTA-320) to find $T_d$=312° C., and thus, it was determined that Ir(Fdppr)₂(acac) shows favorable heat resistance.

Figure 10:
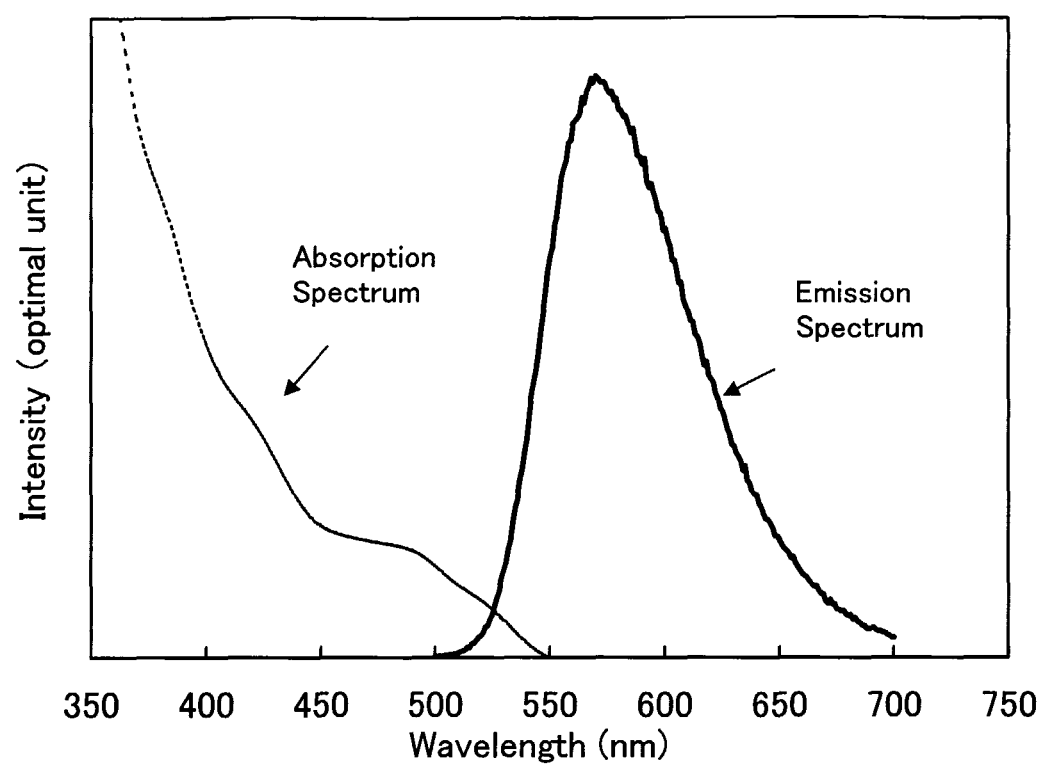
FIG. 10 is a graph showing an absorption spectrum and an emission spectrum of an organometallic complex according to the present invention, which is synthesized in Synthesis Example 1.

Moreover, Ir(Fdppr)₂(acac) was dissolved in dichloromethane, and then, measurement of an absorption spectrum (using an ultraviolet-visible spectrophotometer by JASCO Corporation, V-550) and an emission spectrum (using a spectrofluorometer by Hamamatsu Photonics K.K., FS 920) of Ir(Fdppr)₂(acac) at a room temperature was conducted. The results are shown in FIG. 10. In FIG. 10, a horizontal axis represents wavelength (nm), and a vertical axis represents intensity (an arbitrary unit). As can be seen from FIG. 10, the organometallic complex Ir(Fdppr)₂(acac) according to the present invention has absorption peaks at 380 nm, 420 nm, 490 nm, and 525 nm. In addition, the emission spectrum of Ir(Fdppr)₂(acac) showed an emission peak at 570 nm, and emitted light was visible as yellow light.

Further, a gas containing oxygen was injected into a dichloromethane solution containing Ir(Fdppr)₂(acac), and then, the emission intensity of Ir(Fdppr)₂(acac) was examined when Ir(Fdppr)₂(acac) with dissolved oxygen was made to emit light. Furthermore, argon was injected into a dichloromethane solution containing Ir(Fdppr)$_2$(acac), and the emission intensity of Ir(Fdppr)$_2$(acac) was examined when Ir(Fdppr)$_2$(acac) with dissolved argon was made to emit light. From the results, it was determined that luminescence of Ir(Fdppr)$_2$(acac) shows the same tendency as luminescence of a phosphorescent substance, where the tendency is that the emission intensity is stronger in the state with dissolved argon than with dissolved oxygen. Accordingly, luminescence of Ir(Fdppr)$_2$(acac) was confirmed to be phosphorescence.

Synthesis Example 2

A synthesis method of an organometallic complex according to the present invention represented by the structural formula (16) (referred to as (acetylacetonato)bis[2,3-bis(4-fluorophenyl)-5-methylpyrazinato]iridium(III)) will be described.

[Step 1: Synthesis of a Ligand (Abbreviation: HFDPPR-Me))

First, with ethanol as a solvent, 5.31 g of 4,4'-difluorobenzil (by Tokyo Chemical Industry Co., Ltd.) and 1.60 g of 1,2-diaminopropane (by Tokyo Chemical Industry Co., Ltd.) were mixed, and the mixture was refluxed for three hours. After reaction, a reaction solution was condensed by using an evaporator, and an obtained residue was recrystallized by using ethanol; thus, 2,3-bis(4-fluorophenyl)-5-methyl-5,6-dihydropyrazine was obtained (light yellow powder, yield: 86%).

Then, with ethanol as a solvent, 5.29 g of 2,3-bis(4-fluorophenyl)-5-methyl-5,6-dihydropyrazine and 6.04 g of iron (III) chloride were mixed, and the mixture was stirred while heating in a gentle manner for three hours. A solid obtained by adding water to a solution after reaction was purified by column chromatography using a dichloromethane as a developing solvent, and a ligand referred to as 2,3-bis(4-fluorophenyl)-5-methylpyrazine (abbreviation: HFDPPR-Me) was obtained (milk-white powder, yield: 72%). A synthesis scheme (d-1) relating to the synthesis of Step 1 is shown below.

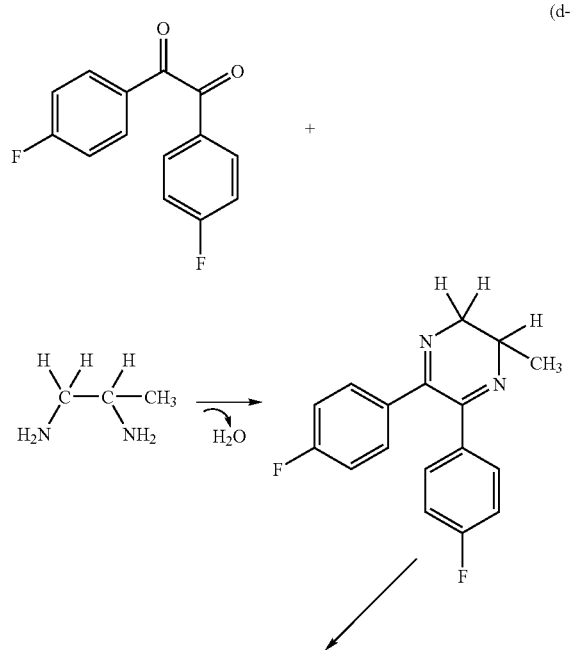

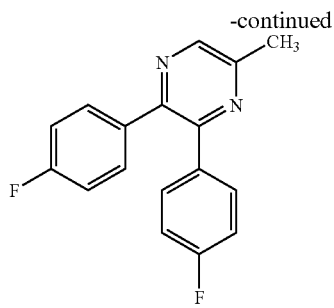

[Step 2: Synthesis of a Binuclear Complex (Abbreviation: [Ir(FDPPR-Me)$_2$Cl]$_2$)]

Subsequently, with a mixture of 30 mL of 2-ethoxyethanol and 10 mL of water as a solvent, 3.75 g of a ligand HFDPPR-Me and 1.59 g of iridium (III) chloride hydrochloride hydrate (IrCl$_3$.HCl.H$_2$O) (by Sigma-Aldrich) were mixed. The mixture was refluxed in a nitrogen atmosphere for 16 hours to obtain a binuclear complex [Ir(FDPPR-Me)$_2$Cl]$_2$ (reddish brown powder, yield: 87%). A synthesis scheme (d-2) relating to the synthesis of Step 2 is shown below.

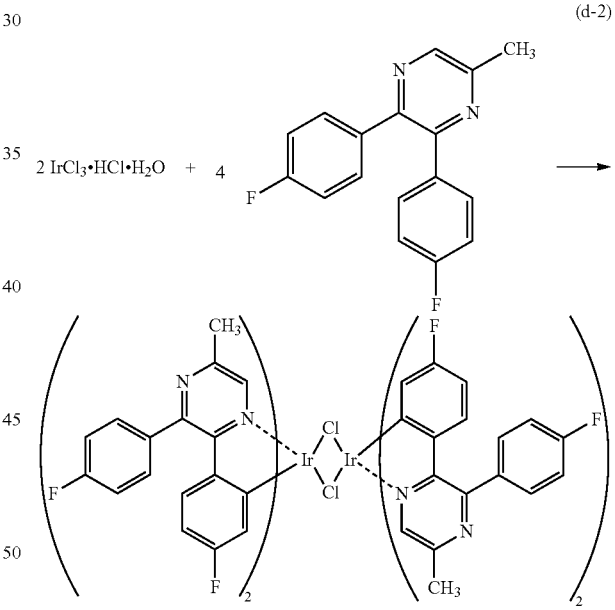

[Step 3: Synthesis of an Organometallic Complex According to the Present Invention (Abbreviation: [Ir(Fdppr-Me)$_2$(acac)])]

Further, with 30 mL of 2-ethoxyethanol as a solvent, 1.91 g of [Ir(FDPPR-Me)$_2$Cl]$_2$, 0.37 mL of acetylacetone (abbreviation: Hacac), and 1.28 g of sodium carbonate were mixed. The mixture was refluxed in a nitrogen atmosphere for 16 hours to obtain yellow orange powder (yield: 34%). A synthesis scheme (d-3) relating to the synthesis of Step 3 is shown below.

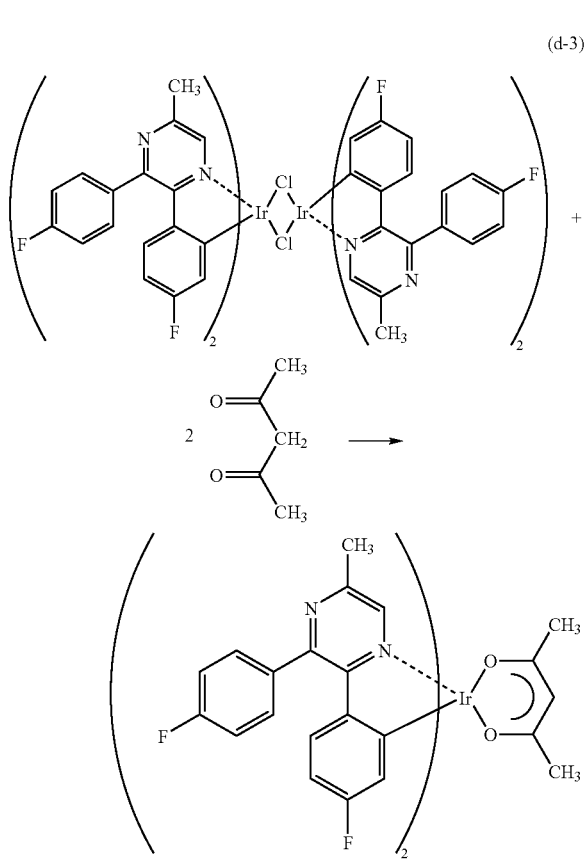

(d-3)

Figure 11:
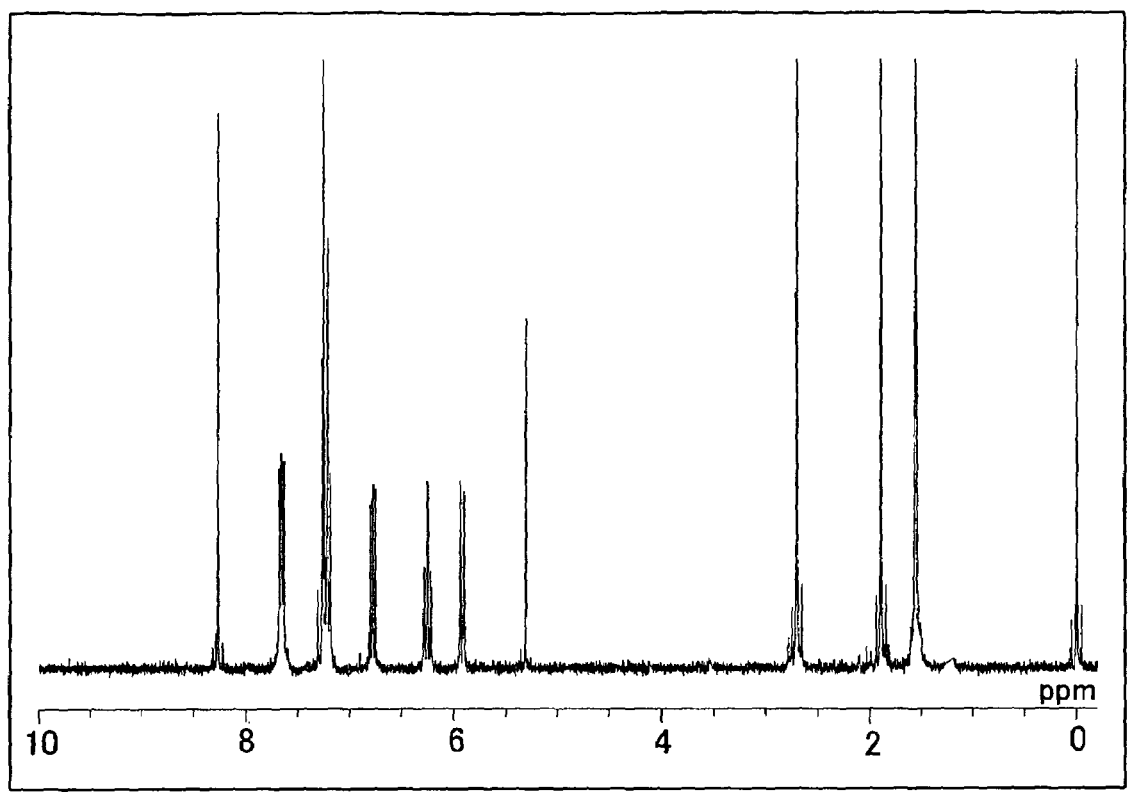
FIG. 11 is a graph showing $^1$H-NMR of an organometallic complex according to the present invention, which is synthesized in Synthesis Example 2.

The obtained yellow orange powder was analyzed by nuclear magnetic resonance spectroscopy ($^1$H-NMR) and a result as shown below was obtained. The product was identified to be Ir(Fdppr-Me)$_2$(acac) represented by the structural formula (16) which is one of organometallic complexes according to the present invention. The $^1$H-NMR chart is shown in FIG. 11.

$^1$H-NMR.δ(CDCl$_3$): 8.27(s,2H), 7.66(dd,4H), 7.22(m, 4H), 6.78(dd,2H), 6.26(td,2H), 5.92(dd,2H), 5.31(s,1H), 2.70(s,6H), 1.89(s,6H)

In addition, measurement of the decomposition temperature $T_d$ of the obtained organometallic complex Ir(Fdppr-Me)$_2$(acac) according to the present invention was conducted by a thermo-gravimetric/differential thermal analyzer (by Seiko Instruments Inc., TG/DTA-320) to find $T_d$=291° C., and thus, it was determined that the Ir(Fdppr-Me)$_2$(acac) shows favorable heat resistance.

Figure 12:
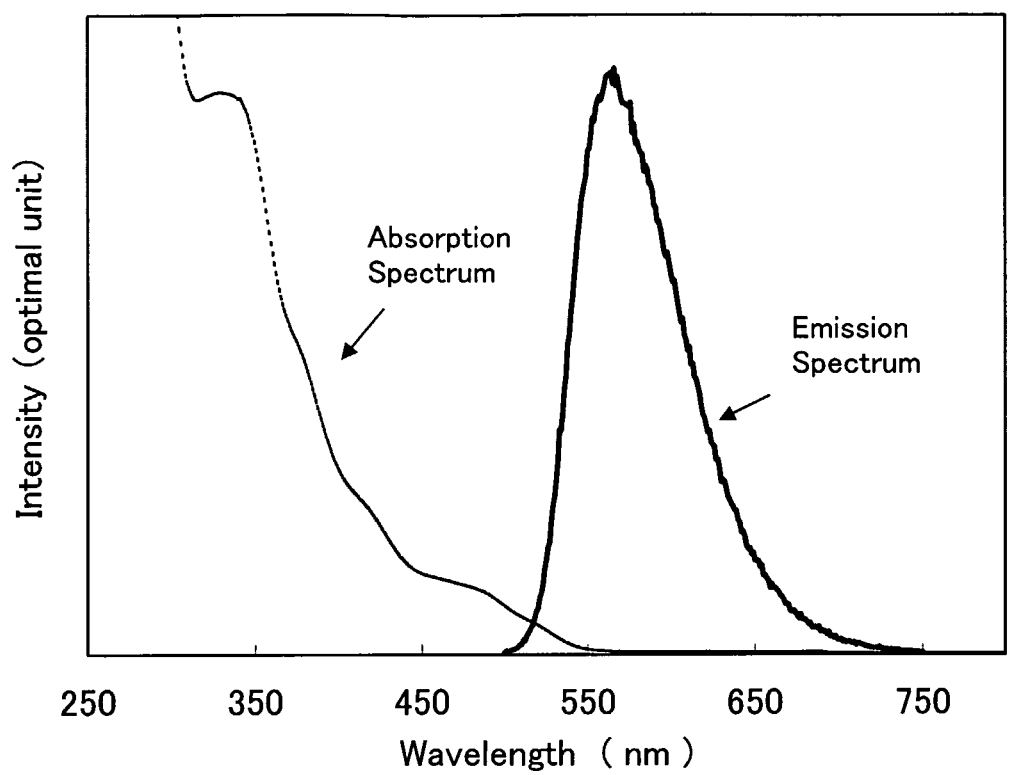
FIG. 12 is a graph showing an absorption spectrum and an emission spectrum of an organometallic complex according to the present invention, which is synthesized in Synthesis Example 2.

Moreover, Ir(Fdppr-Me)$_2$(acac) is dissolved in dichloromethane, and then, measurement of an absorption spectrum (using an ultraviolet-visible spectrophotometer by JASCO Corporation, V-550) and an emission spectrum (using a spectrofluorometer by Hamamatsu Photonics K.K., FS 920) of Ir(Fdppr-Me)$_2$(acac) at a room temperature was conducted. The results are shown in FIG. 12. In FIG. 12, a horizontal axis represents wavelength (nm), and a vertical axis represents intensity (an arbitrary unit). As can be seen from FIG. 12, the organometallic complex Ir(Fdppr-Me)$_2$(acac) according to the present invention has absorption peaks at 380 nm, 420 nm, 485 nm, and 520 nm. In addition, the emission spectrum of Ir(Fdppr-Me)$_2$(acac) showed an emission peak at 564 nm, and emitted light was visible as yellow light.

Further, a gas containing oxygen was injected into a dichloromethane solution containing Ir(Fdppr-Me)$_2$(acac), and then, the emission intensity of Ir(Fdppr-Me)$_2$(acac) was examined when the Ir(Fdppr-Me)$_2$(acac) with dissolved oxygen was made to emit light. Furthermore, argon was injected into the dichloromethane solution containing Ir(Fdppr-Me)$_2$(acac), and the emission intensity of Ir(Fdppr-Me)$_2$(acac) was examined when Ir(Fdppr-Me)$_2$(acac) with dissolved argon was made to emit light. From the results, it was determined that luminescence of Ir(Fdppr-Me)$_2$(acac) shows the same tendency as luminescence of a phosphorescent substance, where the tendency is that the emission intensity is stronger in the state with dissolved argon than with dissolved oxygen. Accordingly, luminescence of Ir(Fdppr-Me)$_2$(acac) was confirmed to be phosphorescence.

Synthesis Example 3

A synthesis method of an organometallic complex according to the present invention represented by the structural formula (56) referred to as bis[2,3-bis(4-fluorophenyl)-5-methylpyrazinato][tetrakis(1-pyrazolyl)borato]iridium(III) (abbreviation: Ir(Fdppr-Me)$_2$(bpz$_4$)) will be described.

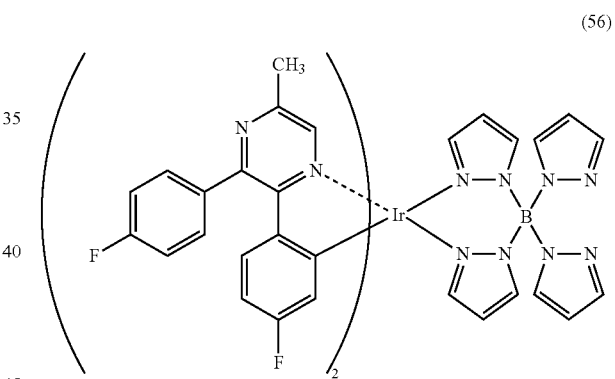

(56)

First, 1.00 g of the binuclear complex [Ir(FDPPR-Me)$_2$Cl]$_2$ that was obtained in the Step 2 of the synthesis example 2 was suspended in 40 mL of dichloromethane. Then, 0.40 g of silver trifluoromethanesulfonate was dissolved in 40 mL of methanol as a solvent, and this solution was dropped to the suspension. After dropping, the suspension was stirred at a room temperature for two hours, and centrifugation was further performed. A supernatant solution of the suspension, which was obtained by centrifugation, was taken out by decantation, and it was condensed and exsiccated. Then, with 30 mL of acetonitrile as a solvent, a solid that was obtained after condensation and exsiccation as described above and 0.70 g of tetrakis(1-pyrazolyl)borate potassium salt (by Acros Organics) were mixed. The mixture was refluxed in a nitrogen atmosphere for 18 hours to obtain yellow powder (yield: 50%). A synthesis scheme (e) of this synthesis is shown below.

(e)

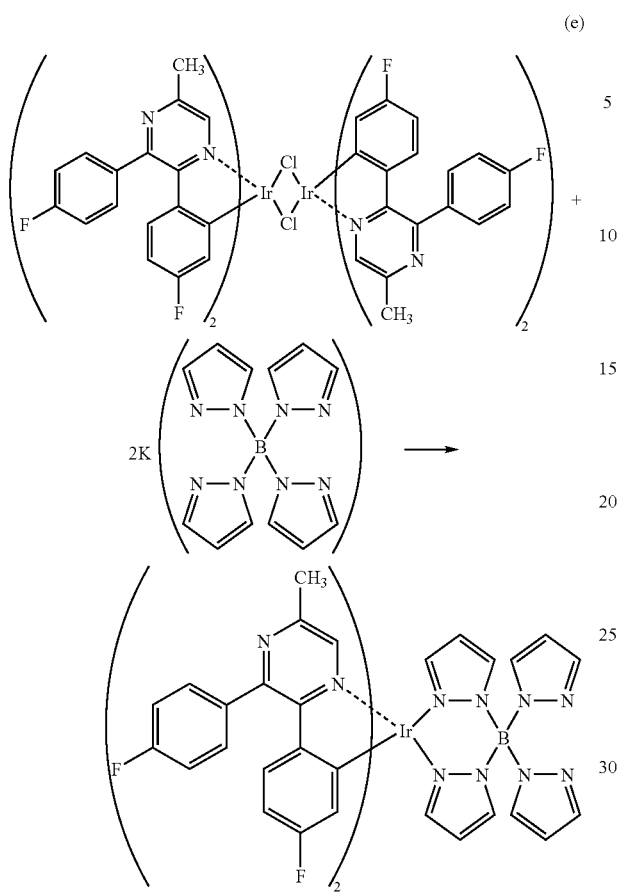

Figure 23:
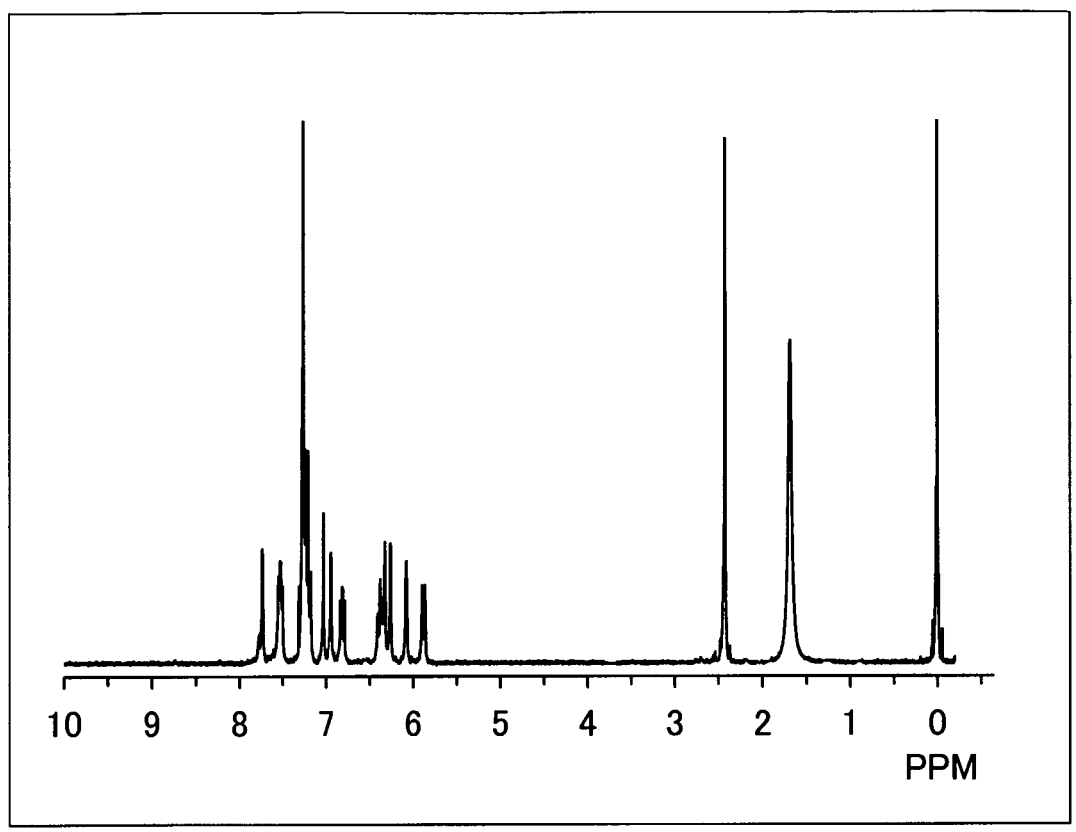
FIG. 23 is a graph showing $^1$H-NMR of an organometallic complex according to the present invention, which is synthesized in Synthesis Example 3.

The obtained yellow powder was analyzed by nuclear magnetic resonance spectroscopy (¹H-NMR) and a result as shown below was obtained. The product was identified to be Ir(Fdppr-Me)₂(bpz₄) represented by the structural formula (56), which is one of organometallic complexes according to the present invention. The ¹H-NMR chart is as shown in FIG. 23.

¹H-NMR.δ(CDCl₃): 7.23(m,2H), 7.53(m,4H), 7.24-7.18 (m,5H), 7.03(s,2H), 6.94(m,2H), 6.81(dd,2H), 6.41-6.26(m, 7H), 6.08(m, 2H), 5.88(dd,2H), 2.43(s,6H)

In addition, measurement of the decomposition temperature $T_d$ of the obtained organometallic complex Ir(Fdppr-Me)₂(bpz₄) according to the present invention was conducted by a thermo-gravimetric/differential thermal analyzer (by Seiko Instruments Inc., TG/DTA-320) to find $T_d$=330° C., and thus, it was determined that Ir(Fdppr-Me)₂(bpz₄) shows favorable heat resistance.

Figure 24:
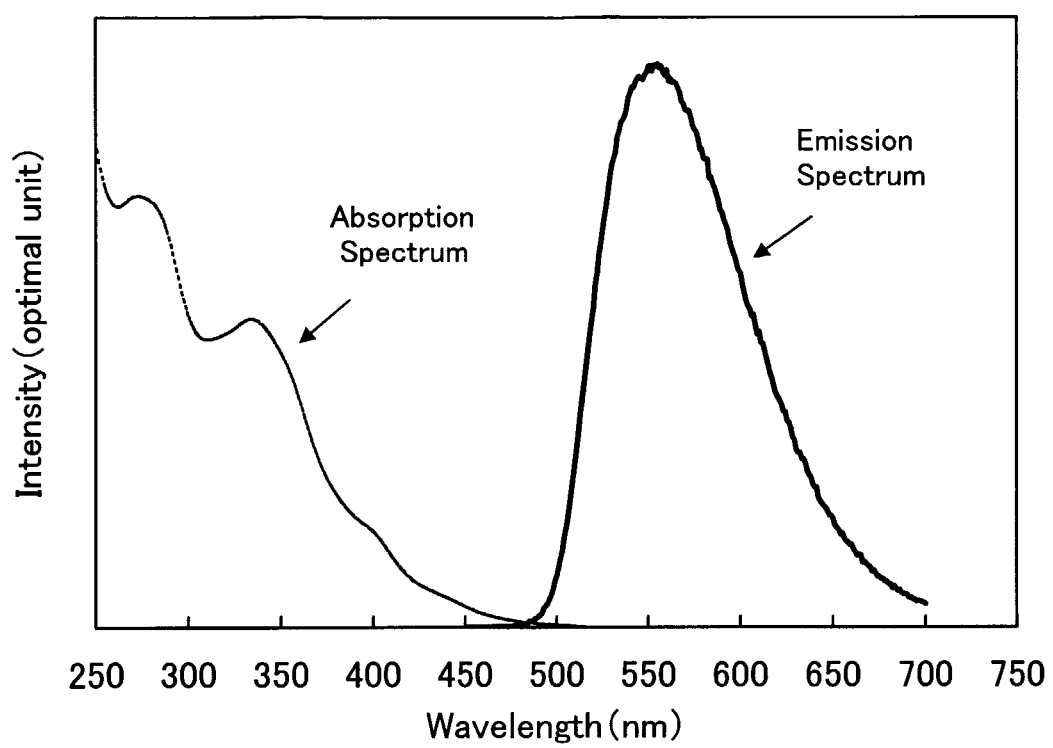
FIG. 24 is a graph showing an absorption spectrum and an emission spectrum of an organometallic complex according to the present invention, which is synthesized in Synthesis Example 3.

Moreover, measurement of an absorption spectrum (using an ultraviolet-visible spectrophotometer by JASCO Corporation, V-550) and an emission spectrum (using a spectrofluorometer by Hamamatsu Photonics K. K., FS 920) of Ir(Fdppr-Me)₂(bpz₄) at a room temperature was conducted by using a deaerated dichloromethane solution. The results are shown in FIG. 24. In FIG. 24, a horizontal axis represents wavelength (nm), and a vertical axis represents intensity (an arbitrary unit). As can be seen from FIG. 24, the organometallic complex Ir(Fdppr-Me)₂(bpz₄) according to the present invention has absorption peaks at 273 nm, 334 nm, 403 nm, and 446 nm. In addition, the emission spectrum of Ir(Fdppr-Me)₂(bpz₄) showed an emission peak at 553 nm, and emitted light was visible as yellow green light.

Synthesis Example 4

A synthesis method of an organometallic complex according to the present invention represented by the structural formula (28) referred to as bis[2,3-bis(4-fluorophenyl)-5-methylpyrazinato](picolinato)iridium(III) (abbreviation: Ir(Fdppr-Me)₂(pic)) will be described.

First, with 40 mL of 2-ethoxyethanol as a solvent, 2.31 g of the binuclear complex [Ir(FDPPR-Me)₂Cl]₂ that was obtained in Step 2 of the synthesis example 2 and 1.33 g of picolnic acid (by Tokyo Chemical Industry Co., Ltd.) were mixed. The mixture was refluxed in a nitrogen atmosphere for 20 hours to obtain yellow powder (yield: 91%). A synthesis scheme (f) of this synthesis is shown below.

(f)

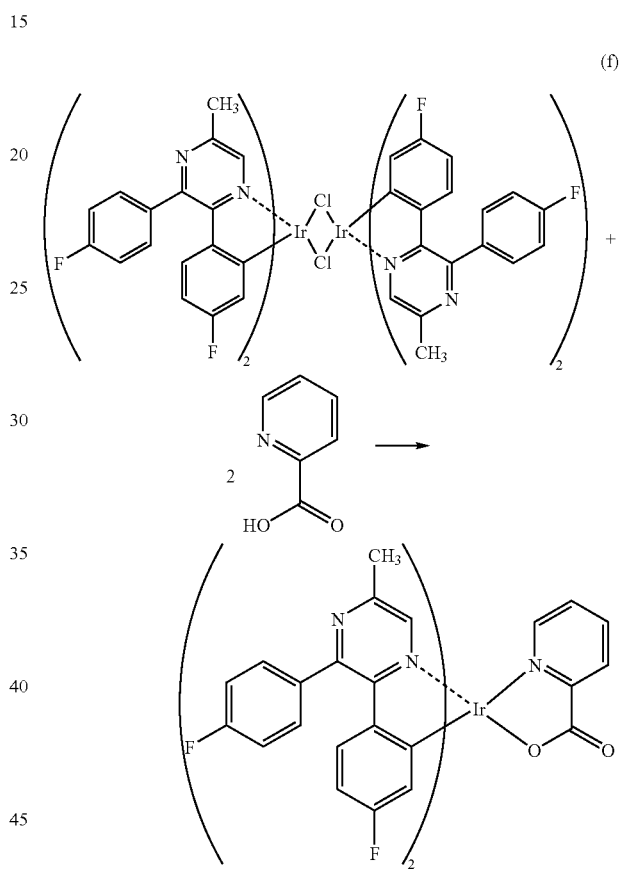

Figure 25:
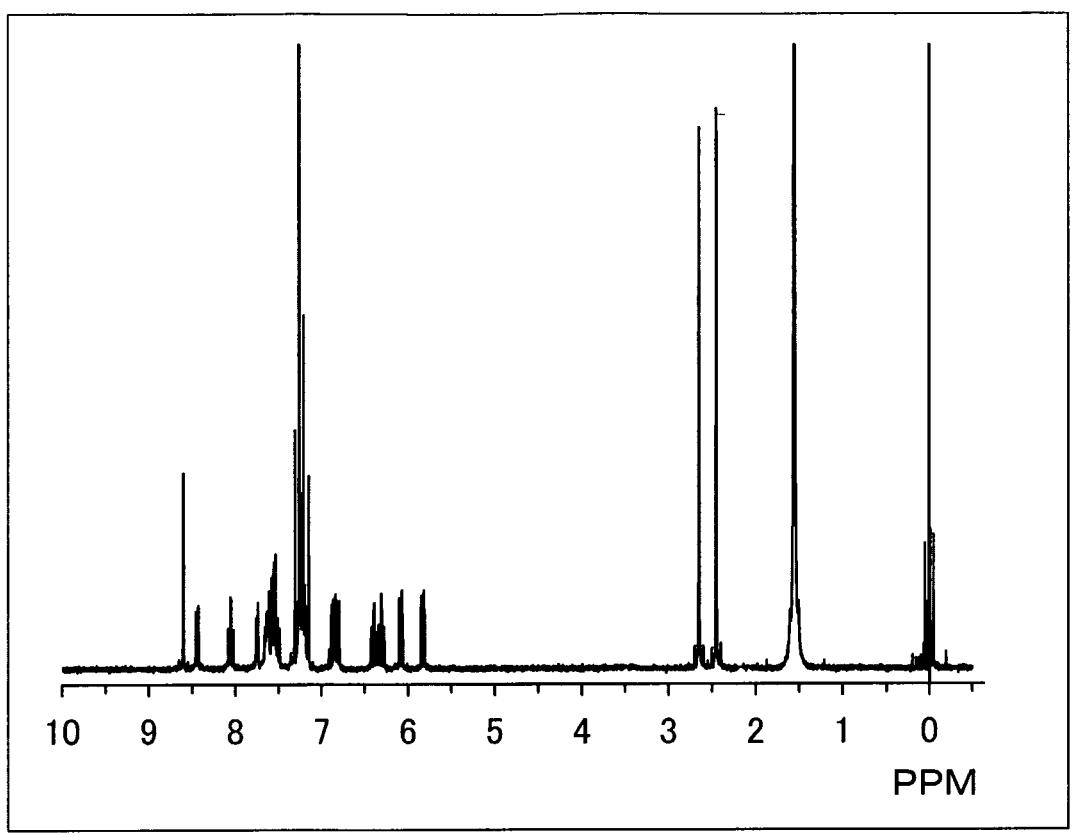
FIG. 25 is a graph showing $^1$H-NMR of an organometallic complex synthesized in Synthesis Example 4.

The obtained yellow powder was analyzed by nuclear magnetic resonance spectroscopy (¹H-NMR) and a result as shown below was obtained. The product was identified to be Ir(Fdppr-Me)₂(pic) represented by the structural formula (28), which is one of organometallic complexes according to the present invention. The ¹H-NMR chart is shown in FIG. 25.

¹H-NMR.δ(CDCl₃): 8.60(s,1H), 8.44(d,1H), 8.05(td,1H), 7.74(d,1H), 7.65-7.49(m,5H), 7.31-7.15(m,5H), 6.88-6.79 (m,2H), 6.39(td,1H), 6.31(td,1H), 6.08(dd,1H), 5.83(dd,1H), 2.65(s,3H), 2.45(s,3H)

In addition, measurement of the decomposition temperature $T_d$ of the obtained organometallic complex Ir(Fdppr-Me)₂(pic) according to the present invention was conducted by a thermo-gravimetric/differential thermal analyzer (by Seiko Instruments Inc., TG/DTA-320) to find $T_d$=346° C., and thus, it was determined that Ir(Fdppr-Me)₂(pic) shows favorable heat resistance.

Figure 26:
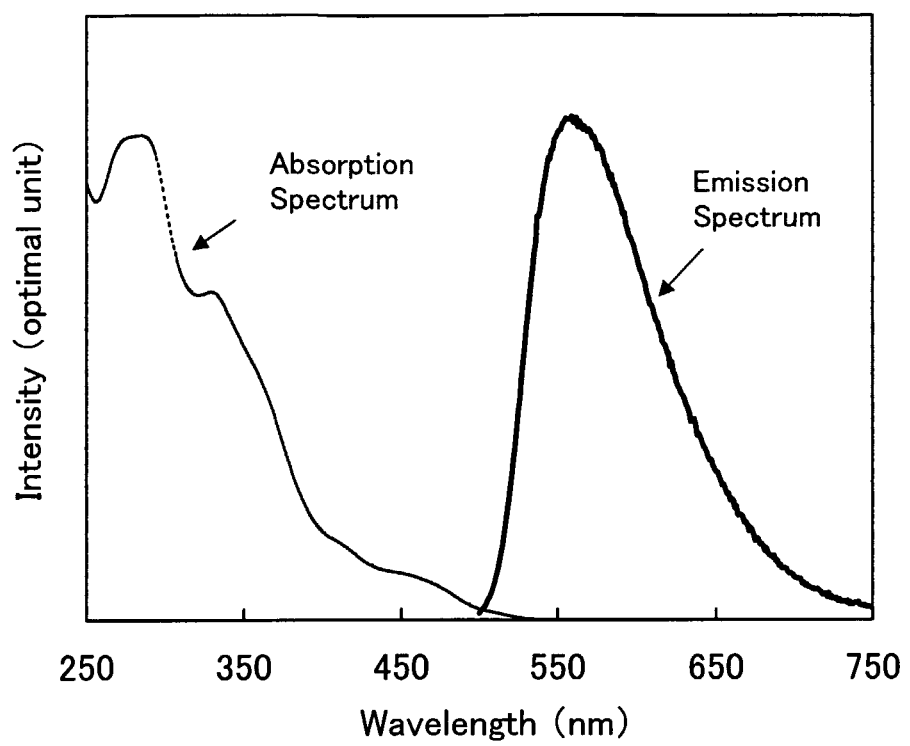
FIG. 26 is a graph showing an absorption spectrum and an emission spectrum of an organometallic complex synthesized in Synthesis Example 4.

Moreover, measurement of an absorption spectrum (using an ultraviolet-visible spectrophotometer by JASCO Corporation, V-550) and an emission spectrum (using a spectrofluorometer by Hamamatsu Photonics K.K., FS 920) of Ir(Fdppr-Me)₂(pic) at a room temperature was conducted by using a deaerated dichloromethane solution. The results are shown in FIG. 26. In FIG. 26, a horizontal axis represents wavelength (nm), and a vertical axis represents intensity (an arbitrary unit). As can be seen from FIG. 26, the organometallic complex Ir(Fdppr-Me)₂(pic) according to the present invention has absorption peaks at 330 nm, 360 nm, 410 nm, 455 nm and 505 nm. In addition, the emission spectrum of Ir(Fdppr-Me)₂(pic) showed an emission peak at 558 nm, and emitted light was visible as yellow light.

Synthesis Example 5

A synthesis method of an organometallic complex according to the present invention represented by any of the general formulas (1) to (18), more specifically, represented the structural formula (57), referred to as bis[2,3-bis(4-fluorophenyl)-5-isopropylpyrazinato](picolinato)iridium(III) (abbreviation: Ir(Fdppr-iPr)₂(pic)) will be described.

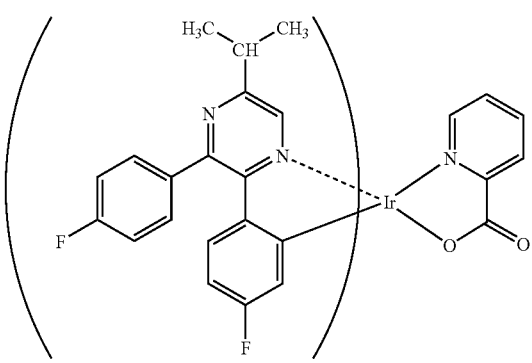
(57)

[Step 1: Synthesis of a Ligand (Abbreviation: HFDPPR-iPr)]

First, with 150 mL of dehydrated ethanol as a solvent, 5.36 g of 4,4'-difluorobenzil (by Tokyo Chemical Industry Co., Ltd.) and 1.31 g of anhydrous ethylenediamine (by Tokyo Chemical Industry Co., Ltd.) were mixed, and the mixture was refluxed in a nitrogen atmosphere for three hours. After cooling a reaction solution to a room temperature, 1.60 g of acetone and 1.47 g of potassium hydroxide were added into the reaction solution. Further, the reaction solution was refluxed in a nitrogen atmosphere for six hours. After reaction, water was added to the reaction solution, and an organic layer was extracted by using ethyl acetate. The obtained organic layer was dried with sodium sulfate and filtered, and solvent of filtrate was removed. An obtained residue was purified by silica gel column chromatography using dichloromethane as a developing solvent, and 4.00 g of a ligand referred to as 2,3-bis(4-fluorophenyl)-5-isopropylpyrazine (HFDPPR-iPr) was obtained (light yellow oily matter, yield: 59%). A synthesis scheme (g-1) relating to the synthesis of Step 1 is shown below.

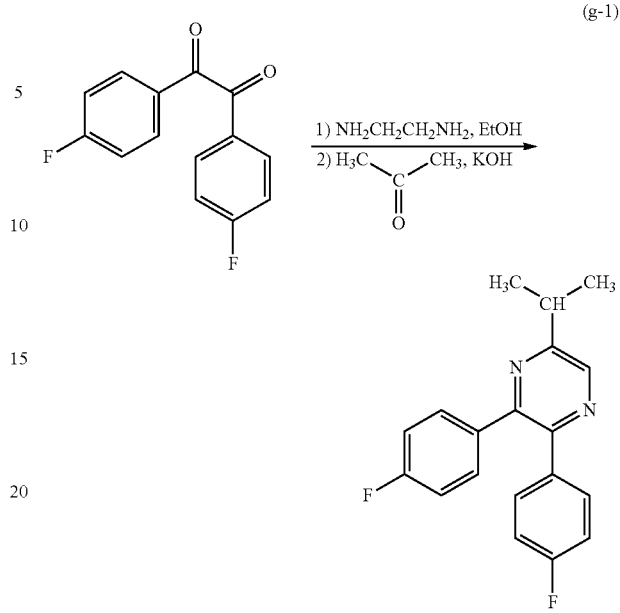
(g-1)

[Step 2: Synthesis of a Binuclear Complex (Abbreviation: [Ir(FDPPR-iPr)₂Cl]₂)]

Subsequently, with a mixture of 30 mL of 2-ethoxyethanol and 10 mL of water as a solvent, 4.00 g of HFDPPR-iPr that is the ligand obtained in Step 1 and 1.61 g of iridium (III) chloride hydrate (IrCl₃.H₂O) (by Sigma-Aldrich) were mixed. The mixture was refluxed in a nitrogen atmosphere for 19 hours to obtain a binuclear complex [Ir(FDPPR-iPr)₂Cl]₂ (orange powder, yield: 72%). A synthesis scheme (g-2) relating to the synthesis of Step 2 is shown below.

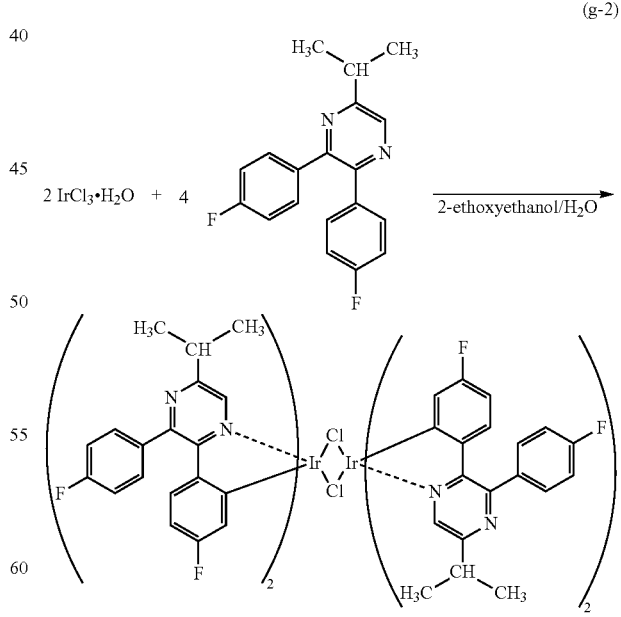
(g-2)

[Step 3: Synthesis of an Organometallic Complex According to the Present Invention (Abbreviation: Ir(Fdppr-iPr)₂(pic))]

Further, 25 mL of dichloromethane was mixed with 1.61 g of the binuclear complex [Ir(FDPPR-iPr)₂Cl]₂) obtained in Step 2 and 0.94 g of picolinic acid. The mixture was refluxed in a nitrogen atmosphere for 18 hours to obtain bright golden yellow powder (yield: 90%). A synthesis scheme (g-3) relating to the synthesis of Step 3 is shown below.

has absorption peaks at 328 nm, 410 nm, 453 nm, and 509 nm. In addition, the emission spectrum of Ir(Fdppr-iPr)$_2$(pic) showed an emission peak at 559 nm, and emitted light was visible as yellow light.

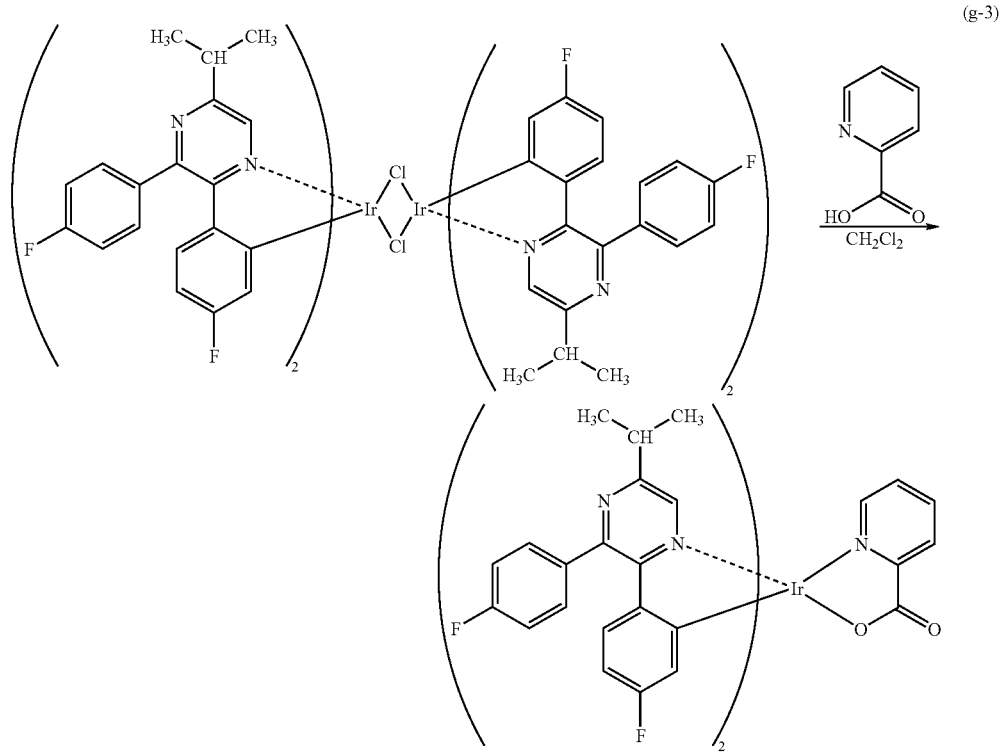

(g-3)

Figure 32:
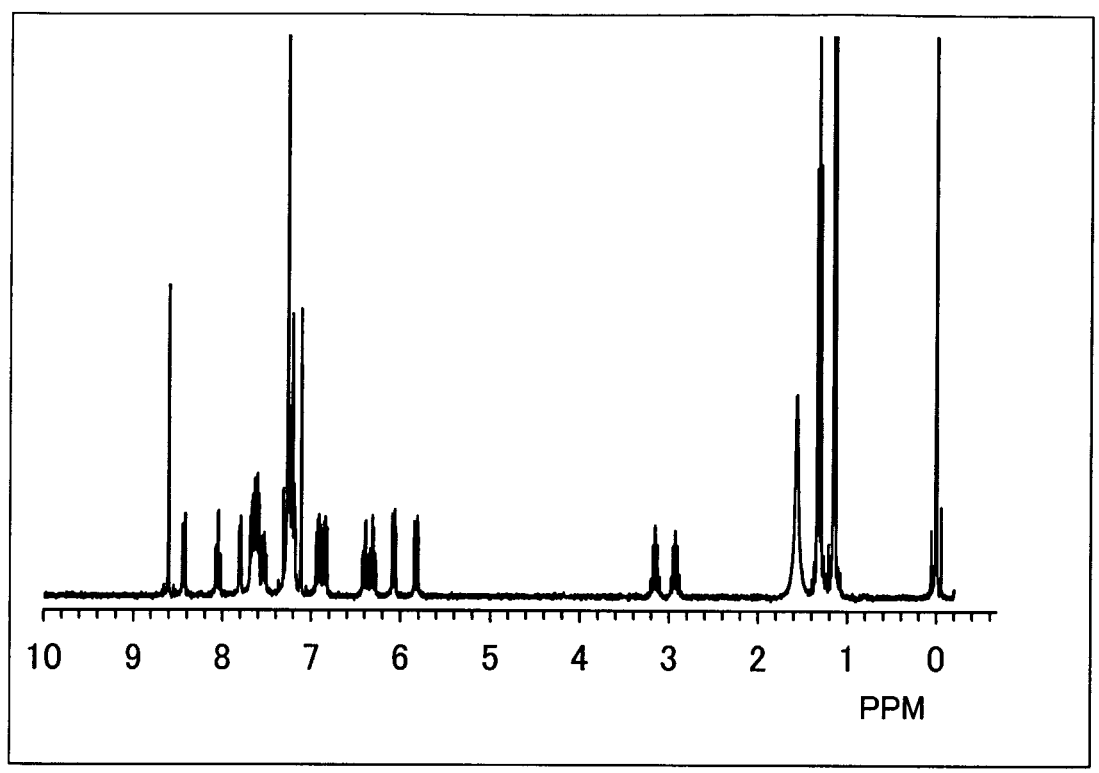
FIG. 32 is a graph showing $^1$H-NMR of an organometallic complex synthesized in Synthesis Example 5.

The obtained bright golden yellow powder was analyzed by nuclear magnetic resonance spectroscopy ($^1$H-NMR) and a result as shown below was obtained. The product was identified to be Ir(Fdppr-iPr)$_2$(pic) represented by the structural formula (57) which is one of organometallic complexes according to the present invention. The $^1$H-NMR chart is shown in FIG. 32.

$^1$H-NMR.δ(CDCl$_3$): 1.15(d,6H), 1.32(t,6H), 2.93(quin, 1H), 3.16(quin,1H), 5.82(dd,1H), 6.07(dd,1H), 6.31(td,1H), 6.38(td,1H), 6.85(dd,1H), 6.92(dd,1H), 7.11-7.32(m,5H), 7.53(m,1H), 7.59-7.69(m,4H), 7.80(d,1H), 8.05(td,1H), 8.43(d,1H), 8.60(s,1H)

In addition, measurement of the decomposition temperature $T_d$ of the obtained Ir(Fdppr-iPr)$_2$(pic) according to the present invention was conducted by a thermo-gravimetric/differential thermal analyzer (by Seiko Instruments Inc., TG/DTA-320) to find $T_d$=348° C., and thus, it was determined that Ir(Fdppr-iPr)$_2$(pic) shows favorable heat resistance.

Figure 33:
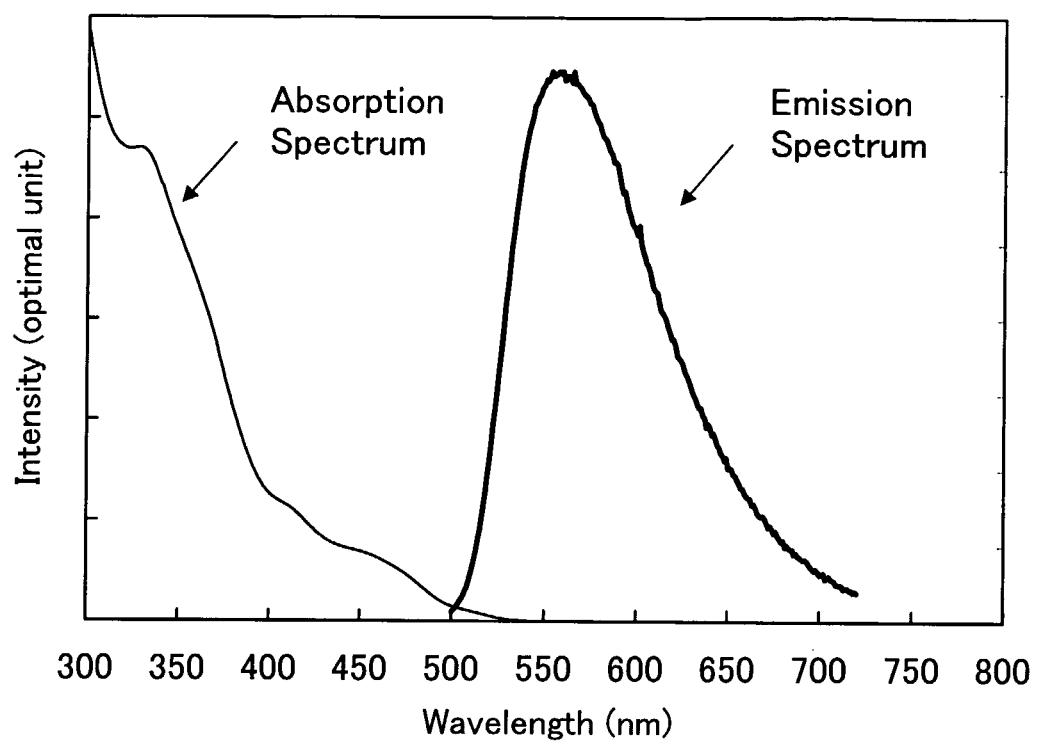
FIG. 33 is a graph showing an absorption spectrum and an emission spectrum of an organometallic complex synthesized in Synthesis Example 5.

Moreover, measurement of an absorption spectrum (using an ultraviolet-visible spectrophotometer by JASCO Corporation, V-550) and an emission spectrum (using a spectrofluorometer by Hamamatsu Photonics K.K., FS 920) of Ir(Fdppr-iPr)$_2$(pic) at a room temperature was conducted by using deaerated dichloromethane solution. The results are shown in FIG. 33. In FIG. 33, a horizontal axis represents wavelength (nm), and a vertical axis represents intensity (an arbitrary unit). As can be seen from FIG. 33, the organometallic complex Ir(Fdppr-iPr)$_2$(pic) according to the present invention Synthesis Example 6

A synthesis method of an organometallic complex according to the present invention referred to as bis[2,3-bis(4-trifluoromethylphenyl)pyrazinato](picolinato)iridium(III) (abbreviation: Ir(CF$_3$dppr-Me)$_2$(pic)) represented by the structural formula (29) will be described.

[Step 1: Synthesis of a Ligand (Abbreviation: CF$_3$DPPR-Me)]

First, with 150 mL of dehydrated ethanol as a solvent, 5.07 g of 4,4'-bis(trifluoromethyl)benzil and 1.09 g of 1,2-diaminopropane were mixed, and the mixture was refluxed in a nitrogen atmosphere for four hours. After reaction, a reaction solution was condensed under reduced pressure, and an obtained residue was recrystallized by using ethanol to obtain 2-methyl-5,6-bis(4-trifluoromethylphenyl)-2,3-dihydropyrazine (light yellow crystal, yield: 87%). Further, with 100 mL of dehydrated ethanol as a solvent, 5.05 g of 2-methyl-5,6-bis(4-trifluoromethylphenyl)-2,3-dihydropyrazine that is obtained as described above and 4.26 g of iron (III) chloride were mixed, and the mixture was heated in a nitrogen atmosphere for two hours in a gentle manner. After reaction, water was added into a reaction solution for dilution, and extraction was performed with ether. An extraction solution was dried with magnesium sulfate and filtered, and solvent of filtrate was removed. An obtained residue was recrystallized with ethanol to obtain 5-methyl-2,3-bis(4-trifluoromethylphenyl) pyrazine (CF$_3$DPPR-Me) that is a ligand (white powder, yield: 52%). A synthesis scheme (h-1) relating to the synthesis of Step 1 is shown below.

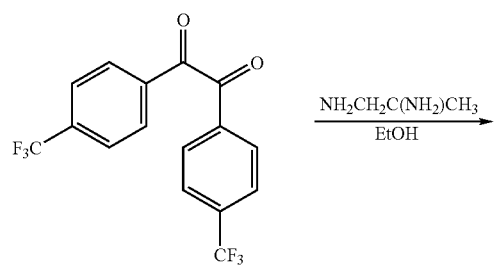

(h-1)

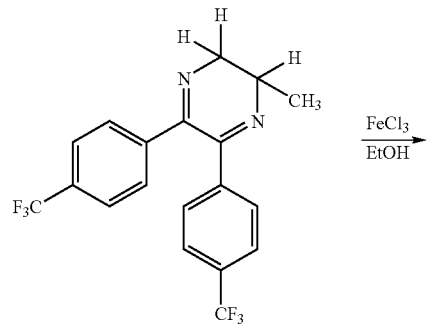

[Step 2: Synthesis of a Binuclear Complex ([Ir(CF₃DPPR-Me)₂Cl]₂)]

Subsequently, with a mixture of 30 mL of 2-ethoxyethanol and 10 mL of water as a solvent, 1.89 g of CF₃DPPR-Me that is a ligand obtained in Step 1 and 0.83 g of iridium (III) chloride hydrate (IrCl₃·H₂O) (by Sigma-Aldrich) were mixed. The mixture was refluxed in a nitrogen atmosphere for 16 hours to obtain a binuclear complex [Ir(CF₃DPPR-Me)₂Cl]₂ (orange powder, yield: 47%). A synthesis scheme (h-2) relating to the synthesis of Step 2 is shown below.

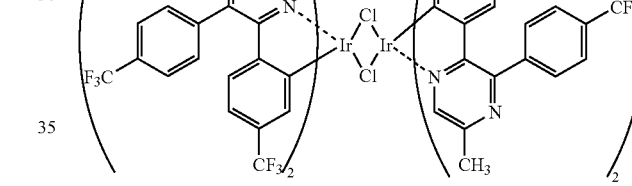

[Step 3: Synthesis of an Organometallic Complex According to the Present Invention (Abbreviation: Ir(CF₃dppr-Me)₂(pic))]

Further, 30 mL of dichloromethane was mixed with 1.29 g of the binuclear complex [Ir(CF₃DPPR-Me)₂Cl]₂ obtained in Step 2 and 0.64 g of picolinic acid. The mixture was refluxed in a nitrogen atmosphere for 17 hours to obtain bright golden yellow powder (yield: 47%). A synthesis scheme (h-3) relating to the synthesis of Step 3 is shown below.

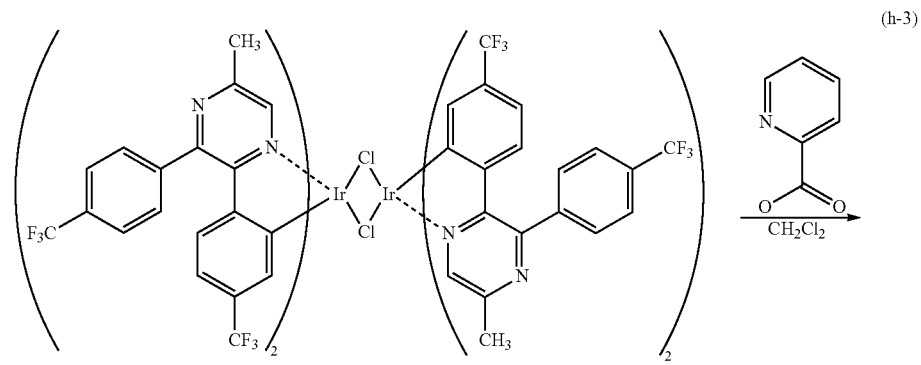

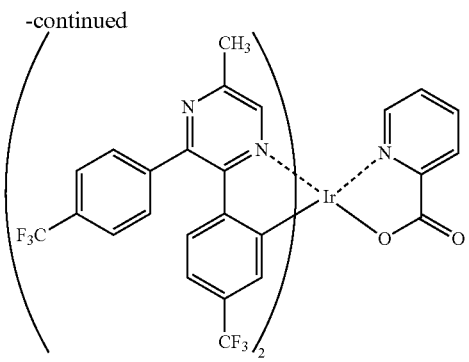

Figure 43:
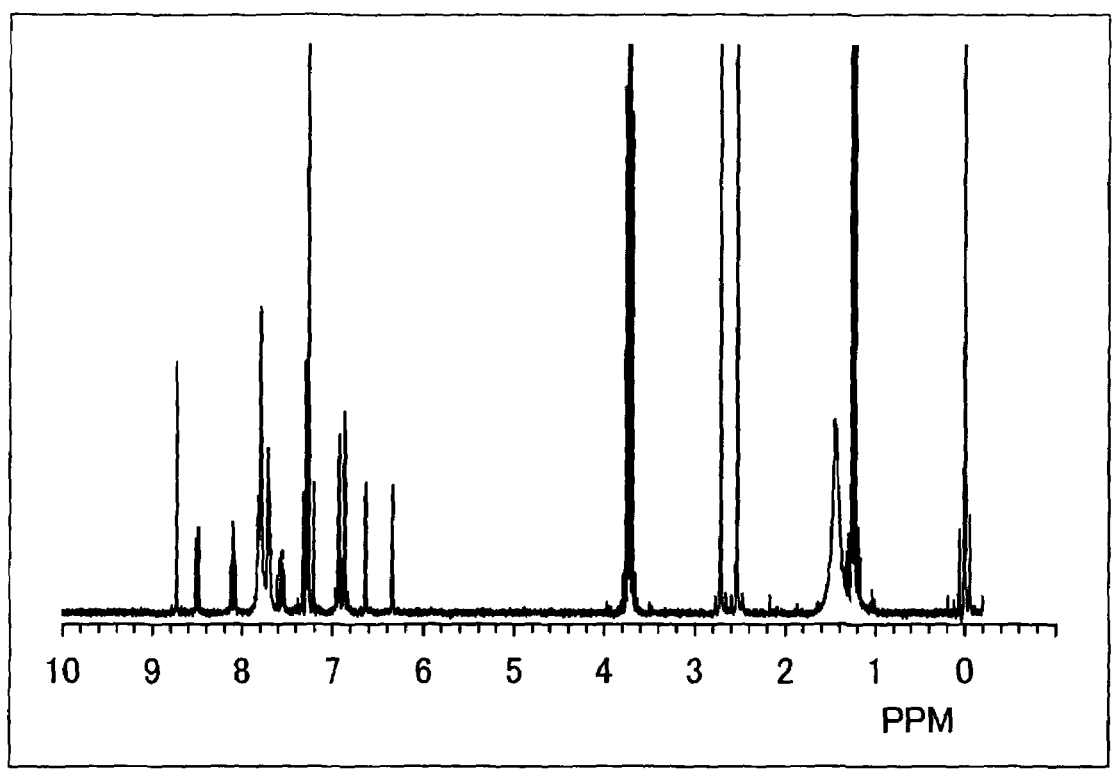
FIG. 43 is a graph showing $^1$H-NMR of an organometallic complex synthesized in Synthesis Example 6.

The obtained bright golden yellow powder was analyzed by nuclear magnetic resonance spectroscopy ($^1$H-NMR) and a result as shown below was obtained. The product was identified to be Ir(CF$_3$dppr-Me)$_2$(pic) represented by the structural formula (29), which is one of organometallic complexes according to the present invention. The $^1$H-NMR chart is shown in FIG. 43.

$^1$H-NMR.δ(CDCl$_3$): 2.53(s,1H), 2.71(s,1H), 6.34(s,1H), 6.63(s,1H), 6.82-6.96(m,4H), 7.29(m,1H), 7.55(m,1H), 7.68-7.82(m,9H), 8.10(td,1H), 8.50(d,1H), 8.73(s, 1H)

In addition, measurement of the decomposition temperature T$_d$ of the obtained Ir(CF$_3$dppr-Me)$_2$(pic) according to the present invention was conducted by a thermo-gravimetric/differential thermal analyzer (by Seiko Instruments Inc., TG/DTA-320) to find T$_d$=338° C., and thus, it was determined that Ir(CF$_3$dppr-Me)$_2$(pic) shows favorable heat resistance.

Figure 44:
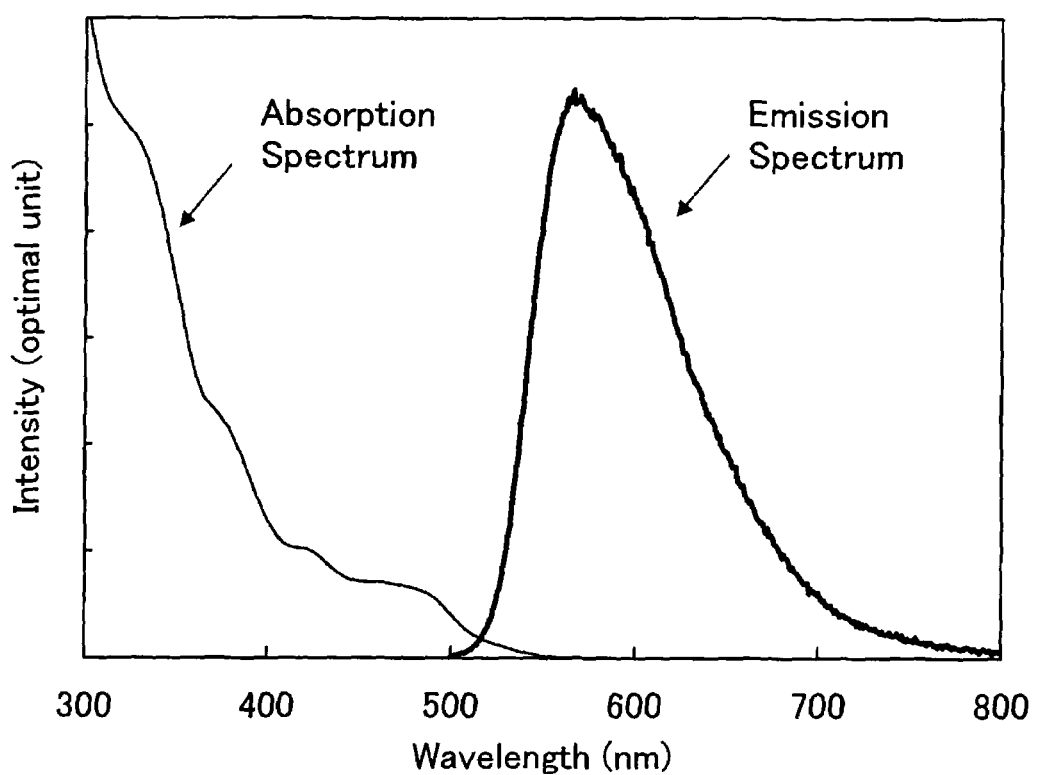
FIG. 44 is a graph showing an absorption spectrum and an emission spectrum of an organometallic complex synthesized in Synthesis Example 6.

Moreover, measurement of an absorption spectrum (using an ultraviolet-visible spectrophotometer by JASCO Corporation, V-550) and an emission spectrum (using a spectrofluorometer by Hamamatsu Photonics K.K., FS 920) of Ir(CF$_3$dppr-Me)$_2$(pic) at a room temperature was conducted by using deaerated dichloromethane solution. The results are shown in FIG. 44. In FIG. 44, a horizontal axis represents wavelength (nm), and a vertical axis represents intensity (an arbitrary unit). As can be seen from FIG. 44, the organometallic complex Ir(CF$_3$dppr-Me)$_2$(pic) according to the present invention has absorption peaks at 330 nm, 376 nm, 422 nm, 483 nm and 520 nm. In addition, the emission spectrum of Ir(CF$_3$dppr-Me)$_2$(pic) showed an emission peak at 566 nm, and emitted light was visible as yellow light.

[Embodiment 2]

In the present embodiment, a method for manufacturing a light-emitting element using Ir(Fdppr)$_2$(acac) synthesized by the method descried in Synthesis Example 1 as a luminescent substance and operating characteristics of the light-emitting element will be described.

Figure 13:
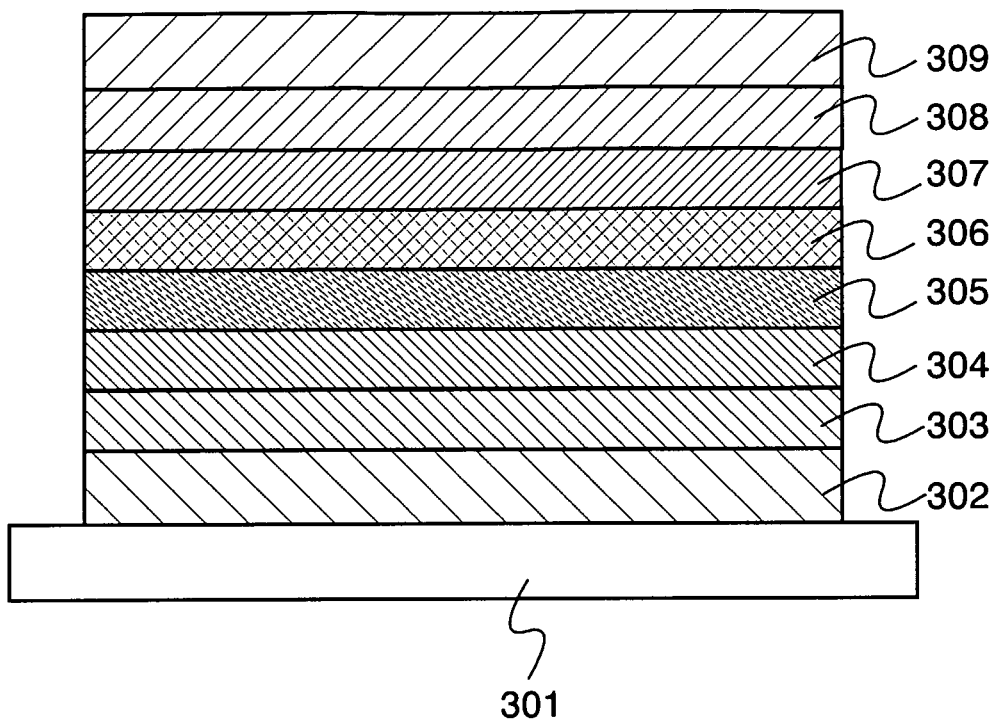
FIG. 13 is a view explaining a manufacturing method of a light-emitting element containing an organometallic complex synthesized in Synthesis Example 1.

As shown in FIG. 13, a first electrode 302 was formed by forming indium tin oxide containing silicon oxide over a glass substrate 301 by sputtering. The thickness of the first electrode 302 was made to be 110 nm. The first electrode 302 was made to have a square shape having a size of: 2 mm×2 mm.

Next, the glass substrate 301 where the first electrode 302 was formed was fixed to a holder provided in a vacuum evaporation system so that a surface where the first electrode was formed faced downward.

Thereafter, a first layer 303 was formed by using copper phthalocyanine over the first electrode 302 by evaporation after exhausting a gas from the vacuum evaporation system and reducing pressure to be 1×10$^{-4}$ Pa. The thickness of the first layer 303 was made to be 20 nm. This first layer 303 is a layer that functions as a hole-injecting layer when a light-emitting element is made to operate.

Then, a second layer 304 was formed by using NPB over the first layer 303 by evaporation. The thickness of the second layer 304 was made to be 40 nm. This second layer 304 is a layer that functions as a hole-transporting layer when a light-emitting element is made to operate.

Thereafter, a third layer 305 containing CBP and Ir(Fdppr)$_2$(acac) was formed over the second layer 304 by co-evaporation. The thickness of the third layer 305 was made to be 40 nm, and the mass ratio of CBP to Ir(Fdppr)$_2$(acac) was set to be 1:0.05. Accordingly, Ir(Fdppr)$_2$(acac) was in a state to be dispersed in a layer that was formed by using CBP. This third layer 305 is a layer that functions as a light-emitting layer when a light-emitting element is made to operate.

Subsequently, a fourth layer 306 was formed by using BCP over the third layer 305 by evaporation. The thickness of the fourth layer 306 was made to be 20 nm. This fourth layer 306 is a layer that transports electrons to the third layer 305 functioning as a light-emitting layer, prevent holes injected from the first electrode 302 side from passing through the third layer 305 to the other electrode side, and prevent excitation energy generated in the third layer 305 from transferring from the third layer 305 to the other layer, when a light-emitting element is made to operate. A layer having such a function is referred to as a hole-blocking layer, or simply, a blocking-layer.

Thereafter, a fifth layer 307 was formed by using Alq$_3$ over the fourth layer 306 by evaporation. The thickness of the fifth layer 307 was made to be 20 nm. This fifth layer 307 is a layer that functions as an electron-transporting layer when a light-emitting element is made to operate.

Next, a sixth layer 308 was formed by using calcium fluoride over the fifth layer 307 by evaporation. The thickness of the sixth layer 308 was made to be 1 nm. This sixth layer 308 is a layer that functions as an electron-injecting layer when a light-emitting element is made to operate.

Next, a second electrode 309 was formed by using aluminum over the sixth layer 308. The thickness of the second electrode 309 was made to be 200 nm.

In a light-emitting element manufactured as described above, a current flows when a voltage is applied so that the potential of the first electrode 302 gets higher than the potential of the second electrode 309, and light is emitted when excitation energy is generated after recombining electrons and holes in the third layer 305 that functions as a light-emitting layer and the excited Ir(Fdppr)$_2$(acac) returns to a ground state. It is to be noted that a layer functioning as a blocking-layer may also be provided as in the present embodiment. This can prevent excitation energy from transferring from a light-emitting layer to the other layer, and holes from passing through the light-emitting layer to the other layer, thereby obtaining a light-emitting element that can emit light efficiently.

In a glove box (a sealing device) under a nitrogen atmosphere, a sealing operation was performed so that this light-emitting element is not exposed to an atmosphere. Thereafter, operating characteristics of the light-emitting element were measured. The measurement was conducted at a room temperature (an atmosphere kept at 25° C.).

Figure 14:
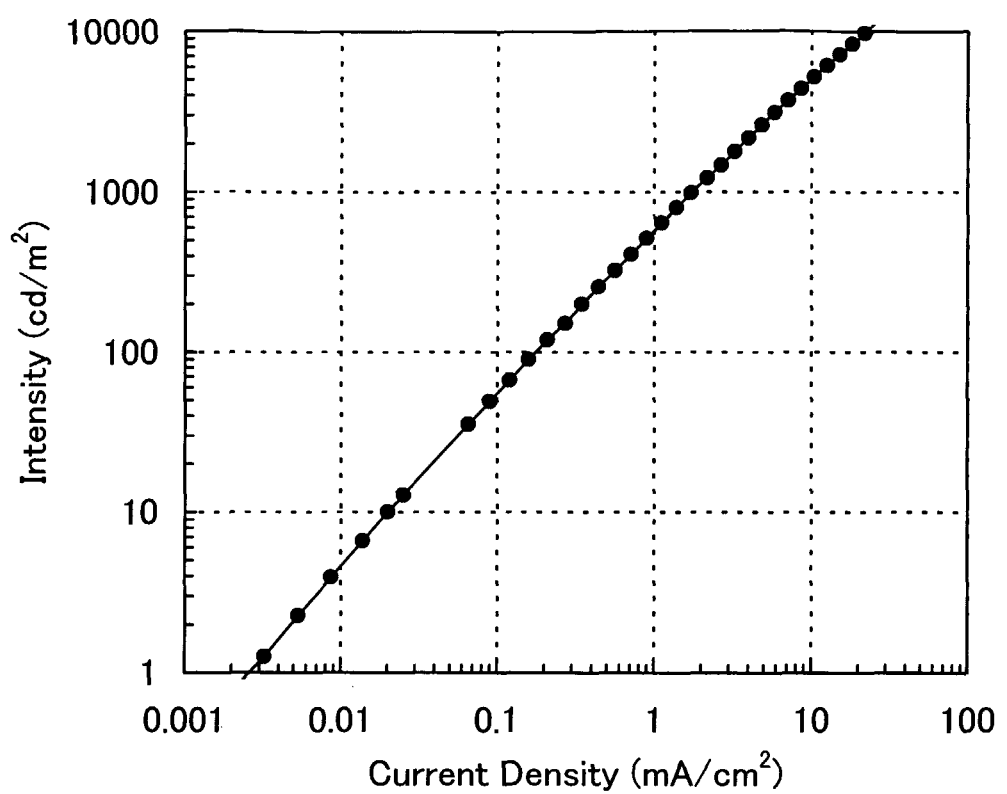
FIG. 14 is a graph showing current density-luminance characteristics of a light-emitting device of Embodiment 2.
Figure 15:
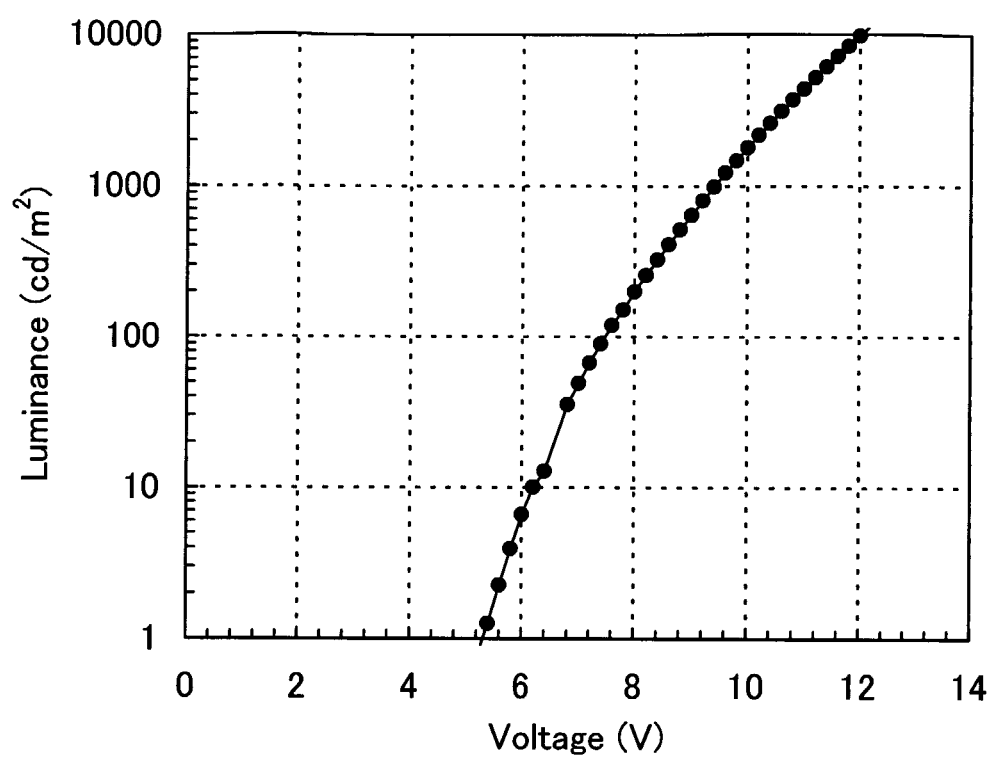
FIG. 15 is a graph showing voltage-luminance characteristics when a light-emitting device of Embodiment 2 is operated.
Figure 16:
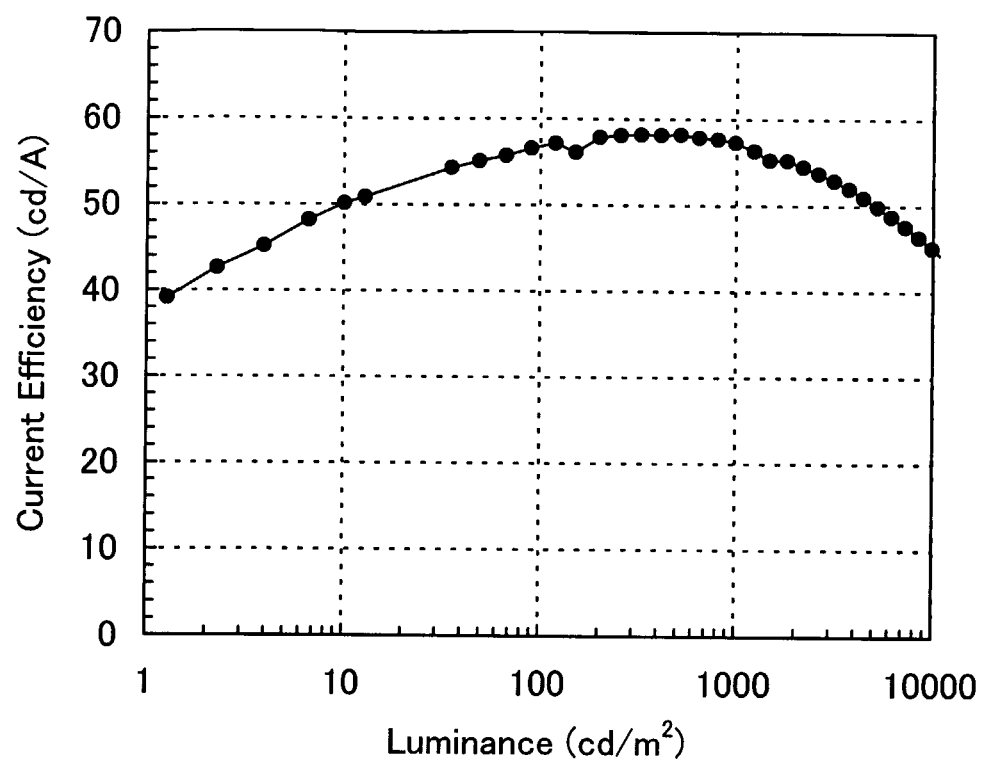
FIG. 16 is a graph showing luminance-current efficiency characteristics when a light-emitting device of Embodiment 2 is operated.

FIGS. 14 to 16 each show a measurement result. FIG. 14 shows a result regarding current density-luminance characteristics, FIG. 15 shows a result regarding voltage-luminance characteristics, and FIG. 16 shows a result regarding luminance-current efficiency characteristics. In FIG. 14, a horizontal axis represents current density (mA/cm$^2$), whereas a vertical axis represents luminance (cd/m$^2$). In addition, in FIG. 15, a horizontal axis represents voltage (V), whereas a vertical axis represents luminance (cd/m$^2$). Further, in FIG. 16, a horizontal axis represents luminance (cd/m$^2$), whereas a vertical axis represents current efficiency (cd/A). From these results, it was determined that, in the light-emitting element of the present embodiment, a current flowed at a current density of 0.887 mA/cm$^2$ when a voltage of 8.8 V was applied, and light emission was obtained at a luminance of 520 cd/m$^2$. The current efficiency was 58 cd/A in light emission at a luminance of 520 cd/m$^2$, which is 17% when it is converted into external quantum efficiency (photon number/electron number). It is said that a theoretical limitation of external quantum efficiency of a light-emitting element manufactured over a glass substrate is about 20%. Accordingly, it is understood that the light-emitting element according to the present embodiment emits light highly efficiently. By employing a stacked structure as in Embodiment 2, an organometallic complex according to the present invention can emit light efficiently with favorable color purity. As shown in FIG. 16, a light-emitting element according to the present embodiment is a light-emitting element in which change in current efficiency with respect to luminance is very small in a region of high-luminance (100 to 1000 cd/m$_2$) and the current efficiency is scarcely lowered in accordance with increase in luminance. This indicates that, in the light-emitting element according to the present embodiment, non-emitting transition due to an excitation lifetime of an excited triplet state or the like is not easily increased even in a high-luminance region, and excitation and luminescence can be repeated efficiently.

Figure 17:
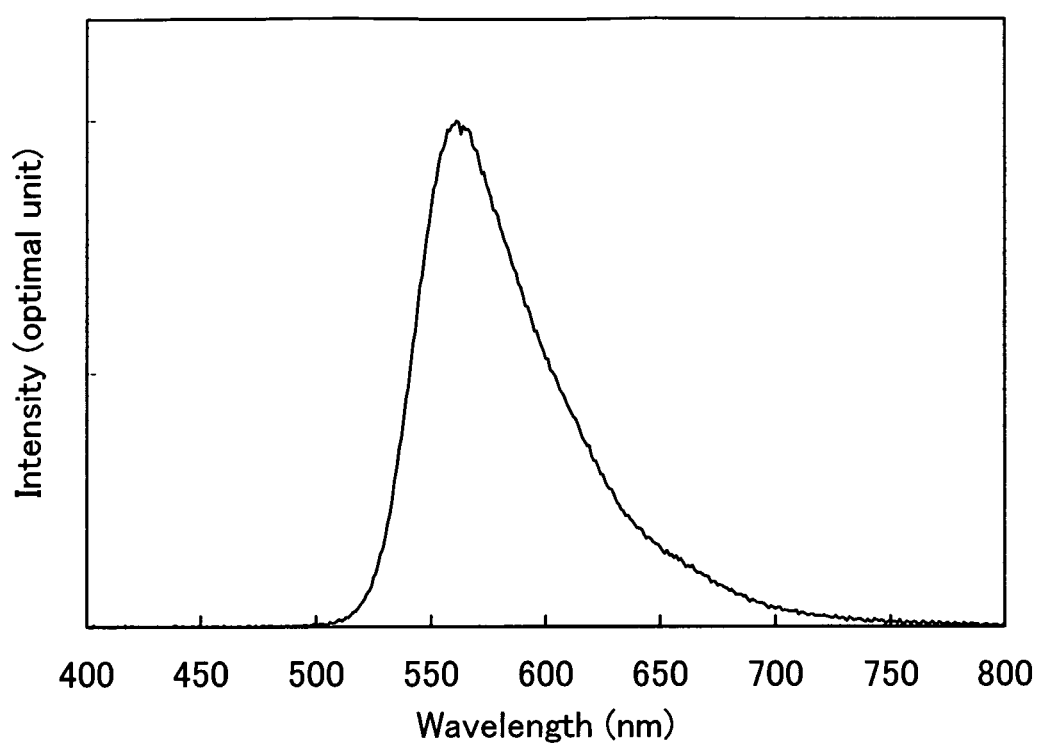
FIG. 17 is a graph showing an emission spectrum that is obtained when a light-emitting device of Embodiment 2 is operated.

FIG. 17 shows an emission spectrum of the light-emitting element manufactured in the present embodiment. In FIG. 17, a horizontal axis represents wavelength (nm), and a vertical axis represents intensity (an arbitrary unit). As can be seen from FIG. 17, the light-emitting element according to the present embodiment showed an emission peak at 561 nm, and emitted light was visible as yellow light. In addition, the emission spectrum has a very sharp spectrum shape in which the half-width is 60 nm. Further, it was found that chromaticity coordinate in CIE colorimetric system was (x, y)=(0.48, 0.52), and the light emitting element of the present embodiment can emit light that is yellow with excellent chromatic purity.

[Embodiment 3]

In the present embodiment, a method for manufacturing a light-emitting element using Ir(Fdppr-Me)$_2$(acac) that is synthesized by the method described in Synthesis Example 2 as a luminescent substance and operating characteristics of the light-emitting element will be described.

Figure 18:
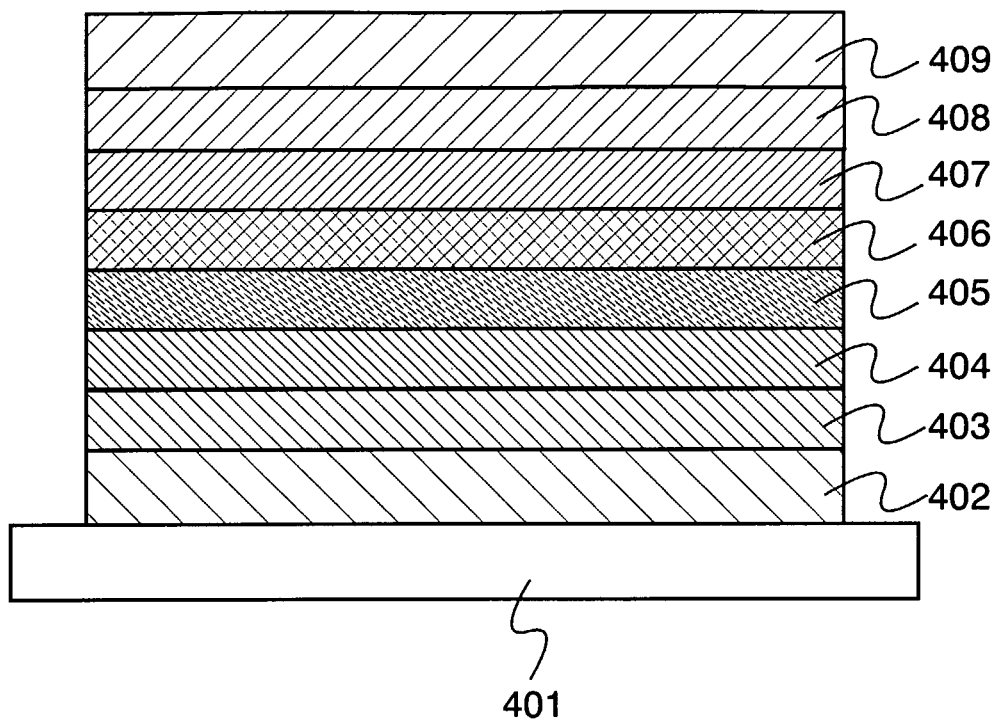
FIG. 18 is a view explaining a manufacturing method of a light-emitting element containing an organometallic complex synthesized in Synthesis Example 2.

As shown in FIG. 18, a first electrode 402 was formed by depositing indium tin oxide containing silicon oxide over a glass substrate 401 by sputtering. The thickness of the first electrode 402 was made to be 110 nm. The first electrode 402 was made to have a square shape having a size of: 2 mm×2 mm.

Subsequently, the glass substrate 401 where the first electrode 402 was formed was fixed to a holder provided in a vacuum evaporation system so that a surface where the first electrode was formed faced downward.

Thereafter, a first layer 403 was formed by using DNTPD over the first electrode 402 by evaporation after exhausting a gas from the vacuum evaporation system and reducing pressure to be 1×10$^{-4}$ Pa. The thickness of the first layer 403 was made to be 50 nm. This first layer 403 is a layer that functions as a hole-injecting layer when a light-emitting element is made to operate.

Then, a second layer 404 was formed by using NPB over the first layer 403. The thickness of the second layer 404 was made to be 10 nm. The second layer 404 is a layer that functions as a hole-transporting layer when a light-emitting element is made to operate.

Thereafter, a third layer 405 containing CBP and Ir(Fdppr-Me)$_2$(acac) was formed over the second layer 404 by co-evaporation. The thickness of the third layer 405 was made to be 30 nm, and the mass ratio of CBP to Ir(Fdppr-Me)$_2$(acac) was set to be 1:0.025. Accordingly, Ir(Fdppr-Me)$_2$(acac) was in a state to be dispersed in a layer that was formed by using CBP. This third layer 405 is a layer that functions as a light-emitting layer when a light-emitting element is made to operate.

Next, a forth layer 406 was formed by using BCP over the third layer 405 by evaporation. The thickness of the forth layer 406 was made to be 20 nm. The forth layer 406 functions as a blocking layer. The blocking layer was as described in Embodiment 2.

Subsequently, a fifth layer 407 was formed by using Alq$_3$ over the forth layer 406 by evaporation. The thickness of the fifth layer 407 was made to be 30 nm. The fifth layer 407 is a layer that functions as an electron-transporting layer when a light-emitting element is made to operate.

Then, a sixth layer 408 was formed by using calcium fluoride over the fifth layer 407 by evaporation. The thickness of the sixth layer 408 was made to be 1 nm. The sixth layer 408 is a layer that functions as an electron-injecting layer when a light-emitting element is made to operate.

Next, a second electrode 409 was formed by using aluminum over the sixth layer 408. The thickness of the second electrode 409 was made to be 200 nm.

In a light-emitting element manufactured as described above, a current flows when a voltage is applied so that the potential of the first electrode 402 gets higher than the potential of the second electrode 409, and light is emitted when excitation energy is generated after recombining electrons and holes in the third layer 405 that functions as a light-emitting layer and the excited Ir(Fdppr-Me)$_2$(acac) returns to a ground state.

In a glove box (a sealing device) under a nitrogen atmosphere, a sealing operation was performed so that this light-emitting element is not exposed to an atmosphere. Thereafter, operating characteristics of the light-emitting element were measured. The measurement was conducted at a room temperature (an atmosphere kept at 25° C.).

Figure 19:
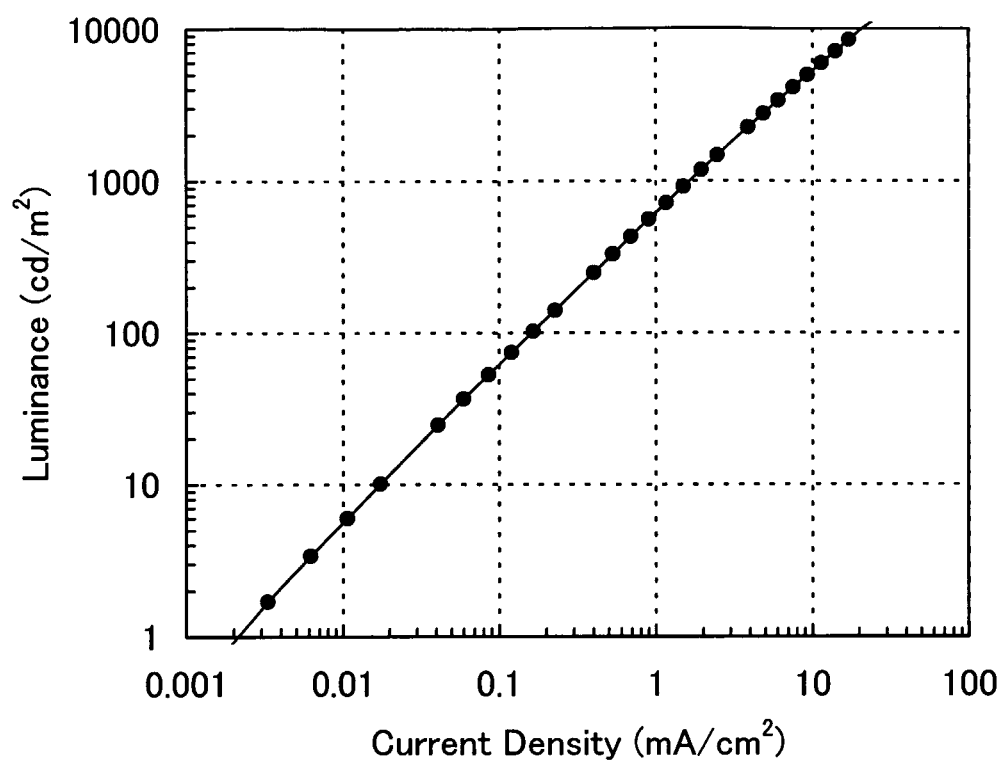
FIG. 19 is a graph showing current density-luminance characteristics of a light-emitting device of Embodiment 3.
Figure 20:
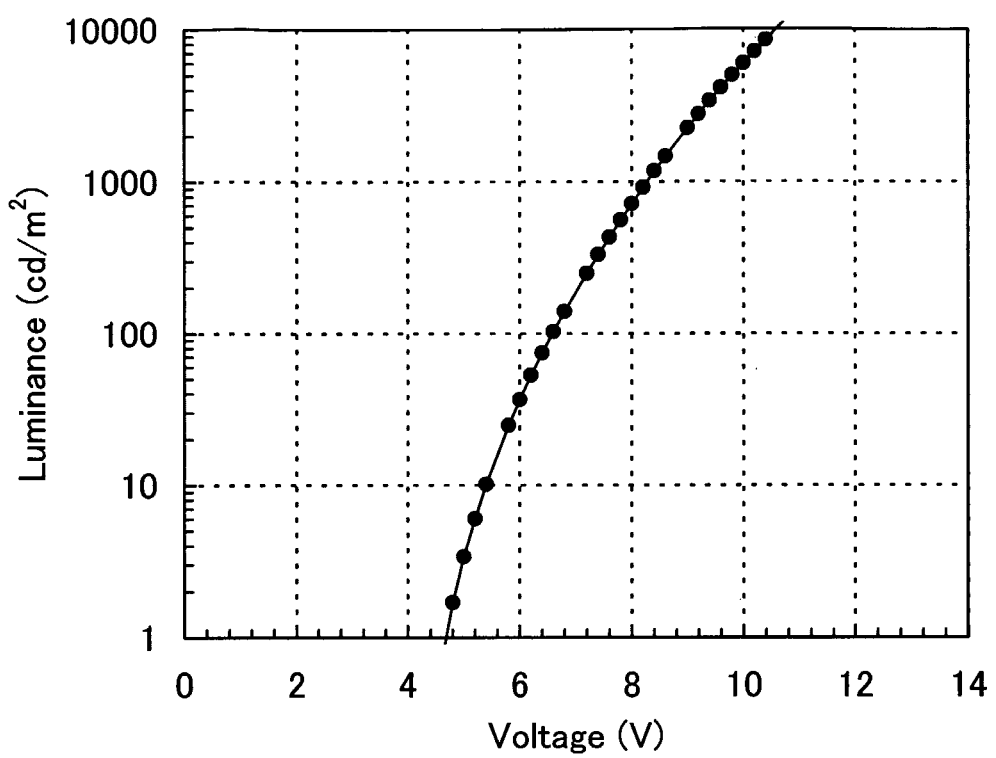
FIG. 20 is a graph showing voltage-luminance characteristics when a light-emitting device of Embodiment 3 is operated.
Figure 21:
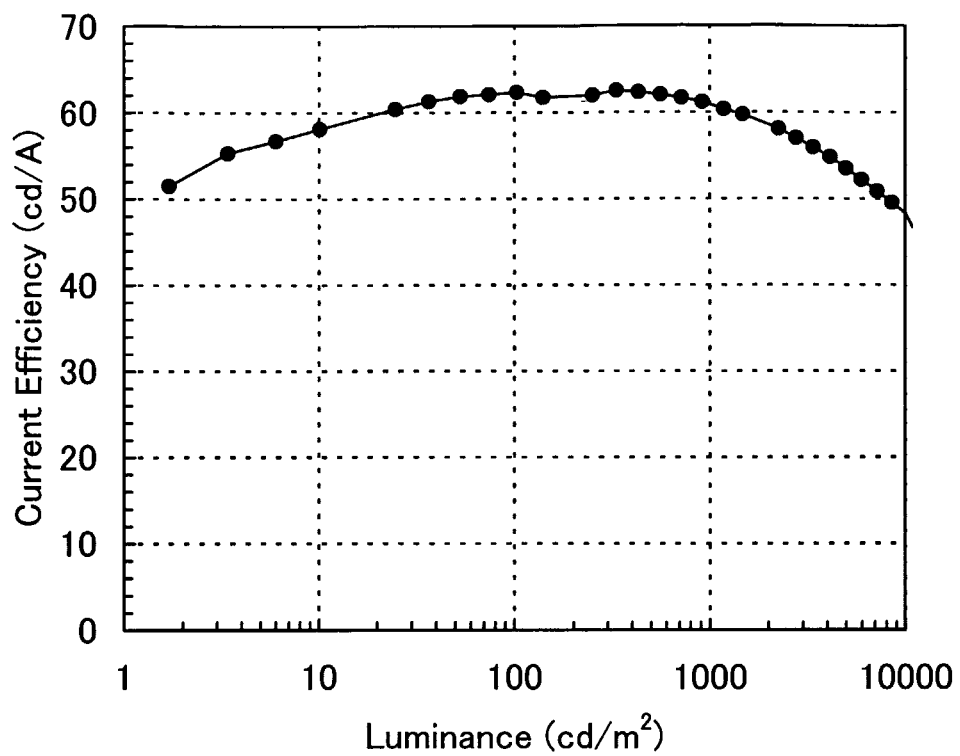
FIG. 21 is a graph showing luminance-current efficiency characteristics when a light-emitting device of Embodiment 3 is operated.

FIGS. 19 to 21 each show a measurement result. FIG. 19 shows a result regarding current density-luminance characteristics, FIG. 20 shows a result regarding voltage-luminance characteristics, and FIG. 21 shows a result regarding luminance-current efficiency characteristics. In FIG. 19, a horizontal axis represents current density (mA/cm$^2$), whereas a vertical axis represents luminance (cd/m$^2$). In addition, in FIG. 20, a horizontal axis represents voltage (V), whereas a vertical axis represents luminance (cd/m$^2$). Further, in FIG. 21, a horizontal axis represents luminance (cd/m$^2$), whereas a vertical axis represents current efficiency (cd/A). From these results, it was determined that, in a light-emitting element of the present embodiment, a current flowed at a current density of 1.5 mA/cm$^2$ when a voltage of 8.2 V was applied, and light emission was obtained at a luminance of 920 cd/m$^2$. The current efficiency was 61 cd/A in light emission at a luminance of 920 cd/m$^2$, which is 18% when it is converted into external quantum efficiency (photon number/electron number). Accordingly, it is understood that the light-emitting element according to the present embodiment emits light highly efficiently. By employing a stacked structure as in Embodiment 3, an organometallic complex according to the present invention can emit light efficiently with favorable color purity. As shown in FIG. 21, the light-emitting element according to the present embodiment is a light-emitting element in which change in current efficiency with respect to luminance is very small in a region of high-luminance (100 to 1000 cd/m$_2$) and the current efficiency is scarcely lowered in accordance with increase in luminance. This indicates that, in the light-emitting element according to the present embodiment, non-emitting transition due to an excitation lifetime of an excited triplet state or the like is not easily increased even in a high-luminance region, and excitation and luminescence can be repeated efficiently.

Figure 22:
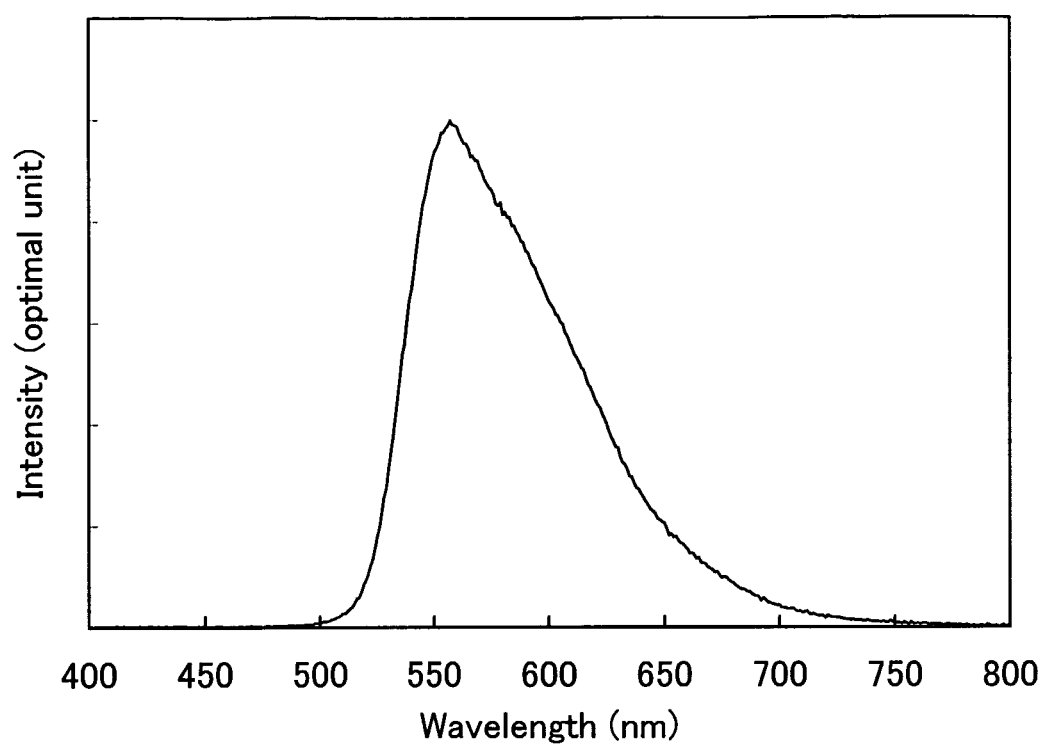
FIG. 22 is a graph showing an emission spectrum that is obtained when a light-emitting device of Embodiment 3 is operated.

FIG. 22 shows an emission spectrum of the light-emitting element manufactured in the present embodiment. In FIG. 22, a horizontal axis represents wavelength (nm), and a vertical axis represents intensity (an arbitrary unit). As can be seen from FIG. 22, the light-emitting element according to the present embodiment showed an emission peak at 557 nm, and emitted light was visible as yellow light. In addition, the emission spectrum has a very sharp spectrum shape in which the half-width is 80 nm. Further, it was found that chromaticity coordinate in CIE colorimetric system was (x, y)=(0.47, 0.52), and the light emitting element of the present embodiment can emit light that is yellow with excellent color purity.

[Embodiment 4]

In the present embodiment, a method for manufacturing a light-emitting element using Ir(Fdppr-Me)$_2$(bpz$_4$) that is synthesized by the method described in Synthesis Example 3 as a luminescent substance and operating characteristics of the light-emitting element will be described.

Figure 27:
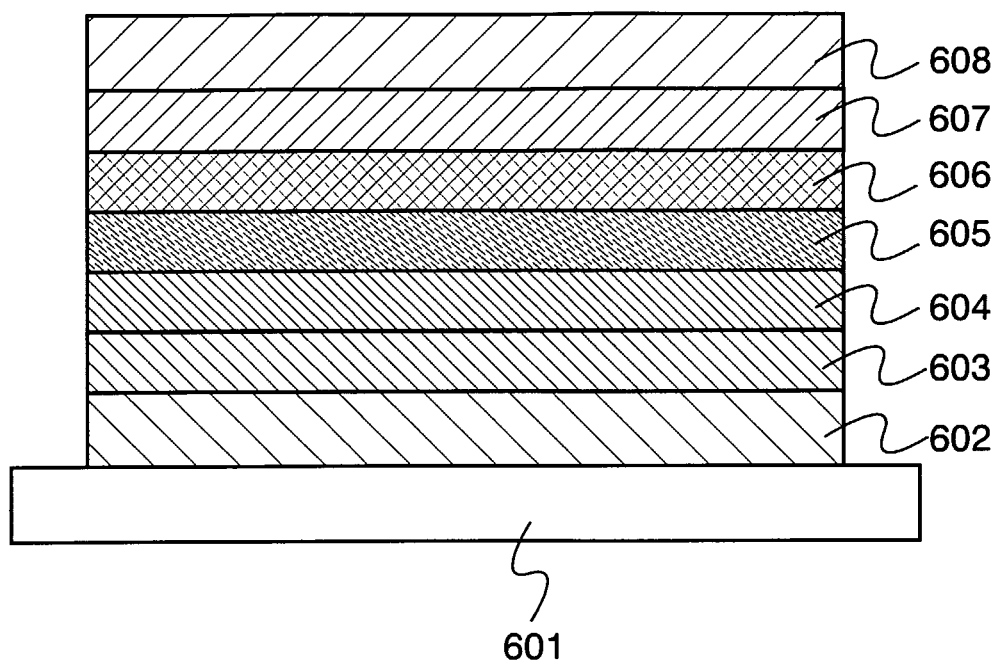
FIG. 27 is a view explaining a manufacturing method of a light-emitting element of Embodiments 4 to 7.

As shown in FIG. 27, a first electrode 602 was formed by forming indium tin oxide containing silicon oxide by sputtering over a glass substrate 601. The thickness of the first electrode 602 was made to be 110 nm. The first electrode 602 was made to have a square shape having a size of: 2 mm×2 mm.

Subsequently, the glass substrate 601 where the first electrode 602 was formed was fixed to a holder provided in a vacuum evaporation system so that a surface where the first electrode was formed faced downward.

Thereafter, a first layer 603 containing NPB and molybdenum oxide was formed over the first electrode 602 by evaporation after exhausting a gas from the vacuum evaporation system and reducing pressure to be 1×10$^{-4}$ Pa. The thickness of the first layer 603 was made to be 50 nm, and the mass ratio of NPB to molybdenum oxide was set to be 4:1. This first layer 603 is a layer that functions as a hole-injecting layer when a light-emitting element is made to operate.

Then, a second layer 604 was formed by using NPB over the first layer 603 by evaporation. The thickness of the second layer 604 was made to be 10 nm. The second layer 604 is a layer that functions as a hole-transporting layer when a light-emitting element is made to operate.

Thereafter, a third layer 605 containing CBP and Ir(Fdppr-Me)$_2$(bpz$_4$) was formed over the second layer 604 by co-evaporation. The thickness of the third layer 605 was made to be 30 nm, and the mass ratio of CBP to Ir(Fdppr-Me)$_2$(bpz$_4$) was set to be 1:0.05. Accordingly, Ir(Fdppr-Me)$_2$(bpz$_4$) was in a state to be dispersed in a layer that was formed by using CBP. This third layer 605 is a layer that functions as a light-emitting layer when a light-emitting element is made to operate.

Subsequently, a fourth layer 606 was formed by using BCP over the third layer 605 by evaporation. The thickness of the fourth layer 606 was made to be 20 nm. This fourth layer 606 is a layer that transports electrons to the third layer 605 functioning as a light-emitting layer, prevent holes injected from the first electrode 602 side from passing through the third layer 605 to the other electrode side, and prevent excitation energy generated in the third layer 605 from transferring from the third layer 605 to the other layer, when a light-emitting element is made to operate. A layer having such a function is referred to as a hole-blocking layer, or simply, a blocking-layer.

Then, a fifth layer 607 containing Alq and lithium (Li) was formed over the forth layer 606 by evaporation. The thickness of the fifth layer 607 was made to be 20 nm, and the mass ratio of Alq to lithium (Li) was set to be 1:0.01. This fifth layer 607 is a layer that functions as an electron-injecting layer when a light-emitting element is made to operate.

A second electrode 608 was formed by using aluminum over the fifth layer 607. The thickness of the second electrode 608 was made to be 200 nm.

In a light-emitting element manufactured as described above, a current flows when a voltage is applied so that the potential of the first electrode 602 gets higher than the potential of the second electrode 608, and light is emitted when excitation energy is generated after recombining electrons and holes in the third layer 605 that functions as a light-emitting layer and the excited Ir(Fdppr-Me)$_2$(bpz$_4$) returns to a ground state. It is to be noted that a layer functioning as a blocking-layer may also be provided as in the present embodiment. This can prevent excitation energy from transferring from a light-emitting layer to the other layer, and holes from passing through the light-emitting layer to the other layer, thereby obtaining a light-emitting element that can emit light efficiently.

In a glove box (a sealing device) under a nitrogen atmosphere, a sealing operation was performed so that this light-emitting element is not exposed to an atmosphere. Thereafter, operating characteristics of the light-emitting element were measured. The measurement was conducted at a room temperature (an atmosphere kept at 25° C.).

Figure 28:
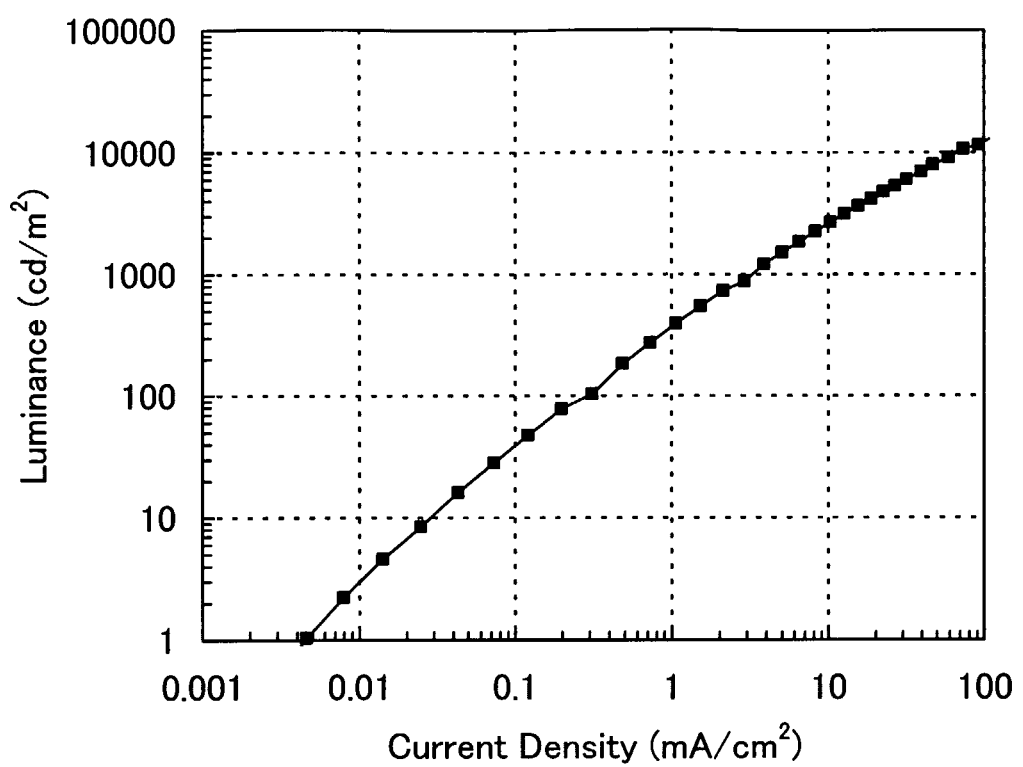
FIG. 28 is a graph showing current density-luminance characteristics of a light-emitting device of Embodiment 4.
Figure 29:
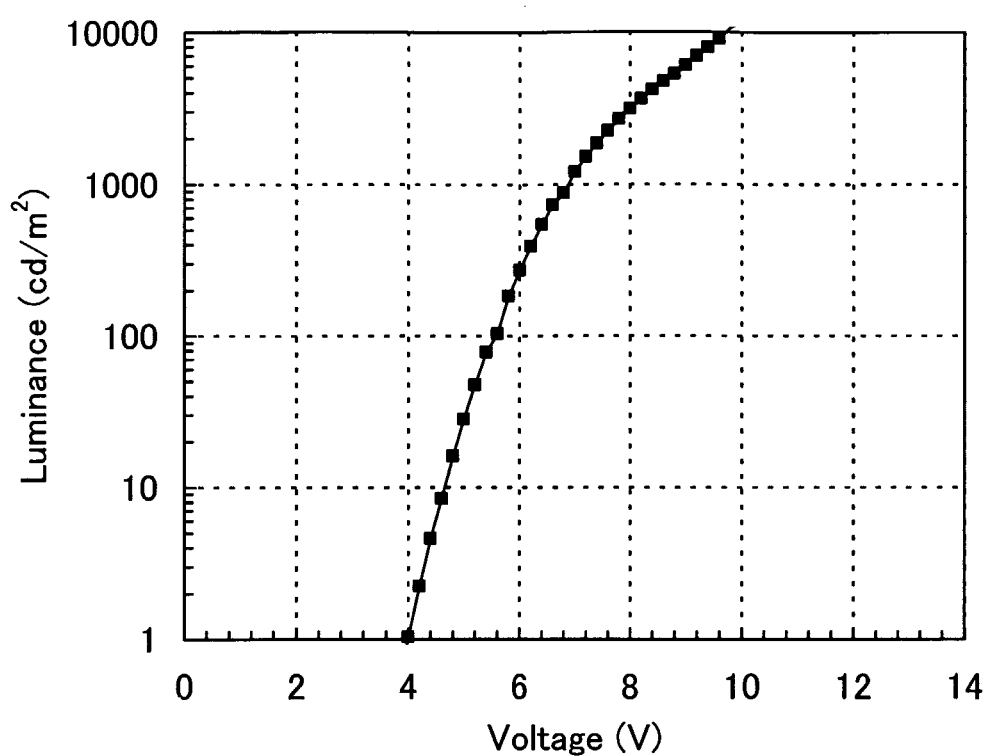
FIG. 29 is a graph showing voltage-luminance characteristics when a light-emitting device of Embodiment 4 is operated.
Figure 30:
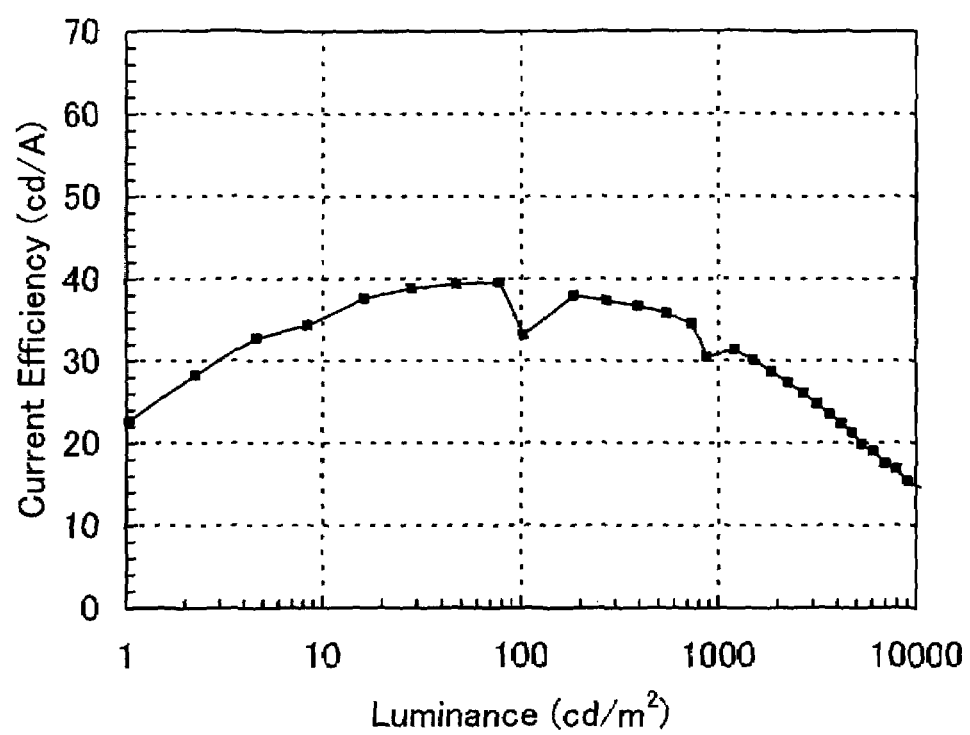
FIG. 30 is a graph showing luminance-current efficiency characteristics when a light-emitting device of Embodiment 4 is operated.

FIGS. 28 to 31 each show a measurement result. FIG. 28 shows a result regarding current density-luminance characteristics, FIG. 29 shows a result regarding voltage-luminance characteristics, and FIG. 30 shows a result regarding luminance-current efficiency characteristics. In FIG. 28, a horizontal axis represents current density (mA/cm$^2$), whereas a vertical axis represents luminance (cd/m$^2$). In addition, in FIG. 29, a horizontal axis represents voltage (V), whereas a vertical axis represents luminance (cd/m$^2$). Further, in FIG. 30, a horizontal axis represents luminance (cd/m$^2$), whereas a vertical axis represents current efficiency (cd/A). From these results, it was determined that, in the light-emitting element according to the present embodiment, a current flowed at a current density of 3.86 mA/cm$^2$ when a voltage of 7.0 V was applied, and light emission was obtained at a luminance of 1210 cd/m². The current efficiency was 31.4 cd/A in light emission at a luminance of 1210 cd/m², which is 9.34% when it is converted into external quantum efficiency (photon number/electron number). In addition, the maximum value of the external quantum efficiency was 11.8% in light emission at a luminance of 7.78 cd/m².

Figure 31:
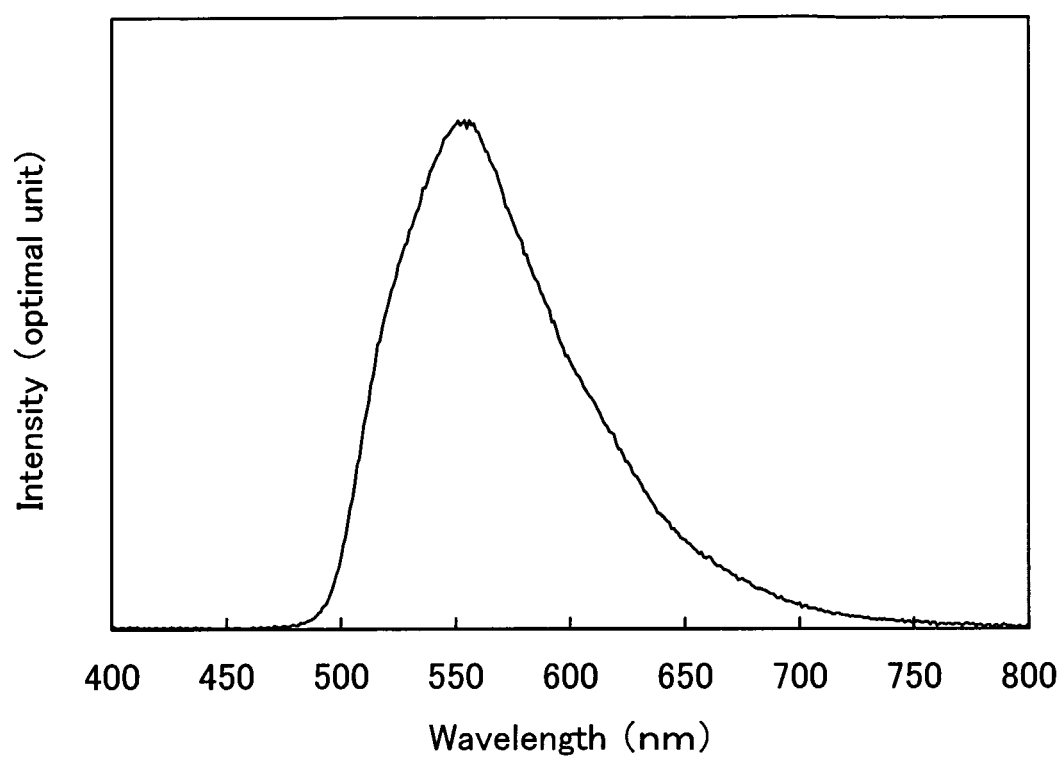
FIG. 31 is a graph showing an emission spectrum that is obtained when a light-emitting device of Embodiment 4 is operated.

FIG. 31 shows an emission spectrum of the light-emitting element manufactured in the present embodiment. In FIG. 31, a horizontal axis represents wavelength (nm), and a vertical axis represents intensity (an arbitrary unit). As can be seen from FIG. 31, the light-emitting element according to the present embodiment showed an emission peak at 556 nm, and emitted light was visible as green yellow light. Further, it was found that chromaticity coordinate in CIE colorimetric system was (x, y)=(0.42, 0.52), and the light emitting element of the present embodiment can emit light that is green yellow.

[Embodiment 5]

In the present embodiment, a method for manufacturing a light-emitting element using Ir(Fdppr-Me)$_2$(pic) that is synthesized by the method described in Synthesis Example 4 as a luminescent substance and operating characteristics of the light-emitting element will be described. Since a light-emitting element manufactured in the present embodiment has a structure in which five layers are stacked between electrodes similarly to the light-emitting element manufactured in Embodiment 4, FIG. 27 that is used in the explanation of Embodiment 4 will also be used here.

As shown in FIG. 27, a first electrode 602 was formed by depositing indium tin oxide containing silicon oxide over a glass substrate 601 by sputtering. The thickness of the first electrode 602 was made to be 110 nm. The first electrode 602 was made to have a square shape having a size of: 2 mm×2 mm.

Subsequently, the glass substrate 601 where the first electrode 602 was formed was fixed to a holder provided in a vacuum evaporation system.

Thereafter, a first layer 603 containing NPB and molybdenum oxide (VI) was formed over the first electrode 602 by co-evaporation of NPB and molybdenum oxide (VI) after exhausting a gas from the vacuum evaporation system and reducing pressure to be 1×10$^{-4}$ Pa. The thickness of the first layer 603 was made to be 40 nm. The mass ratio of NPB to molybdenum oxide (VI) in co-evaporation was set to be 4:1. This first layer 603 is a layer that functions as a hole-generating layer when a light-emitting element is made to operate.

Then, a second layer 604 was formed by using NPB over the first layer 603 by evaporation. The thickness of the second layer 604 was made to be 20 nm. The second layer 604 is a layer that functions as a hole-transporting layer when a light-emitting element is made to operate.

Thereafter, a third layer 605 containing CBP and Ir(Fdppr-Me)$_2$(pic) was formed over the second layer 604 by co-evaporation. The thickness of the third layer 605 was made to be 30 nm, and the mass ratio of CBP to Ir(Fdppr-Me)$_2$(pic) was set to be 1:0.05. Accordingly, Ir(Fdppr-Me)$_2$(pic) was in a state to be dispersed in a layer containing CBP as a matrix. This third layer 605 is a layer that functions as a light-emitting layer when a light-emitting element is made to operate.

Subsequently, a fourth layer 606 was formed by using BCP over the third layer 605 by evaporation. The thickness of the fourth layer 606 was made to be 20 nm. This fourth layer 606 is a layer that transports electrons to the third layer 605 functioning as a light-emitting layer, prevent holes injected from the first electrode 602 side from passing through the third layer 605 to the other electrode side, and prevent excitation energy generated in the third layer 605 from transferring from the third layer 605 to the other layer, when a light-emitting element is made to operate. A layer having such a function is referred to as a hole-blocking layer, or simply, a blocking-layer.

Then, a fifth layer 607 containing Alq and lithium (Li) was formed over the forth layer 606 by co-evaporation. The thickness of the fifth layer 607 was made to be 20 nm, and the mass ratio of Alq to lithium (Li) was set to be 1:0.01. This fifth layer 607 is a layer that functions as an electron-injecting layer when a light-emitting element is made to operate.

A second electrode 608 was formed by using aluminum over the fifth layer 607. The thickness of the second electrode 608 was made to be 200 nm.

In a light-emitting element manufactured as described above, a current flows when a voltage is applied so that the potential of the first electrode 602 gets higher than the potential of the second electrode 608 and light is emitted when excitation energy is generated after recombining electrons and holes in the third layer 605 that functions as a light-emitting layer and the excited Ir(Fdppr-Me)$_2$(pic) returns to a ground state. It is to be noted that a layer functioning as a blocking-layer may also be provided as in the present embodiment. This can prevent excitation energy from transferring from a light-emitting layer to the other layer, and holes from passing through the light-emitting layer to the other layer, thereby obtaining a light-emitting element that can emit light efficiently.

In a glove box (a sealing device) under a nitrogen atmosphere, a sealing operation was performed so that this light-emitting element is not exposed to an atmosphere. Thereafter, operating characteristics of the light-emitting element were measured. The measurement was conducted at a room temperature (an atmosphere kept at 25° C.).

Figure 34:
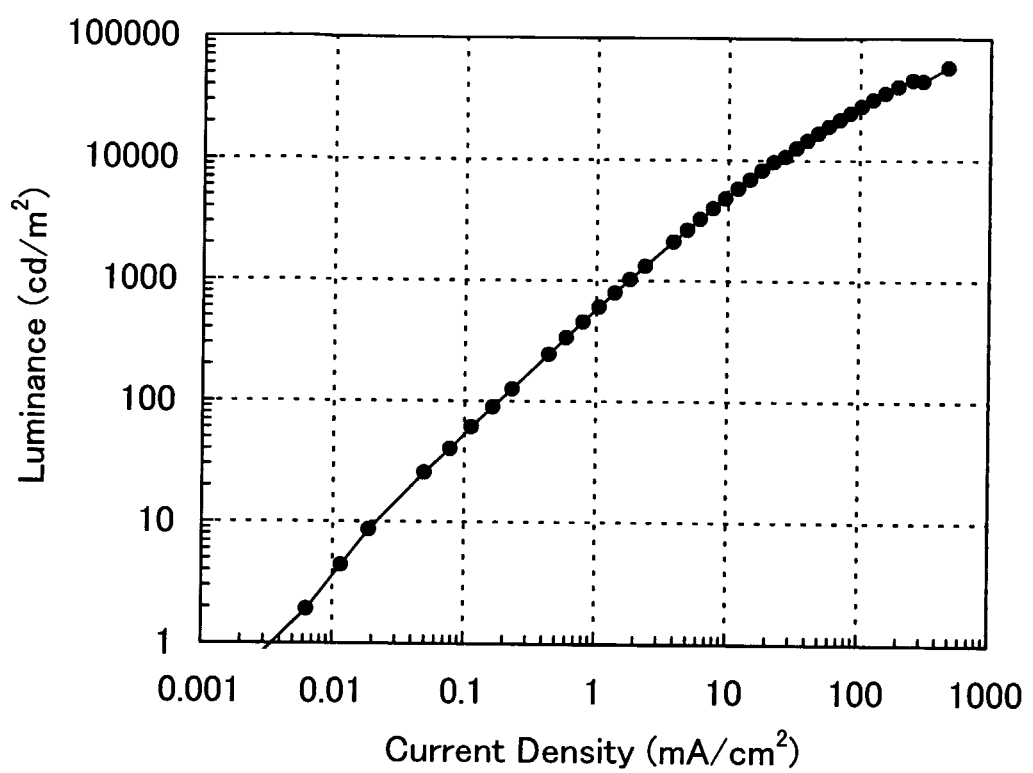
FIG. 34 is a graph showing current density-luminance characteristics of a light-emitting device of Embodiment 5.
Figure 35:
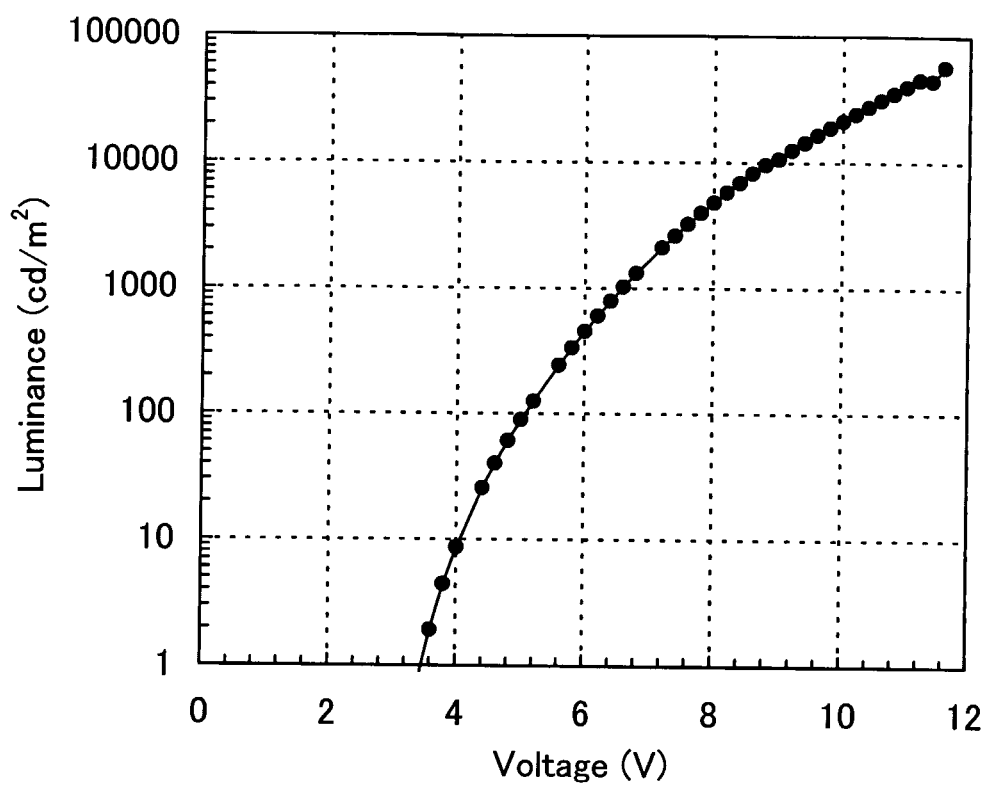
FIG. 35 is a graph showing voltage-luminance characteristics when a light-emitting device of Embodiment 5 is operated.
Figure 36:
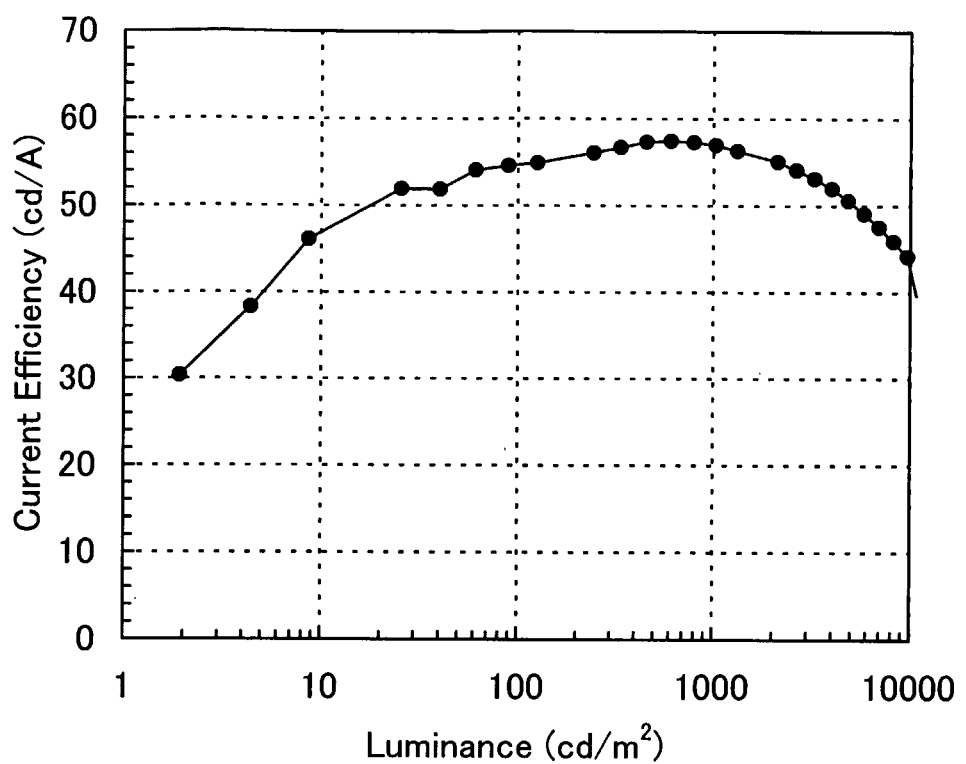
FIG. 36 is a graph showing luminance-current efficiency characteristics when a light-emitting device of Embodiment 5 is operated.

FIGS. 34 to 36 each show a measurement result. FIG. 34 shows a result regarding current density-luminance characteristics, FIG. 35 shows a result regarding voltage-luminance characteristics, and FIG. 36 shows a result regarding luminance-current efficiency characteristics. In FIG. 34, a horizontal axis represents current density (mA/cm²), whereas a vertical axis represents luminance (cd/m²). In addition, in FIG. 35, a horizontal axis represents voltage (V), whereas a vertical axis represents luminance (cd/m²). Further, in FIG. 36, a horizontal axis represents luminance (cd/m²), whereas a vertical axis represents current efficiency (cd/A). From these results, it was determined that, in the light-emitting element manufactured in the present embodiment, a current flowed at a current density of 1.80 mA/cm² when a voltage of 6.6 V was applied, and light emission was obtained at a luminance of 1030 cd/m². The current efficiency was 57.0 cd/A in light emission at a luminance of 1030 cd/m², which is 16.8% when it is converted into external quantum efficiency (photon number/electron number). In addition, the maximum value of the external quantum efficiency was 16.9% in light emission at a luminance of 604 cd/m². As shown in FIG. 36, it was found that a light-emitting element according to the present embodiment is a light-emitting element in which change in current efficiency with respect to luminance is very small in a region of high-luminance (100 to 1000 cd/m²) and the current efficiency is scarcely lowered in accordance with increase in luminance. This indicates that, in the light-emitting element according to the present embodiment, non-emitting transition due to an excitation lifetime of an excited triplet state or the like is not easily increased even in a high-luminance region, and excitation and luminescence can be repeated efficiently.

Figure 37:
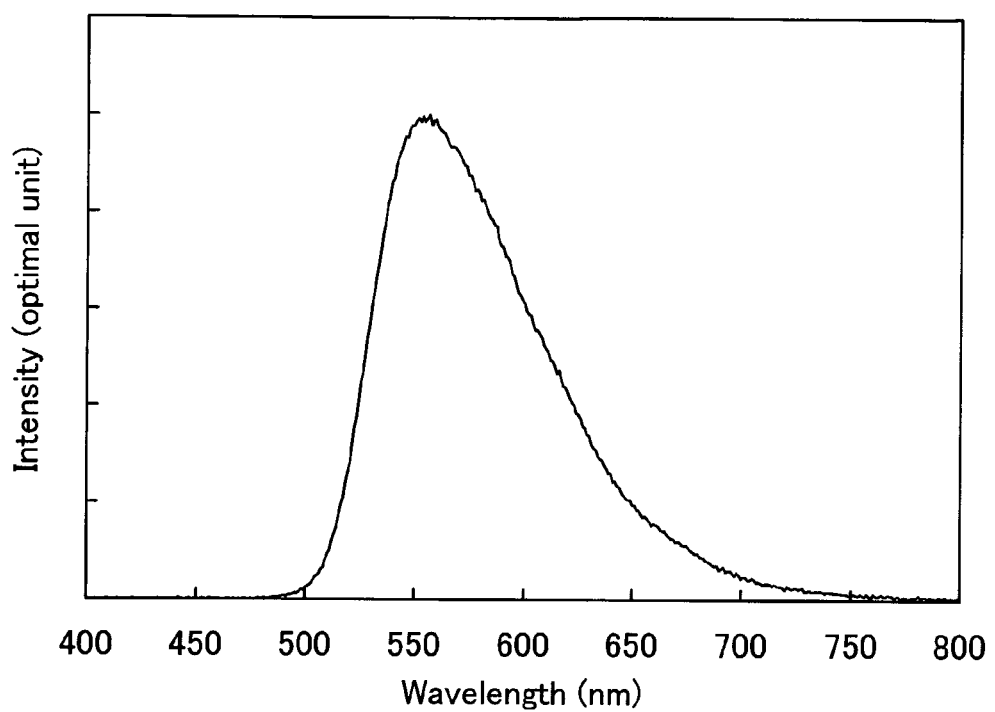
FIG. 37 is a graph showing an emission spectrum that is obtained when a light-emitting device of Embodiment 5 is operated.

FIG. 37 shows an emission spectrum of the light-emitting element manufactured in the present embodiment. In FIG. 37, a horizontal axis represents wavelength (nm), and a vertical axis represents intensity (an arbitrary unit). As can be seen from FIG. 37, the light-emitting element according to the present embodiment showed an emission peak at 556 nm, and emitted light was visible as green yellow light. Further, it was found that chromaticity coordinate in CIE colorimetric system was (x, y)=(0.42, 0.55).

[Embodiment 6]

In the present embodiment, a method for manufacturing a light-emitting element using Ir(Fdppr-iPr)$_2$(pic) that is synthesized in Synthesis Example 5 as a luminescent substance and operating characteristics of the light-emitting element will be described. Since a light-emitting element manufactured in the present embodiment has a structure in which five layers are stacked between electrodes similarly to the light-emitting element manufactured in Embodiment 4, FIG. 27 that is used in the explanation of Embodiment 4 will also be used here.

As shown in FIG. 27, a first electrode 602 was formed by depositing indium tin oxide containing silicon oxide by sputtering over a glass substrate 601. The thickness of the first electrode 602 was made to be 110 nm. The first electrode 602 was made to have a square shape having a size of: 2 mm×2 mm.

Subsequently, the glass substrate 601 where the first electrode 602 was formed was fixed to a holder provided in a vacuum evaporation system.

Thereafter, a first layer 603 containing NPB and molybdenum oxide (VI) was formed by using NPB and molybdenum oxide (VI) over the first electrode 602 by co-evaporation after exhausting a gas from the vacuum evaporation system and reducing pressure to be 1×10$^{-4}$ Pa. The thickness of the first layer 603 was made to be 40 nm. The mass ratio of NPB to molybdenum oxide (VI) in co-evaporation was set to be 4:1. This first layer 603 is a layer that functions as a hole-generating layer when a light-emitting element is made to operate.

Then, a second layer 604 was formed by using NPB over the first layer 603 by evaporation. The thickness of the second layer 604 was made to be 20 nm. This second layer 604 is a layer that functions as a hole-transporting layer when a light-emitting element is made to operate.

Thereafter, a third layer 605 containing CBP and Ir(Fdppr-iPr)$_2$(pic) was formed over the second layer 604 by co-evaporation. The thickness of the third layer 605 was made to be 30 nm, and the mass ratio of CBP to Ir(Fdppr-iPr)$_2$(pic) was set to be 1:0.01. Accordingly, Ir(Fdppr-iPr)$_2$(pic) was in a state to be dispersed in a layer that is formed by using CBP. This third layer 605 is a layer that functions as a light-emitting layer when a light-emitting element is made to operate.

Subsequently, a fourth layer 606 was formed by using TAZ over the third layer 605 by evaporation. The thickness of the fourth layer 606 was made to be 20 nm. This fourth layer 606 is a layer that transports electrons to the third layer 605 functioning as a light-emitting layer, prevent holes injected from the first electrode 602 side from passing through the third layer 605 to the other electrode side, and prevent excitation energy generated in the third layer 605 from transferring from the third layer 605 to the other layer, when a light-emitting element is made to operate. A layer having such a function is referred to as a hole-blocking layer, or simply, a blocking-layer.

Then, a fifth layer 607 containing TAZ and lithium (Li) was formed over the forth layer 606 by co-evaporation. The thickness of the fifth layer 607 was made to be 30 nm, and the mass ratio of TAZ to lithium (Li) was set to be 1:0.01. The fifth layer 607 is a layer that functions as an electron-injecting layer when a light-emitting element is made to operate.

Next, a second electrode 608 was formed by using aluminum over the fifth layer 607. The thickness of the second electrode 608 was made to be 200 nm.

In a light-emitting element manufactured as described above, a current flows when a voltage is applied so that the potential of the first electrode 602 gets higher than the potential of the second electrode 608 and light is emitted when excitation energy is generated after recombining electrons and holes in the third layer 605 that functions as a light-emitting layer and the excited Ir(Fdppr-iPr)$_2$(pic) returns to a ground state. It is to be noted that a layer functioning as a blocking-layer may also be provided as in the present embodiment. This can prevent excitation energy from transferring from a light-emitting layer to the other layer, and holes from passing through the light-emitting layer to the other layer, thereby obtaining a light-emitting element that can emit light efficiently.

In a glove box (a sealing device) under a nitrogen atmosphere, a sealing operation was performed so that this light-emitting element is not exposed to an atmosphere. Thereafter, operating characteristics of the light-emitting element were measured. The measurement was conducted at a room temperature (an atmosphere kept at 25° C.).

Figure 38:
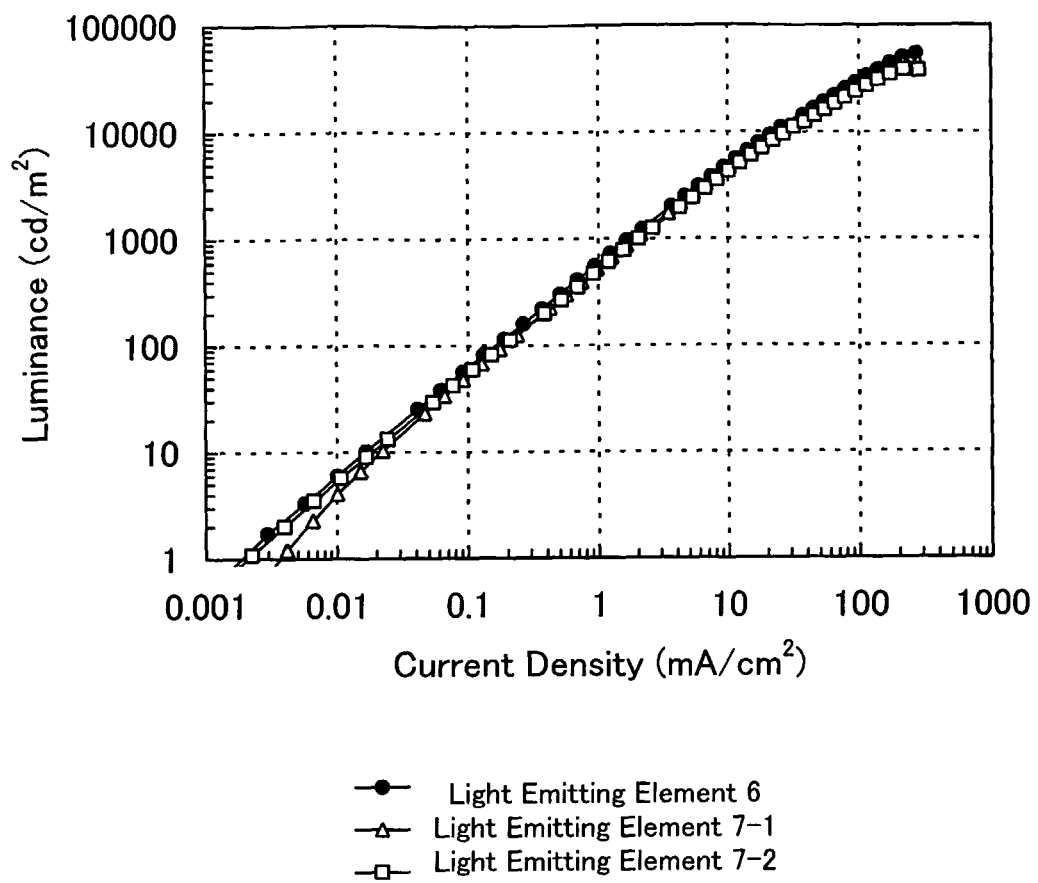
FIG. 38 is a graph showing current density-luminance characteristics of light-emitting devices of Embodiments 6 and 7.
Figure 39:
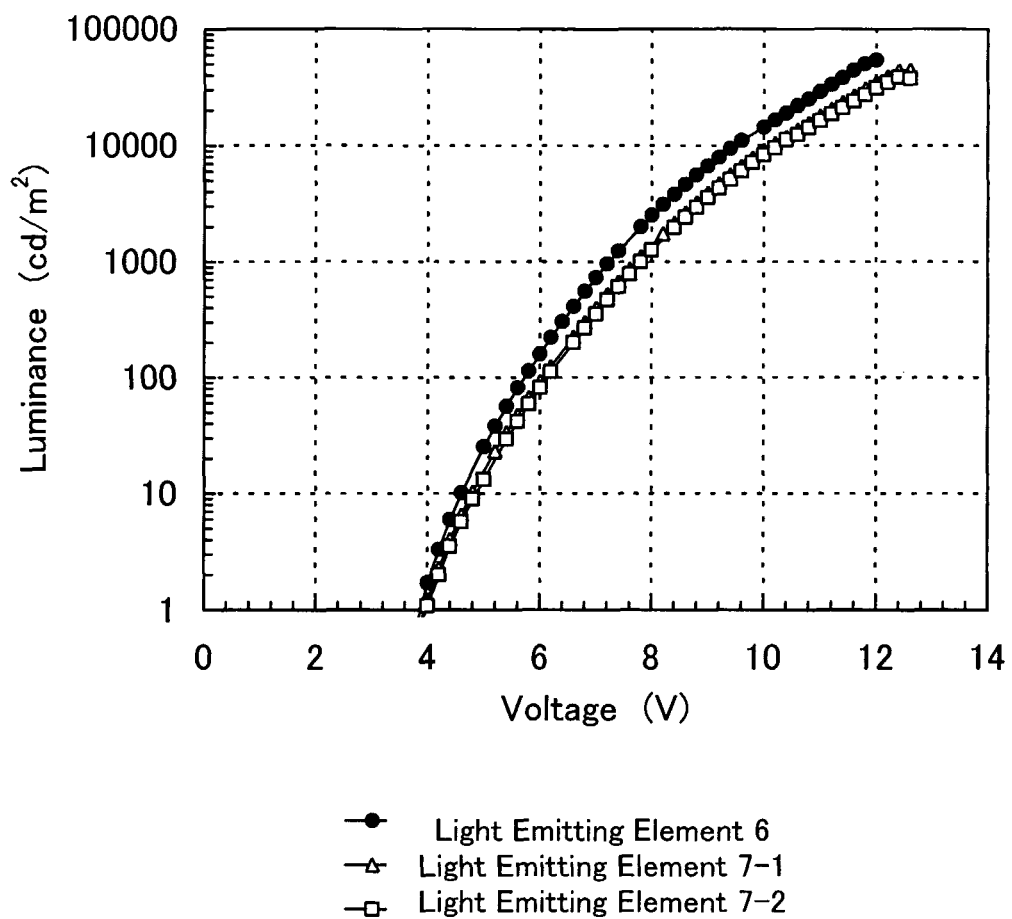
FIG. 39 is a graph showing voltage-luminance characteristics when light-emitting devices of Embodiments 6 and 7 are operated.
Figure 40:
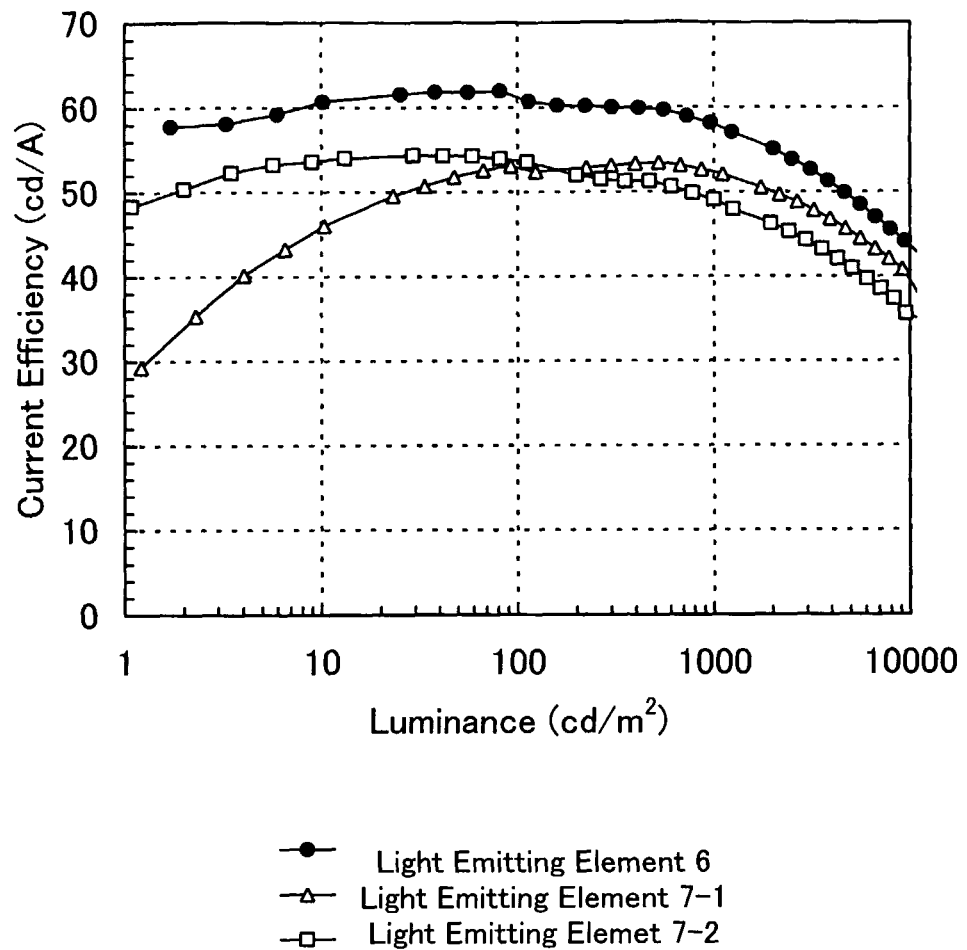
FIG. 40 is a graph showing luminance-current efficiency characteristics when light-emitting devices of Embodiments 6 and 7 are operated.

FIGS. 38 to 40 each show a measurement result. FIG. 38 shows a result regarding current density-luminance characteristics, FIG. 39 shows a result regarding voltage-luminance characteristics, and FIG. 40 shows a result regarding luminance-current efficiency characteristics. In FIG. 38, a horizontal axis represents current density (mA/cm$_2$), whereas a vertical axis represents luminance (cd/m$^2$). In addition, in FIG. 39, a horizontal axis represents voltage (V), whereas a vertical axis represents luminance (cd/m$^2$). Further, in FIG. 40, a horizontal axis represents luminance (cd/m$^2$), whereas a vertical axis represents current efficiency (cd/A). From these results, it was determined that, in the light-emitting element manufactured in the 2 present embodiment, a current flowed at a current density of 1.65 mA/cm$^2$ when a voltage of 7.2 V was applied, and light emission was obtained at a luminance of 959 cd/m$^2$. The current efficiency was 58.1 cd/A in light emission at a luminance of 959 cd/m$^2$, which is 17.6% when it is converted into external quantum efficiency (photon number/electron number). In addition, the maximum value of the external quantum efficiency was 18.7% in light emission at a luminance of 81.5 cd/m$^2$.

Figure 41A:
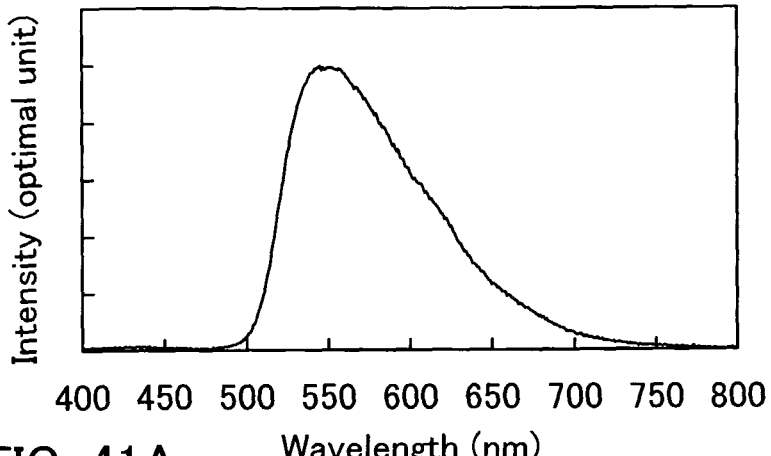
FIG. 41A to 41C are graphs showing an emission spectrum that is obtained when light-emitting devices of Embodiments 6 and 7 are operated.

FIG. 41A shows an emission spectrum of the light-emitting element manufactured in the present embodiment. In FIG. 41A, a horizontal axis represents wavelength (nm), and a vertical axis represents intensity (an arbitrary unit). As can be seen from FIG. 41A, the light-emitting element according to the present embodiment showed an emission peak at 545 nm, and emitted light was visible as green yellow light. Further, it was found that chromaticity coordinate in CIE colorimetric system was (x, y)=(0.43, 0.55).

[Embodiment 7]

In the present embodiment, two light-emitting elements (7-1) and (7-2) were manufactured, in which the mass ratios of CBP to Ir(Fdppr-iPr)$_2$(pic) in a third layer 605 are different from that in the light-emitting element manufactured in Embodiment 6 (hereinafter referred to as a light-emitting element (6)). Then, a relation between a concentration of Ir(Fdppr-iPr)$_2$(pic) contained in the light-emitting layer and emission efficiency was examined.

The light-emitting elements (7-1) and (7-2) have mass ratios of CBP to Ir(Fdppr-iPr)$_2$(pic) that are different from that of the light-emitting element that is manufactured in Embodiment 6, but the other aspects are the same. Therefore, as for a method for manufacturing the light-emitting elements (7-1) and (7-2), the descriptions of Embodiment 6 can be cited.

Mass ratios of CBP to Ir(Fdppr-iPr)$_2$(pic) in the light-emitting elements (7-1) and (7-2) and in the light-emitting element (6) are shown in Table 1.

TABLE 1

|  | Mass Ratio CBP:Ir(Fdppr-iPr)$_2$(pic) | Concentration of Ir(Fdppr-iPr)$_2$(pic) in light emitting layer (weight %) |
| --- | --- | --- |
| light-emitting element (6) | 1:0.01 | 1.0 |
| light-emitting elements (7-1) | 1:0.025 | 2.4 |
| light-emitting elements (7-2) | 1:0.05 | 4.8 |

Figure 41B:
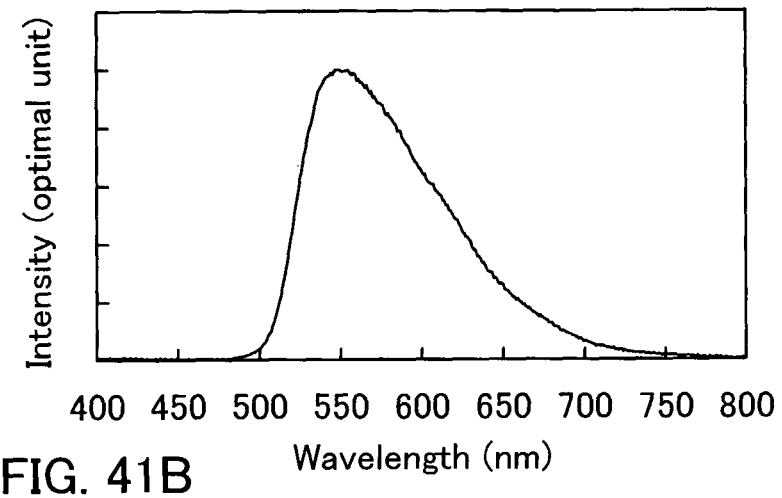
Figure 41C:
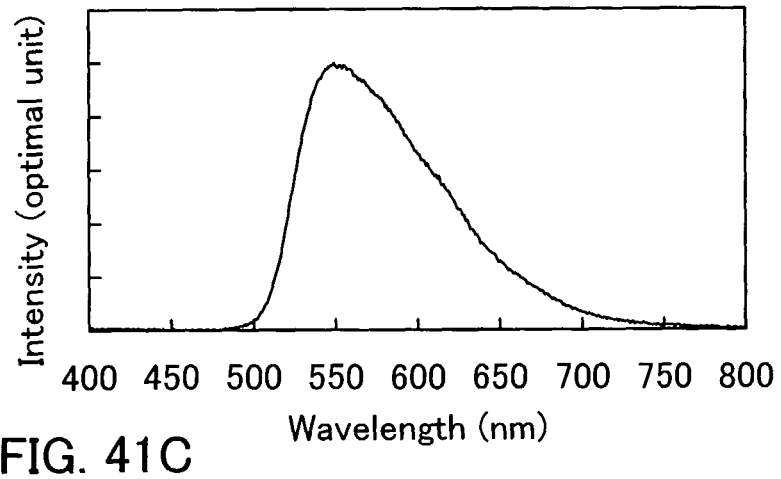

In a glove box (a sealing device) under a nitrogen atmosphere, a sealing operation was performed so that these light-emitting elements are not exposed to an atmosphere. Thereafter, operating characteristics of the light-emitting elements were measured. The measurement was conducted at a room temperature (an atmosphere kept at 25° C.). The measurement results are shown in FIGS. 38 to 40, 41B, and 41C with the data of Embodiment 6. FIG. 41B shows an emission spectrum of the light-emitting element (7-1), and FIG. 41C shows an emission spectrum of the light-emitting element (7-2).

The light-emitting elements (7-1), (7-2), and the light-emitting element (6) were made to emit light, and emission efficiency of each light-emitting element in luminescence at a luminance of 1000 cd/m$_2$ was examined. Then, emission efficiency (vertical axis) was plotted in FIG. 42 with respect to a concentration (horizontal axis) of Ir(Fdppr-iPr)$_2$(pic) contained in the third layer 605 (that is, contained in the light-emitting layer).

Figure 42:
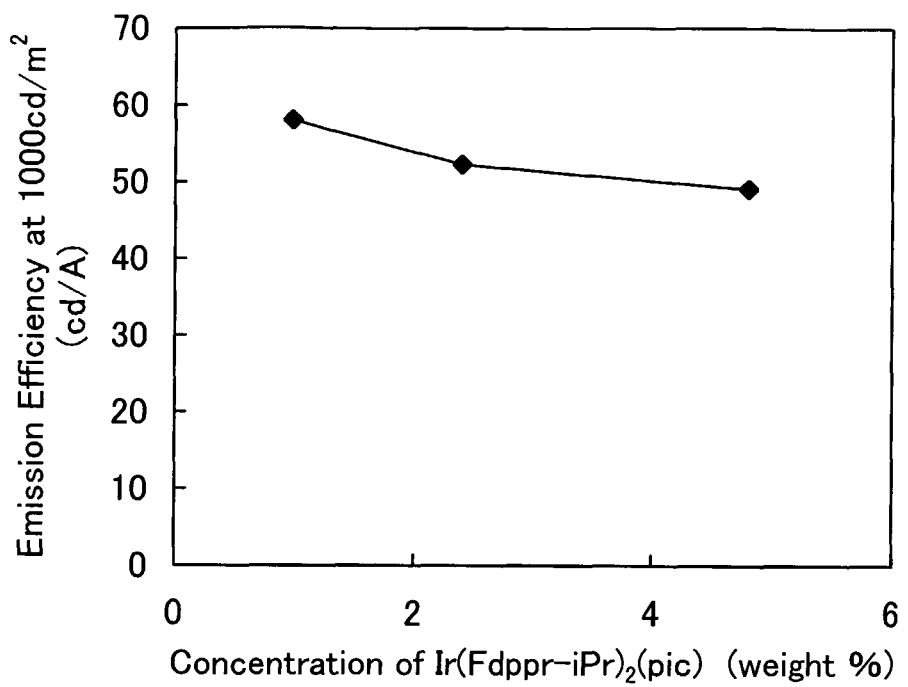
FIG. 42 is a graph showing a relation between a concentration of Ir(Fdppr-iPr)$_2$(pic) and emission efficiency.

As can be seen from FIG. 42, even when Ir(Fdppr-iPr)$_2$(pic) was contained in a high concentration, that is, by 5 weight %, a light-emitting element using Ir(Fdppr-iPr)$_2$(pic) as a luminescent substance emitted light with emission efficiency of approximately 50 cd/A, and it is found that the emission efficiency is scarcely lowered in accordance with a higher concentration of Ir(Fdppr-iPr)$_2$(pic). Accordingly, it is found that, among the organometallic complexes according to the present invention, particularly in an organometallic complex, in which an isopropyl group is introduced into 5 position of a pyrazine skeleton similarly to Ir(Fdppr-iPr)$_2$(pic), concentration quenching (concentration quenching is a phenomenon in which emission efficiency is lowered as a concentration of a luminescent substance (also referred to as a guest) contained in the light-emitting layer gets higher) is hardly caused.

This application is based on Japanese Patent Application serial no. 2005-076454 filed on Mar. 17, 2005, in Japanese Patent Office, and Japanese Patent Application serial no. 2005-346060 filed on Nov. 30, 2005, in Japanese Patent Office, the entire contents of which are hereby incorporated by reference.

EXPLANATION OF REFERENCE

10: substrate, 11: transistor, 12: light-emitting element, 13: first electrode, 14: second electrode, 15: layer, 16: interlayer insulating film, 17: wiring, 18: partition layer, 19: interlayer insulating film, 151: first electrode, 152: second electrode, 161: hole-injecting layer, 162: hole-transporting layer, 163: light-emitting layer, 164: electron-transporting layer, 165: electron-injecting layer, 301: glass substrate, 302: first electrode, 303: first layer, 304: second layer, 305: third layer, 306: forth layer, 307: fifth layer, 308: sixth layer, 309: second electrode, 401: glass substrate, 402: first electrode, 403: first layer, 404: second layer, 405: third layer, 406: forth layer, 407: fifth layer, 408: sixth layer, 409: second electrode, 501: sub frame, 502: sub frame, 503: sub frame, 504: sub frame, 601: glass substrate, 602: first electrode, 603: first layer, 604: second layer, 605: third layer, 606: forth layer, 607: fifth layer, 608: second electrode, 901: transistor, 902: transistor, 903: light-emitting element, 911: gate-signal line, 912: source-signal line, 913: writing gate-signal line driver circuit, 914: erasing gate-signal line driver circuit, 915: source-signal line driver circuit, 916: power source, 917: current supply line, 918; switch, 919: switch, 920: switch, 1001: transistor, 1002: transistor, 1003: gate-signal line, 1004: source-signal line, 1005: current supply line, 1006: electrode, 1901: substrate, 1902: electrode, 1904: partition layer, 1905: light-emitting layer, 1906: electrode, 1907: substrate, 501*a*: writing period, 501*b*: retention period, 502*a*: writing period, 502*b*: retention period, 503*a*: writing period, 503*b*: retention period, 504*a*: writing period, 504*b*: retention period, 504*c*: erasing period, 504*d*: non-emission period, 5521: main body, 5522: housing, 5523: display portion, 5524: keyboard, 5531: display portion, 5532: housing, 5533: speaker, 5551: display portion, 5552: main body, 5553: antenna, 5554: audio output portion, 5555: audio input portion: 5556: operation switch, 6500: substrate, 6503: FPC, 6504: printed wiring board (PWB), 6511: pixel portion, 6512: source-signal line driver circuit, 6513: writing gate-signal line driver circuit, 6514: erasing gate-signal line driver circuit

The invention claimed is:

1. An organometallic complex having a structure represented by a general formula (1),

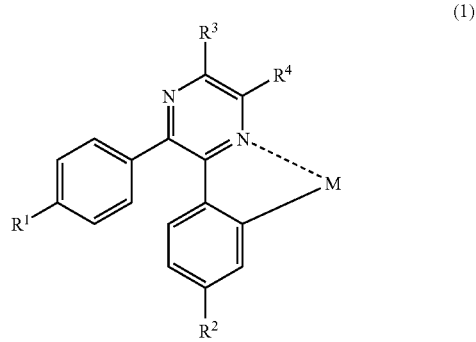

wherein each of R$^1$ and R$^2$ is any of a halogen group, a —CF$_3$ group, a cyano group, and an alkoxycarbonyl group, wherein R$^3$ is hydrogen, wherein R$^4$ is any of hydrogen and an alkyl group having 1 to 4 carbon atoms, and wherein M is an element that belongs to Group 9 or 10 of the periodic table.

2. The organometallic complex according to claim 1, wherein each of R$^1$ and R$^2$ is a fluoro group or a —CF$_3$ group.

3. The organometallic complex according to claim 1, wherein R$^4$ is a methyl group or an isopropyl group.

4. The organometallic complex according to claim 1, wherein M is an iridium or a platinum.

5. An organometallic complex having a structure represented by a general formula (2),

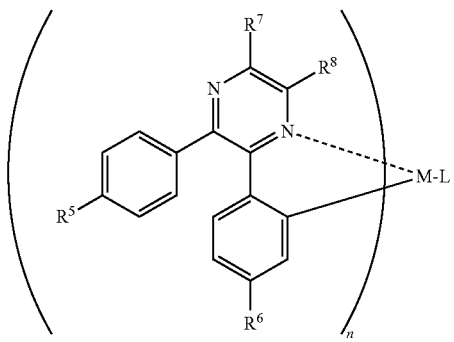
(2)

wherein each of $R^5$ and $R^6$ is any of a halogen group, a —$CF_3$ group, a cyano group, and an alkoxycarbonyl group,
wherein $R^7$ is hydrogen,
wherein $R^8$ is any of hydrogen and an alkyl group having 1 to 4 carbon atoms,
wherein n is any one of 1 and 2,
wherein M is an element that belongs to Group 9 or 10 of the periodic table,
wherein n is 2 when M is an element that belongs to Group 9 of the periodic table,
wherein n is 1 when M is an element that belongs to Group 10, and
L is a monoanionic ligand.

6. The organometallic complex according to claim 5, wherein the monoanionic ligand is a ligand represented by any of a structural formula (1) to a structural formula (7)

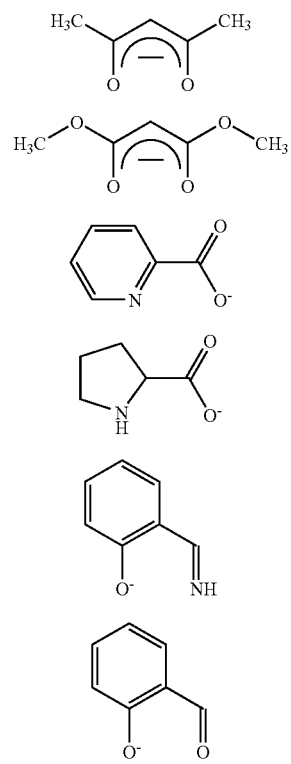

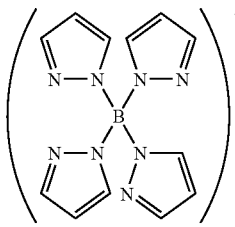
(7)

7. The organometallic complex according to claim 5, wherein each of $R^5$ and $R^6$ is a fluoro group or a —$CF_3$ group.

8. The organometallic complex according to claim 5, wherein $R^8$ is a methyl group or an isopropyl group.

9. The organometallic complex according to claim 5, wherein M is any one of an iridium and a platinum.

10. An organometallic complex having a structure represented by a general formula (3),

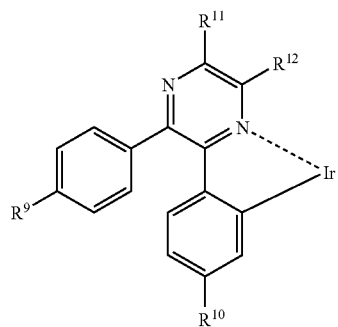
(3)

wherein each of $R^9$ and $R^{10}$ is any of a halogen group, a —$CF_3$ group, a cyano group, and an alkoxycarbonyl group,
wherein $R^{11}$ is hydrogen, and
wherein $R^{12}$ is any of hydrogen and an alkyl group having 1 to 4 carbon atoms.

11. The organometallic complex according to claim 10, wherein each of $R^9$ and $R^{10}$ is a fluoro group or a —$CF_3$ group.

12. The organometallic complex according to claim 10, wherein $R^{12}$ is a methyl group or an isopropyl group.

13. An organometallic complex having a structure represented by a general formula (4),

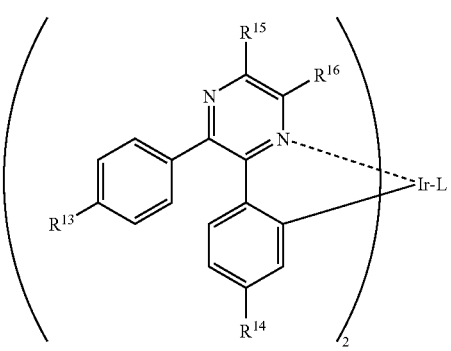
(4)

wherein each of $R^{13}$ and $R^{14}$ is any of a halogen group, a —$CF_3$ group, a cyano group, and an alkoxycarbonyl group,
wherein $R^{15}$ is hydrogen,
wherein $R^{16}$ is any of hydrogen and an alkyl group having 1 to 4 carbon atoms, and wherein L is a monoanionic ligand.

14. The organometallic complex according to claim 13, wherein the monoanionic ligand is a ligand represented by any of a structural formula (1) to a structural formula (7)

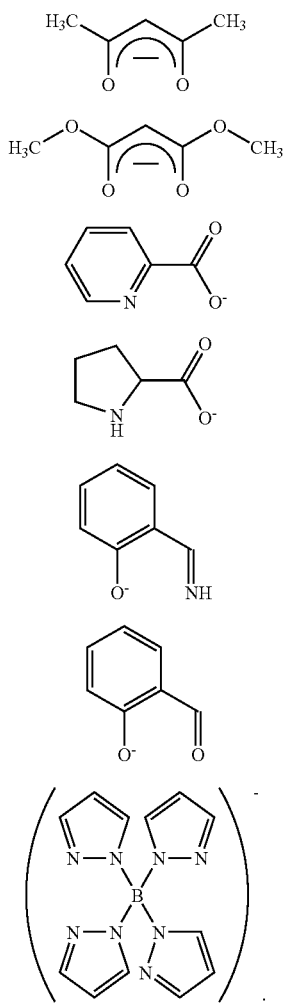

15. The organometallic complex according to claim 13, wherein each of $R^{13}$ and $R^{14}$ is a fluoro group or a $-CF_3$ group.

16. The organometallic complex according to claim 13, wherein $R^{16}$ is a methyl group or an isopropyl group.

17. An organometallic complex having a structure represented by a general formula (5),

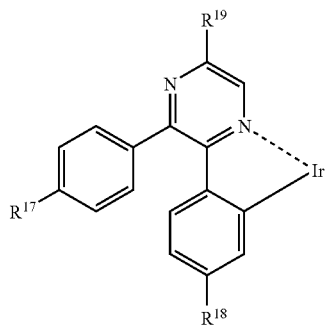

wherein each of $R^{17}$ and $R^{18}$ is any of a halogen group, a $-CF_3$ group, a cyano group, and an alkoxycarbonyl group, and wherein $R^{19}$ is hydrogen.

18. The organometallic complex according to claim 17, wherein each of $R^{17}$ and $R^{18}$ is a fluoro group or a $-CF_3$ group.

19. An organometallic complex having a structure represented by a general formula (6),

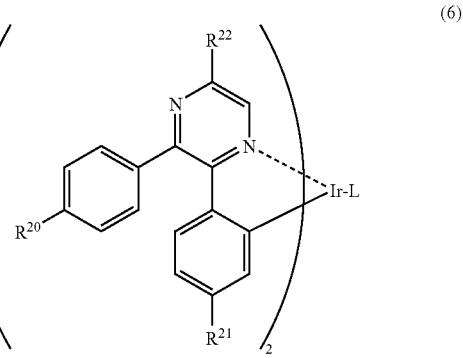

wherein each of $R^{20}$ and $R^{21}$ is any of a halogen group, a $-CF_3$ group, a cyano group, and an alkoxycarbonyl group, wherein $R^{22}$ is hydrogen, and wherein L is a monoanionic ligand.

20. The organometallic complex according to claim 19, wherein the monoanionic ligand is a ligand represented by any of a structural formula (1) to a structural formula (7)

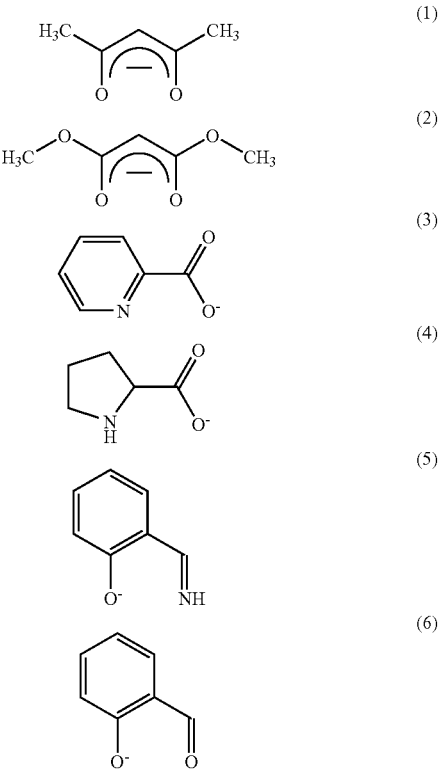

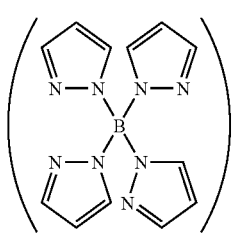

21. The organometallic complex according to claim 19, wherein each of $R^{20}$ and $R^{21}$ is a fluoro group or a —$CF_3$ group.

22. An organometallic complex having a structure represented by a general formula (13),

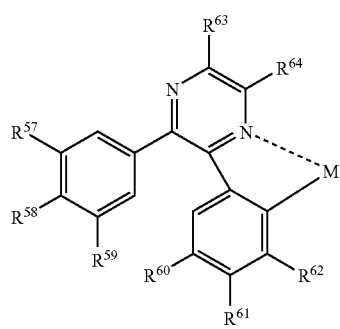

wherein each of $R^{57}$ to $R^{62}$ is independently any of a halogen group and a —$CF_3$ group, wherein $R^{63}$ is hydrogen, wherein $R^{64}$ is any of hydrogen and an alkyl group having 1 to 4 carbon atoms, and M is an element that belongs to Group 9 or 10 of the periodic table.

23. The organometallic complex according to claim 22, wherein M is an iridium or a platinum.

24. An organometallic complex having a structure represented by a general formula (14),

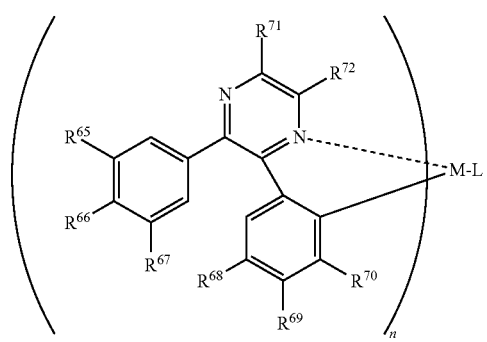

wherein each of $R^{65}$ to $R^{70}$ is independently any of a halogen group and a —$CF_3$ group, wherein $R^{71}$ is hydrogen, wherein $R^{72}$ is any of hydrogen and an alkyl group having 1 to 4 carbon atoms, wherein n is any one of 1 and 2, wherein M is an element that belongs to Group 9 or 10 of the periodic table, wherein n is 2 when M is an element that belongs to Group 9 of the periodic table, wherein n is 1 when M is an element that belongs to Group 10, and wherein L is a monoanionic ligand.

25. The organometallic complex according to claim 24, wherein the monoanionic ligand is a ligand represented by any of a structural formula (1) to a structural formula (7)

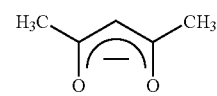

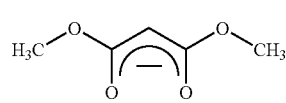

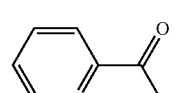

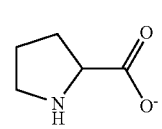

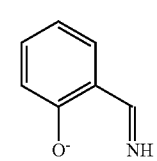

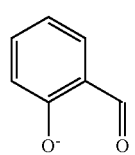

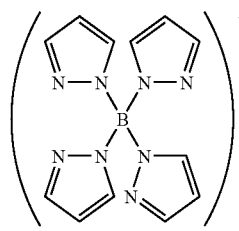

26. The organometallic complex according to claim 24, wherein M is an iridium or a platinum.

27. An organometallic complex having a structure represented by a general formula (15), (15)

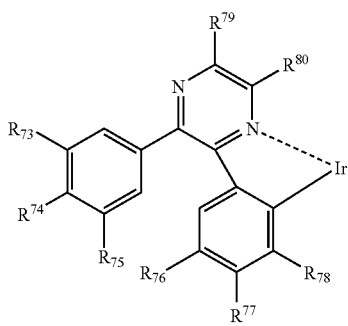

wherein each of $R^{73}$ to $R^{78}$ is independently any of a halogen group and a —$CF_3$ group, wherein $R^{79}$ is hydrogen, and wherein $R^{80}$ is any of hydrogen and an alkyl group having 1 to 4 carbon atoms.

28. An organometallic complex having a structure represented by a general formula (16), (16)

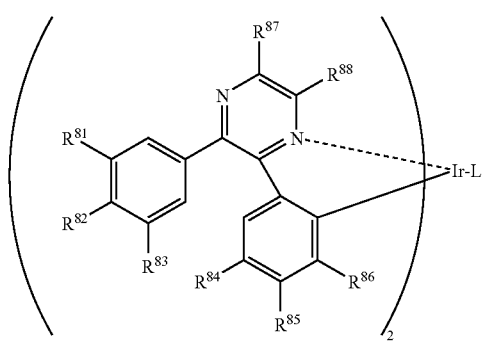

wherein each of $R^{81}$ to $R^{86}$ is independently any of a halogen group and a —$CF_3$ group, wherein $R^{87}$ is hydrogen, wherein $R^{88}$ is any of hydrogen and an alkyl group having 1 to 4 carbon atoms, and wherein L is a monoanionic ligand.

29. The organometallic complex according to claim 28, wherein the monoanionic ligand is a ligand represented by any of a structural formula (1) to a structural formula (7)

(1)

(2)

(3)

(4)

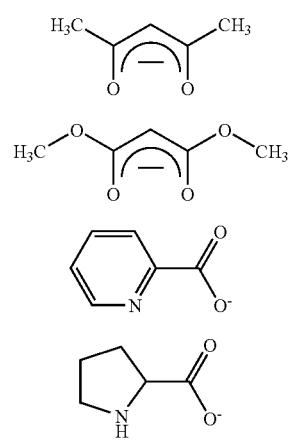

(5)

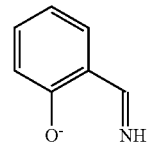

(6)

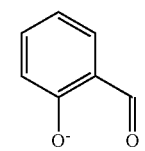

(7)

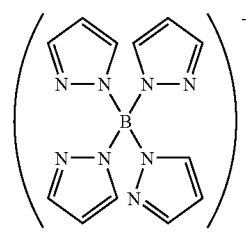

30. An organometallic complex having a structure represented by a general formula (17), (17)

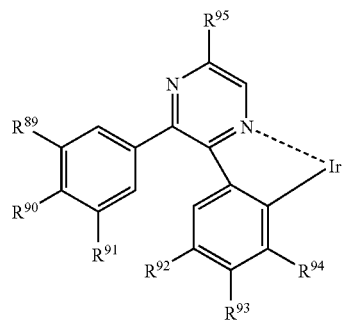

wherein each of $R^{89}$ to $R^{94}$ is independently any of a halogen group and a —$CF_3$ group, and wherein $R^{95}$ is hydrogen.

31. An organometallic complex having a structure represented by a general formula (18), (18)

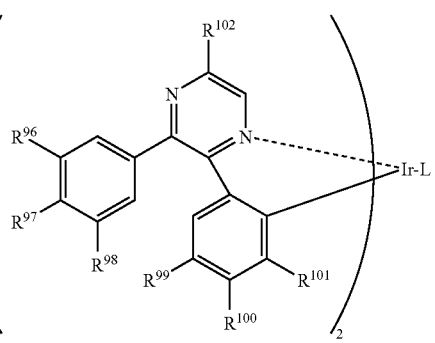

wherein each of $R^{96}$ to $R^{101}$ is independently any of a halogen group and a —$CF_3$ group, wherein $R^{102}$ is hydrogen, and wherein L is a monoanionic ligand.

32. The organometallic complex according to claim 31, wherein the monoanionic ligand is a ligand represented by any of a structural formula (1) to a structural formula (7)

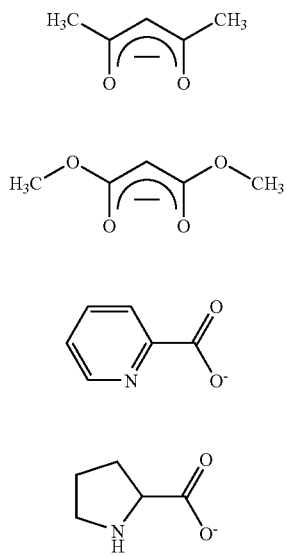

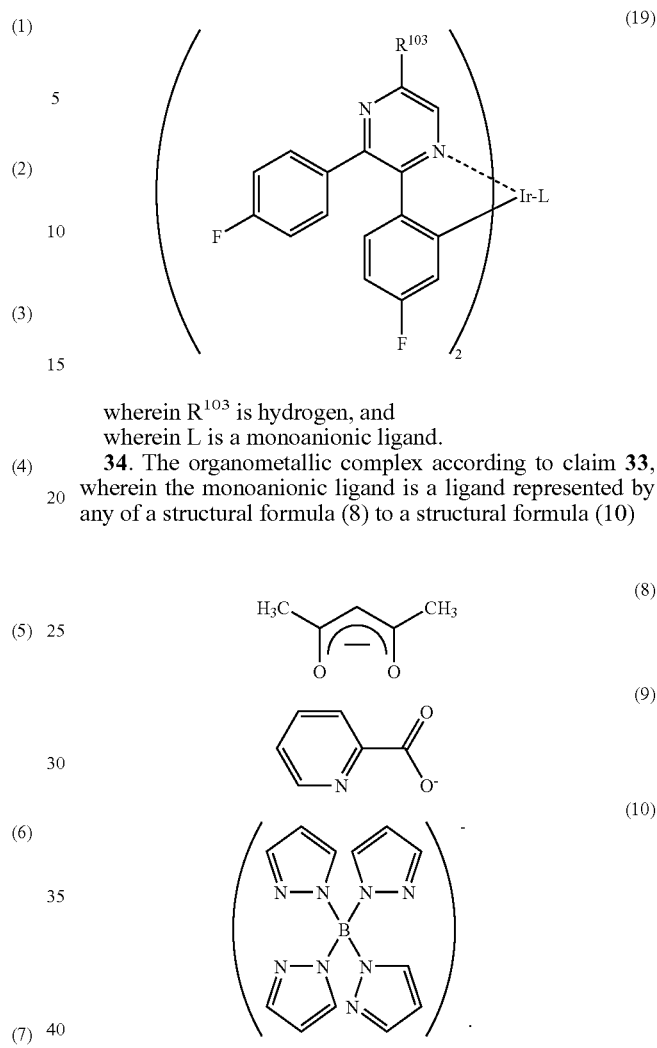

33. An organometallic complex having a structure represented by a general formula (19), wherein $R^{103}$ is hydrogen, and
wherein L is a monoanionic ligand.

34. The organometallic complex according to claim 33, wherein the monoanionic ligand is a ligand represented by any of a structural formula (8) to a structural formula (10)

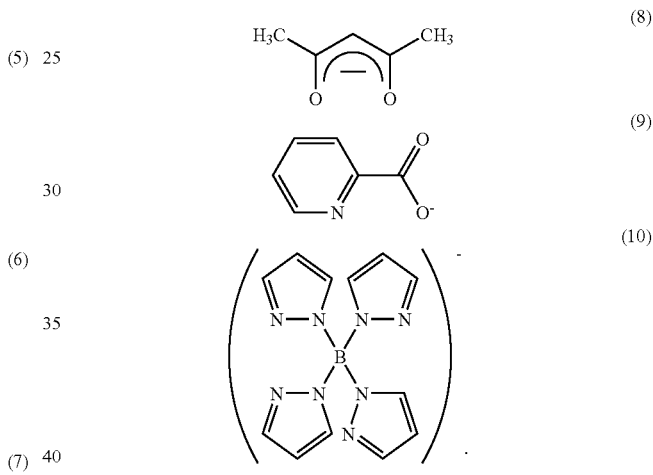

35. A light emitting device comprising a light-emitting element which includes a layer between a pair of electrodes, wherein the layer containing the organometallic complex according to any one of claims 1, 5, 10, 13, 17, 19, 22, 24, 27, 28, 30, 31 and 33.

36. An electronic device comprising a light emitting device comprising a light-emitting element which includes a layer between a pair of electrodes, wherein the layer containing the organometallic complex according to any one of claims 1, 5, 10, 13, 17, 19, 22, 24, 27, 28, 30, 31 and 33.

* * * * *